(12) United States Patent
Jones et al.

(10) Patent No.: US 10,870,886 B2
(45) Date of Patent: Dec. 22, 2020

(54) MOLECULAR DIAGNOSIS OF FSHD BY EPIGENETIC SIGNATURE

(71) Applicant: University of Massachusetts Medical Center, Shrewsbury, MA (US)

(72) Inventors: Peter L. Jones, Boston, MA (US); Takako Jones, Boston, MA (US); Johnny Salameh, Boston, MA (US); Colin Quinn, Boston, MA (US); Oliver D. King, Boston, MA (US)

(73) Assignee: University of Massachusetts Medical Center, Boston, MA (US)

( * ) Notice: Subject to any disclaimer, the term of this patent is extended or adjusted under 35 U.S.C. 154(b) by 6 days.

(21) Appl. No.: 15/516,291

(22) PCT Filed: Oct. 7, 2015

(86) PCT No.: PCT/US2015/054462
§ 371 (c)(1),
(2) Date: Mar. 31, 2017

(87) PCT Pub. No.: WO2016/057648
PCT Pub. Date: Apr. 14, 2016

(65) Prior Publication Data
US 2017/0306403 A1   Oct. 26, 2017

Related U.S. Application Data

(60) Provisional application No. 62/062,085, filed on Oct. 9, 2014.

(51) Int. Cl.
*C12Q 1/6883* (2018.01)
(52) U.S. Cl.
CPC ...... *C12Q 1/6883* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

2012/0122088 A1*  5/2012  Zou .................... C12Q 1/6827
                                                        435/6.11
2013/0288976 A1   10/2013  van der Maarel et al.

FOREIGN PATENT DOCUMENTS

EP           2175037 A1     4/2010

OTHER PUBLICATIONS

Feng (PNAS 2010 vol. 107 No. 19 pp. 8689-8694 (Year: 2010).*
De Greef et al. (Human Mutation 2009 vol. 30 p. 1449) (Year: 2009).*
Lemmers et al. (Science 2010 vol. 329 p. 1650) (Year: 2010).*
Li, Y. and Tollefsbol, T. O., "DNA methylation detection: Bisulfite genomic sequencing analysis", *Methods Mol. Biol.*, vol. 791; 11-21 (2011).
Notification of Transmittal of the International Search Report and the Written Opinion of the International Searching Authority for International Application No. PCT/US2015/054462, entitled: "Molecular Diagnosis of FSHD by Epigenetic Signature", dated Jan. 14, 2016.
Van Overveld, P. G. M., et al., "Variable Hypomethylation of D4Z4 in Facioscapulohumeral Muscular Dystrophy", *Ann. Neurol.*, vol. 58; 569-576 (2005).

* cited by examiner

*Primary Examiner* — Katherine D Salmon
(74) *Attorney, Agent, or Firm* — Hamilton, Brook, Smith & Reynolds, P.C.

(57) ABSTRACT

The present invention includes methods of determining whether an individual in need thereof has, or is at risk of developing, facioscapulohumeral muscular dystrophy (FSHD).

14 Claims, 27 Drawing Sheets
Specification includes a Sequence Listing.

A

B

A

```
          BSS 1438F
5'- GTTTTGTTGGAGGAGTTTTAGGACGCGGGGTTGGGACGGGGTCGGGTGGTTCGGGGTAGGGCGGTGGTTTTTT
               YG in 10A166
    TTCGCGGGGAA░TTTGGTTGGTTACGGAGGGGCGTGTTTTCGTTTCGTTTTTTTATCGGGTTGATCGGTTTG
                           DUX4 Exon 2         A in 10A166, 4A166
    GGATTTTTGTTTTTAGGTTTAGGTTCGGTGAGAGATTTTATAT░GCGGAGAATTGTTATTTTTTTTTTGGGTA
    DUX4 Exon 2                          (CpG #16)
    TTTCGGGGATTTTAGAGTCGGTTTAGGTATTAGTAGGTGGGTCGTTTATTGCGTACGCGCGGGTTTGCGGGTA
    GTCGTTTGGGTTGTGGGAGTAGTTCGGGTAGAGTTTTTTTGTTTTTTATTAGTTTATTTCGTCGTTTGATCG
                      G in 10A166, 10A176T
    TTTTTTTTTTATTTTTATTTTTT░TTTTCGGAAAACGCGTCGTTTTTTGGGTTGGGTGGAGATTTTCGTTTCG
    CGAAATATCGGGTTTCGCGTAGCGTTCGGGTTTGATATCGTTTCGGCGGTTCGTTTTTTTTGCGTTTTCGCGT
                                   7806  7812    7820    7827
                                    G    G       A       YG
    TATCGTCGTTCGTTCGTTCGGGTTTTTGTAGT░TTTAG░TGTTAGC░CGGAG░TTTGGCGGTTAAAAGTAT
                                                (CpG #55)    AAAACCGCCAATTTTCATA
ATTTTTGTT-3'                                                  BSS 3626R
TAAAAACAA-5'         Non-permissive haplotype signatures
                     7806 G = 4A166, 10A166, 10A180T, 10B161T
                     7812 G = 4A166, 10A166, 10A180T
                     7820 A = 4A160, 4C166, 10A166, 10A176T, 10A180T
                     7827 G = 4A166, 4A166H, 10A176T, 10A166, 10B161T
```

B

C

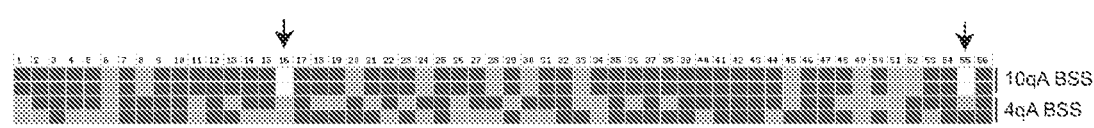

D

```
          BSS 4ALF
5'- TTATTTATGAAGGGGTGGAGTTTGTTTGTTTGTGGGTTTTTATAAGGGCGGTTGGTTGGTTGGTTGGTTGTTC
    GGGTAGGTTTTTTGGTTGTATTTGTCGTAGTGTATAGTTCGGTTGAGGTGTACGGGAGTTCGTCGGTTTTTTT
    TGTTCGCGTTCGTTCGTGAAATTTCGGTCGGGGTTTATCGCGATGGTTTTTTCGATATTTTCGGATAGTATT
    TTTTTCGCGGAAGTTCGGGGACGAGGACGGCGACGGAGATTCGTTTGGATTCGAGTTAAAGCGAGGTTTCTGC
               G    G     A    YG
    GAGTTTGTAGT░TTTAG░TGTTAC░CGGAG░TTTGGCGGTTAAAAGTATATTTTTGTT-3'
                                    AAAACCGCCAATTTTCATATAAAAACAA-5'
                                    BSS 3626R
```

FIGS. 10A-10D

E
　　　BSS +475
5'-▒▒▒▒▒▒▒▒▒▒▒▒▒▒▒▒▒▒▒▒▒▒GGAGGTAGGGAGGAACGGAGGGAAAGATAGAGCGACGTAGGGATTGGGGG

CGGGCGGGAGGGAGTCGGGGACGGGGGGAGGAAGGTAGGGAGGAAAAGCGGTTTTCGGTTTTCGGGAGTAGCG

GGATTTTCGTTTTTCGGGAAAACGGTTAGCGTTCGGCGCGGGTTGAGGGTTGGGTTTATAGTCGTCGCGTCGG

TCGGCGGGGTATTATTTATTCGTTTCGGTTTCGTGGTTTAGGGAGTGGGCGGTTTTTTTCGGGATAAAAGATC

GGGATTCGGGTTGTCGTCGGGTTTTTATTCGCGCGGTTTATAGATCGTATATTTTTAGGTTGAGTTTTGTAAC

GCGGCGCGAGGTCGATAGTTTCGGTTACGGAGGAGTTATACGTAGGACGACGGAGGCGTGATTTTGGTTTTCG

CGTGGTTTTGTTTTTCGTAAGGCGGTTTGTTGTTTACGTTTTTTCGGTTTTCGAAAGGTTGGTTATGTCGATT
　　　　　　　　　　　　　　　　　　　　　　　　　　G in 10q D4Z4
GTTTGTTTTCGGAGTTTTGCGGGTATTCGGAAATATGTAGGG▒AGGGTGTAAGTTCGGTACGGTGTT-3'
　　　　　　　　　　　　　　　　　　　　　　　　　　　▒▒▒▒▒▒▒▒▒▒▒▒▒▒▒▒▒▒▒▒▒▒-5'
　　　　　　　　　　　　　　　　　　　　　　　　　　　　BSS -1036

FIG. 10E

SEQUENCE LISTING

```
<160> NUMBER OF SEQ ID NOS: 17

<210> SEQ ID NO 1
<211> LENGTH: 593
<212> TYPE: DNA
<213> ORGANISM: Artificial Sequence
<220> FEATURE:
<223> OTHER INFORMATION: BS-Converted PCR product

<400> SEQUENCE: 1
gttttgttgg aggagtttta ggacgcgggg ttgggacggg gtcgggtggt tcggggtagg      60
gcggtggttt ttttcgcgg ggaatatttg gttggttacg gaggggcgtg ttttcgtttc     120
gtttttttat cgggttgatc ggtttgggat ttttgttttt taggtttagg ttcggtgaga     180
gattttatat cgcggagatt tgttattttt ttttgggtat ttcggggatt ttagagtcgg     240
tttaggtatt agtaggtggg tcgtttattg cgtacgcgcg ggtttgcggg tagtcgtttg     300
ggttgtggga gtagttcggg tagagttttt ttgttttttt attagtttat ttcgtcgttt     360
gatcgttttt tttttatttt tattttttat tttcggaaaa cgcgtcgttt tttggttgg      420 gtggagattt tcgtttcgcg aaatatcggg tttcgcgtag cgttcgggtt tgatatcgtt     480
tcggcggttc gttttttttg cgttttcgcg ttatcgtcgt tcgttcgttc gggttttttgt    540 agttttttag ttgttagcgc ggagtttttg gcggttaaaa gtatattttt gtt            593

<210> SEQ ID NO 2
<211> LENGTH: 353
<212> TYPE: DNA
<213> ORGANISM: Artificial Sequence
<220> FEATURE:
<223> OTHER INFORMATION: BS-Converted PCR product

<400> SEQUENCE: 2
ttatttatga aggggtggag tttgtttgtt tgtgggtttt tataagggcg gttggttggt      60
tggttggttg ttcgggtagg tttttggtt gtatttgtcg tagtgtatag ttcggttgag     120
gtgtacggga gttcgtcggt tttttttgt tcgcgttcgt tcgtgaaatt tcggtcgggg     180
```

```
tttatcgcga tggttttttc gatattttcg gatagtattt ttttcgcgga agttcgggga    240
cgaggacggc gacggagatt cgtttggatt tcgagttaaa gcgaggtttt gcgagtttgt    300
agttttttag ttgttagcgc ggagtttttg gcggttaaaa gtatattttt gtt          353
```

<210> SEQ ID NO 3
<211> LENGTH: 28
<212> TYPE: DNA
<213> ORGANISM: Artificial Sequence
<220> FEATURE:
<223> OTHER INFORMATION: BBS primer 3262r

<400> SEQUENCE: 3

```
aacaaaaata tacttttaac cgccaaaa                                        28
```

<210> SEQ ID NO 4
<211> LENGTH: 880
<212> TYPE: DNA
<213> ORGANISM: Homo sapiens

<400> SEQUENCE: 4

```
ggtaccagca ggtgggccgc ctactgcgca cgcgcgggtt tgcgggcagc cgcctgggct     60
gtgggagcag cccgggcaga gctctcctgc ctctccacca gcccaccccg ccgcctgacc    120 gcccctccc cacccccacc cccaccccc ggaaaacgcg tcgtcccctg ggctgggtgg     180 agaccccgt cccgcgaaac accgggcccc gcgcagcgtc cgggcctgac accgctccgg    240
cggctcgcct cctctgcgcc cccgcgccac cgtcgcccgc ccgcccgggc ccctgcagcc    300
tcccagctgc cagcgcggag ctcctggcgg tcaaaagcat acctctgtct gtctttgccc    360
gcttcctggc tagacctgcg cgcagtgcgc acccggctg acgtgcaagg gagctcgctg     420
gcctctctgt gcccttgttc ttccgtgaaa ttctggctga atgtctcccc ccaccttccg    480
acgctgtcta gcaaacctg gattagagtt acatctcctg gatgattagt tcagagatat     540
attaaaatgc ccctccctg tggatcctat agaagatttg catctttgt gtgatgagtg     600 cagagatatg tcacaatatc ccctcccgta gaaaaagcct gaaattggtt tacataactt    660
cggtgatcag tgcagatgtg tttcagaact ccatagtaga ctgaacctag agaatggtta    720
catcacttag gtgatcagtg tagagatatg ttaaaattct cgtgtagaca gagcctagac    780
aattgttaca tcacctagtg atcagtgcag ggataagtca taaagcctcc tgtaggcaga    840
gtgtaggcaa gtgttccctc cctgggctga tcagtgcaga                          880
```

<210> SEQ ID NO 5
<211> LENGTH: 1199
<212> TYPE: DNA
<213> ORGANISM: Homo sapiens

<400> SEQUENCE: 5

```
ggtaccagca ggtgggccgc ctactgcgca cgcgcgggtt tgcgggcagc cgcctgggct     60
gtgggagcag cccgggcaga gctctcctgc ctctccacca gcccaccccg ccgcctgacc    120 gcccctccc cacccccacc cccaccccc ggaaaacgcg tcgtcccctg ggctgggtgg     180 agaccccgc ccgcgaaaca ccgggcccg cgcagcgtcc gggcctgacc tccgctccgg     240
cggctcgcct cctctgcgcc cccgcgccac cgtcgcccgc ccgcccgggc ccctgcagcc    300
gcccagctgc cagcacggag cgcctggcgg cggaacgcag accccaggcc cggcgcacac    360
cggggacgct gagcgttcca ggcgggaggg aaggcgggca gagatggaga gaggaacggg    420
```

| | |
|---|---|
| agacctagag gggcggaagg acgggcggag ggacgttagg agggaggcag ggaggcaggg | 480 |
| aggcagggag gaacggaggg agagacagag cgacgcaggg actgggggcg ggcgggaggg | 540 |
| agccggggac ggacgggggg aggaaggcag ggaggaaaag cggtcctcgg cctccgggag | 600 |
| tagcgggacc cccgcccctcc gggaaaacgg tcagcgtccg gcgcgggctg agggctgggc | 660 |
| ccacagccgc cgcgccggcc ggcggggcac cacccattcg ccccggttcc ggggcccagg | 720 |
| gagtgggcgt tttcctccgg gacaaaagac cgggactcga gactccgttc aataaatggt | 780 |
| gctgggataa ctggctagcc acatgctgaa gattgaactg ggccccttc ttacaccata | 840 |
| cacaaaaatg aactcaggat ggattaaaga cttaagtgta aaacccaaaa atataaaaac | 900 |
| cctggaagac aacctaggca ataccatcct ggacataagg acaggcaaag atttcatgac | 960 |
| aaagacaaca aaagcaatag caatgaaagc aaaaattgac gtgggatcta gttaaactaa | 1020 |
| agagcttcta cacagcaaaa gaaactatca acaaagtaaa caggcaactt gcagattggg | 1080 |
| agaaagtatt tacaaactat gcatctgaca aaggtctaat atccagcatc tataaggaac | 1140 |
| ttaaacaaat ttacaagaga aaaacaaccc cattaaaaag tgggccaagg acataaaga | 1199 |

<210> SEQ ID NO 6
<211> LENGTH: 578
<212> TYPE: DNA
<213> ORGANISM: Artificial Sequence
<220> FEATURE:
<223> OTHER INFORMATION: BS-Converted PCR product

<400> SEQUENCE: 6

| | |
|---|---|
| ttaggaggga gggagggagg tagggaggta gggaggaacg gagggaaaga tagagcgacg | 60 |
| tagggattgg gggcgggcgg gagggagtcg gggacggggg gaggaaggta gggaggaaaa | 120 |
| gcggttttcg gttttcggga gtagcgggat tttcgttttt cggaaaacg gttagcgttc | 180 |
| ggcgcgggtt gagggttggg tttatagtcg tcgcgtcggt cggcggggta ttatttattc | 240 |
| gtttcggttt cgtggtttag ggagtgggcg ttttttttcg ggataaaaga tcggattcg | 300 |
| ggttgtcgtc gggttttttat tcgcgcggtt tatagatcgt atatttttag gttgagtttt | 360 |
| gtaacgcggc gcgaggtcga tagtttcggt tacggaggag ttatacgtag gacgacggag | 420 |
| gcgtgatttt ggttttcgcg tggttttgtt tttcgtaagg cggtttgttg tttacgtttt | 480 |
| ttcggttttc gaaaggttgg ttatgtcgat tgtttgtttt cggagttttg cgggtattcg | 540 |
| gaaatatgta gggaagggtg taagttcggt acggtgtt | 578 |

<210> SEQ ID NO 7
<211> LENGTH: 25
<212> TYPE: DNA
<213> ORGANISM: Artificial Sequence
<220> FEATURE:
<223> OTHER INFORMATION: BSS primer 1036

<400> SEQUENCE: 7

| | |
|---|---|
| aacaccgtac cgaacttaca ccctt | 25 |

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer BSS1438F

<400> SEQUENCE: 8

| | |
|---|---|
| gttttgttgg aggagtttta gga | 23 |

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer BSS3742R

<400> SEQUENCE: 9
aacattcaac caaaatttca craaa                                       25

<210> SEQ ID NO 10
<211> LENGTH: 29
<212> TYPE: DNA
<213> ORGANISM: Artificial Sequence
<220> FEATURE:
<223> OTHER INFORMATION: Oligonucleotide primer BSS3626R

<400> SEQUENCE: 10
aacaaaaata tacttttaac crccaaaaa                                   29

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide primer BSS4qALF

<400> SEQUENCE: 11
ttatttatga agggtggag tttgtt                                       26

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer BSS3702R

<400> SEQUENCE: 12
aaaaccaacr aactccctta cac                                         23

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer BSS167F

<400> SEQUENCE: 13
ttttgggttg ggtggagatt tt                                          22

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide primer BSS1036R

<400> SEQUENCE: 14
aacaccrtac craacttaca ccctt                                       25

<210> SEQ ID NO 15
<211> LENGTH: 23
<212> TYPE: DNA
<213> ORGANISM: Artificial Sequence
<220> FEATURE:

```
<223> OTHER INFORMATION: Oligonucleotide primer BSS475F

<400> SEQUENCE: 15
ttaggaggga gggagggagg tag                                           23

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer hANKRD1 forward

<400> SEQUENCE: 16
gcctacgttt ctgaaggctg                                               20

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide primer hANKRD1 reverse

<400> SEQUENCE: 17
gtggattcaa gcatatcacg gaa                                           23
```

MOLECULAR DIAGNOSIS OF FSHD BY EPIGENETIC SIGNATURE

RELATED APPLICATION

This application is the U.S. National Stage of International Application NO: PCT/US2015/054462, filed Oct. 7, 2015, which designated the U.S., published in English, and claims the benefit of U.S. Application No. 62/062,085, filed Oct. 9, 2014. The entire teachings of the above applications are incorporated herein by reference.

GOVERNMENT SUPPORT

This invention was made with government support under Grant No. R01AR062587 from National Institutes of Health. The government has certain rights in the invention.

INCORPORATION BY REFERENCE OF MATERIAL IN ASCII TEXT FILE

This application incorporates by reference the Sequence Listing contained in the following ASCII text file:
 a) File name: 07462006002CORRECTEDSEQUENCE-LISTING.txt, created Apr. 18, 2017, 8 KB in size.

BACKGROUND OF THE INVENTION

Facioscapulohumeral muscular dystrophy (FSHD) is associated with aberrant epigenetic regulation of the chromosome 4q35 D4Z4 macrosatellite. Chromatin changes due to large deletions of heterochromatin (FSHD1) or mutations in chromatin regulatory proteins (FSHD2) lead to relaxation of epigenetic repression and increased expression of the deleterious double homeobox 4 (DUX4) gene encoded within the distal D4Z4 repeat. However, there is wide variability in clinical presentation of FSHD, and many individuals with the genetic requirements for FSHD remain asymptomatic throughout their lives.

Therefore, a need exists for improved methods of detecting whether an individual, including an asymptomatic individual, has or is at risk for developing FSHD.

SUMMARY OF THE INVENTION

The invention generally is directed to methods of determining whether an individual has, or is at risk of developing, facioscapulohumeral muscular dystrophy (FSHD).

In one embodiment, the invention includes a method of determining whether an individual in need thereof has, or is at risk of developing, facioscapulohumeral muscular dystrophy (FSHD) comprising the steps of performing a DNA methylation analysis of a) deoxycytosine-phosphate-deoxyguanine dinucleotides (CpGs) in a distal D4Z4 repeat unit of a D4Z4 repeat array and a proximal region of an A-type subtelomere of a chromosome 4qA allele of chromosome 4q, b) CpGs in all DUX4 5' regions in the D4Z4 array of chromosome 4q and in the D4Z4 array of chromosome 10q, or c) a combination thereof. According to the invention, if less than about 25% of the CpGs in the first quartile of (a) are methylated, and/or less than about 60% of the CpGs in (b) are methylated, then the individual has, or is at risk of developing, FSHD.

In another embodiment, the invention includes a method of determining whether an individual in need thereof has, or is at risk of developing, facioscapulohumeral muscular dystrophy (FSHD) comprising the steps of 1) performing a DNA methylation analysis of a) deoxycytosine-phosphate-deoxyguanine dinucleotides (CpGs) in a distal D4Z4 repeat unit of a D4Z4 repeat array and a proximal region of an A-type subtelomere of a chromosome 4qA allele of chromosome 4q, b) CpGs in all DUX4 5' regions in the D4Z4 array of chromosome 4q and in the D4Z4 array of chromosome 10q, or c) a combination thereof, wherein if less than about 25% of the CpGs in the first quartile of (a) are methylated, and/or less than about 60% of the CpGs in (b) are methylated, then the individual has, or is at risk of developing, FSHD; and 2) treating the individual when the individual is determined to have, or be at risk for developing, FSHD.

The invention provides new methods for determining whether an individual has, or is at risk of developing FSHD. The invention has advantages over current methods. For example, the methods of the present invention are useful for distinguishing between individuals having FSHD1 and individuals who do not have FSHD1, regardless of familial relation status.

BRIEF DESCRIPTION OF THE DRAWINGS

FIGS. 10A-10E: A) The 4qA BS-converted PCR product is shown (SEQ ID NO: 1). The forward and reverse BSS primer sequences are highlighted. Base pair changes in the BS-converted sequence between the permissive 4A and nonpermissive 4A, 10A, and 10B haplotypes are highlighted. The CpG dinucleotides that would be missing from the analysis in the designated haplotypes are identified by number and are underlined. Y=C or T. B) 4qA BS PCR primers that have undergone freeze-thaw several times produce minor PCR products (*), using DNA from cells lacking permissive 4qA alleles. None of these products correspond to 4qA or 4qB and occasionally correspond to 10qA. C) Output analysis from BISMA comparing a typical 4qA BSS analysis with the rare nonpermissive 10A166 or 4A166 haplotype BSS outputs that may appear, as in B, above. These are readily recognized by the absence of CpGs #16 and 55 (black arrows) and eliminated from analysis. D) The 4qA-L BS-converted PCR product is shown (SEQ ID NO: 2). BSS primers are highlighted (SEQ ID NO: 3). Base pair changes between 4A-L and nonpermissive 4A and 10A haplotypes are highlighted. E) The DUX4 5' BS-converted PCR product (SEQ ID NO: 6). BSS primers are highlighted (SEQ ID NO: 7), with the 4q-specific D4Z4 polymorphism in highlighted in dark gray and the 10q D4Z4 polymorphism highlighted in light gray.

Figure 13:
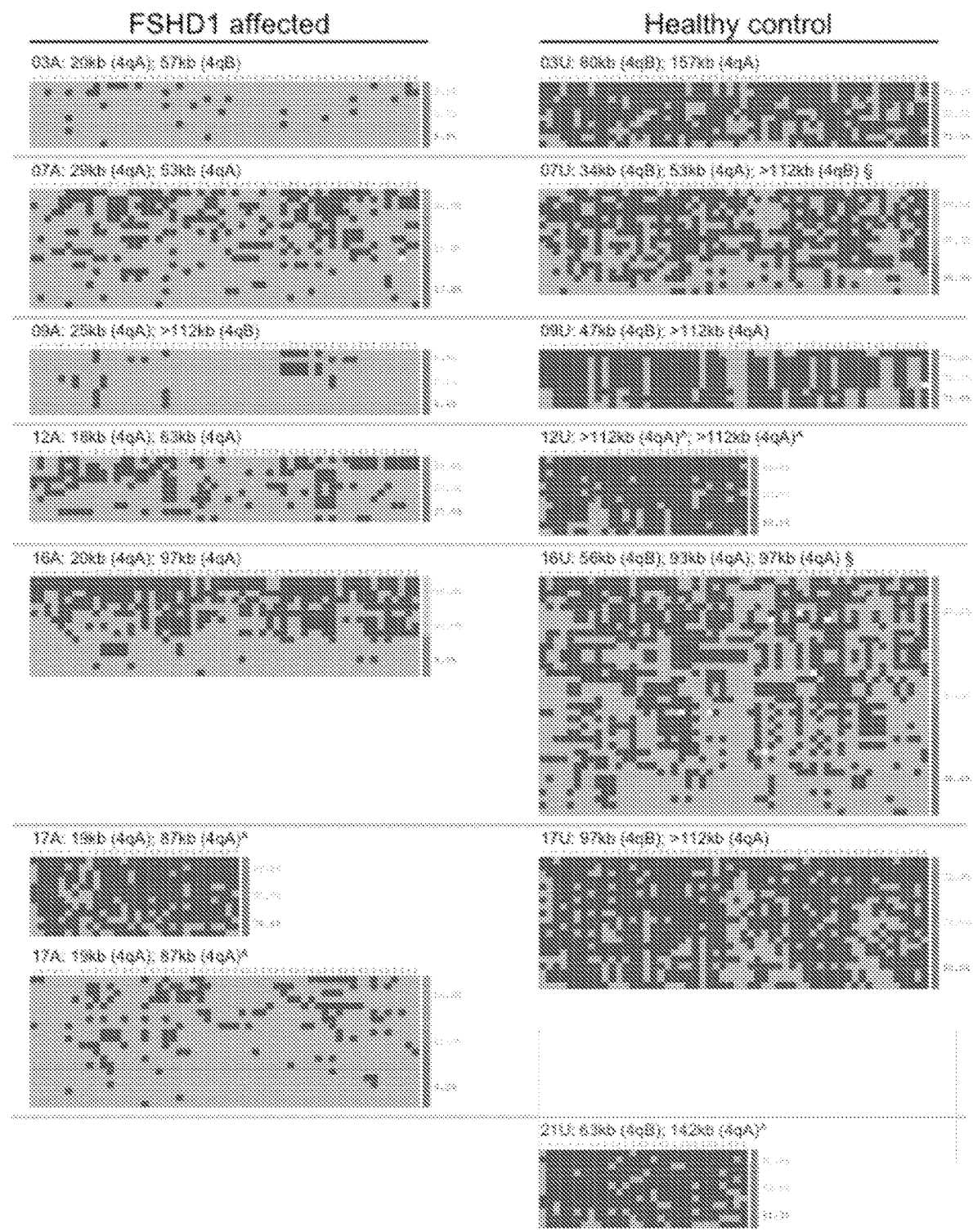
FIG. 13: DNA methylation levels of the distal D4Z4 repeat on the contracted 4qA chromosome correlate with disease. BSS analysis of the distal pathogenic D4Z4 RU in family cohorts of myogenic cells derived from biceps of FSHD1 manifesting (left column) and healthy unaffected (right column) subjects. Overall, 56 predicted CpGs (numbered 1-56) arranged linearly on a chromosome were assayed. Each independent chromosome assayed is from a different individual cell and is represented by a row with each CpG represented by a box, with dark boxes indicating methylation and gray boxes indicating lack of methylation and empty boxes indicating the lack of a CpG detected at that site. Importantly, on average >99% of the predicted CpGs for the 4qA D4Z4 region were identified in the sequences analyzed for each sample, and each total sequence had >90% identity to the reference sequence, indicating that the amplified BSS reactions are specific to 4qA and there are very few DNA polymorphisms. ^17A and 41A were assigned 4qA/A haplotypes by standard genetic testing; however, sequence analysis indicates the BSS assay only amplifies the contracted 4qA allele and the noncontracted allele is nonpermissive. Numbers in the right margin indicate estimated percent methylation for each of two alleles using a beta-binomial mixture model (allele 1 is dark gray, allele 2 is light gray), and using a mono-allelic model. The bar in the right margin indicates confidence in assignment of each sequence to each allele (a blend of dark channel for posterior probability from allele 1 and light channel for posterior probability from allele 2).

FIG. 18: FSHD1-nonmanifesting subjects are distinguished by higher levels of DNA methylation than FSHD1- affected subjects at the 4q/10q D4Z4 5' region. BSS analysis (as described in FIG. 13) of the D4Z4 5' region in family cohorts of myogenic cells (15, 28, 29, and 30) derived from biceps of FSHD1-affected (A) vs. FSHD1-nonmanifesting subjects (B). Overall, 56 CpGs were assayed and ~95-100% of the predicted CpGs for the 4q/10q D4Z4 region were identified in all of the sequences analyzed, indicating that the amplified BSS reactions are specific to 4q and 10q D4Z4 repeats.

Figures 19A, 19B:
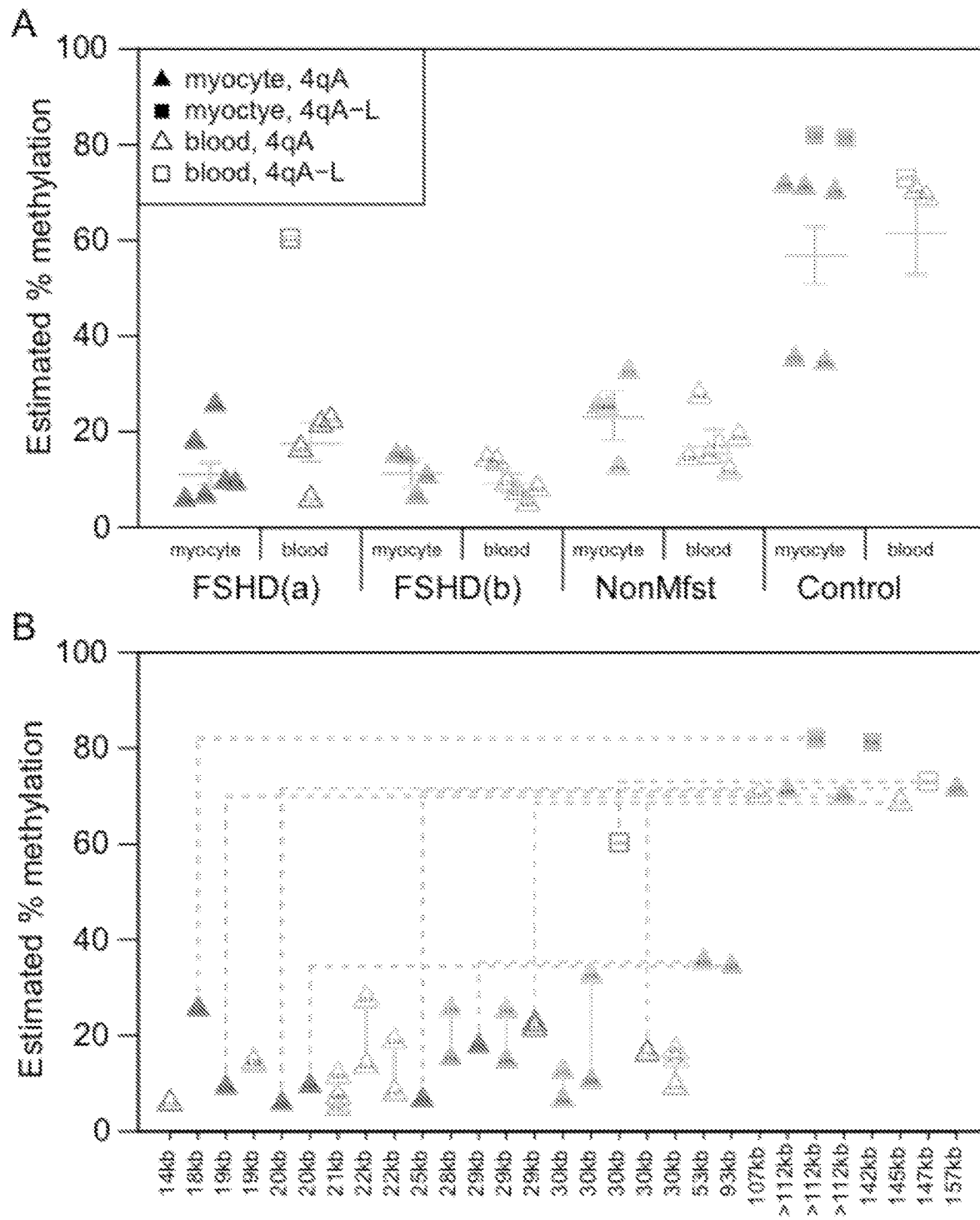

FIGS. 19A-19B: Summary of DNA methylation data. A) A plot of the estimated average DUX4 gene body percent methylation for each sample, using a mixture-model to estimate this value for the 4qA allele with the lesser percent. FSHD affected samples are split into two groups, those with nonmanifesting first-degree relatives in the sample cohort (FSHD(a)) and those without (FSHD(b)). The nonmanifesting samples are labeled NonMfst, and the unaffected control samples are labeled Ctrl. Solid symbols indicate myocyte samples, and empty symbols indicate blood samples. Triangles indicate data from the 4qA assay and squares indicate data from the 4qA-L assay. Each group is subdivided into myocyte and blood subgroups. Within each of the eight subgroups the symbols are ordered by family number. Crosses behind each subgroup indicate means+/−standard errors based on a linear mixed-effect (LME) model with fixed effects for each of these eight subgroups, an additive fixed effect for assay type, and a random effect for family. Means and error bars show estimated fixed effects for 4qA assay; 4qA-L estimates are higher. LME calculations were performed on logit-transformed methylation probabilities, and results were then transformed back to percentages using a logistic transformation (which is why the error bars are not symmetric about the means). B) The same data as in A but with samples ordered by minimum 4qA EcoRI/BlnI length (ordered by family number in case of ties), and with lines connecting related subjects. Solid lines connect FSHD manifesting and nonmanifesting pairs (who have the same minimum 4qA EcoRI/BlnI length), and dashed grey lines connect FSHD affected and control pairs (who do not). Lines are not visible for family 43 (4th column) or 47 (7th column).

Figure 20:
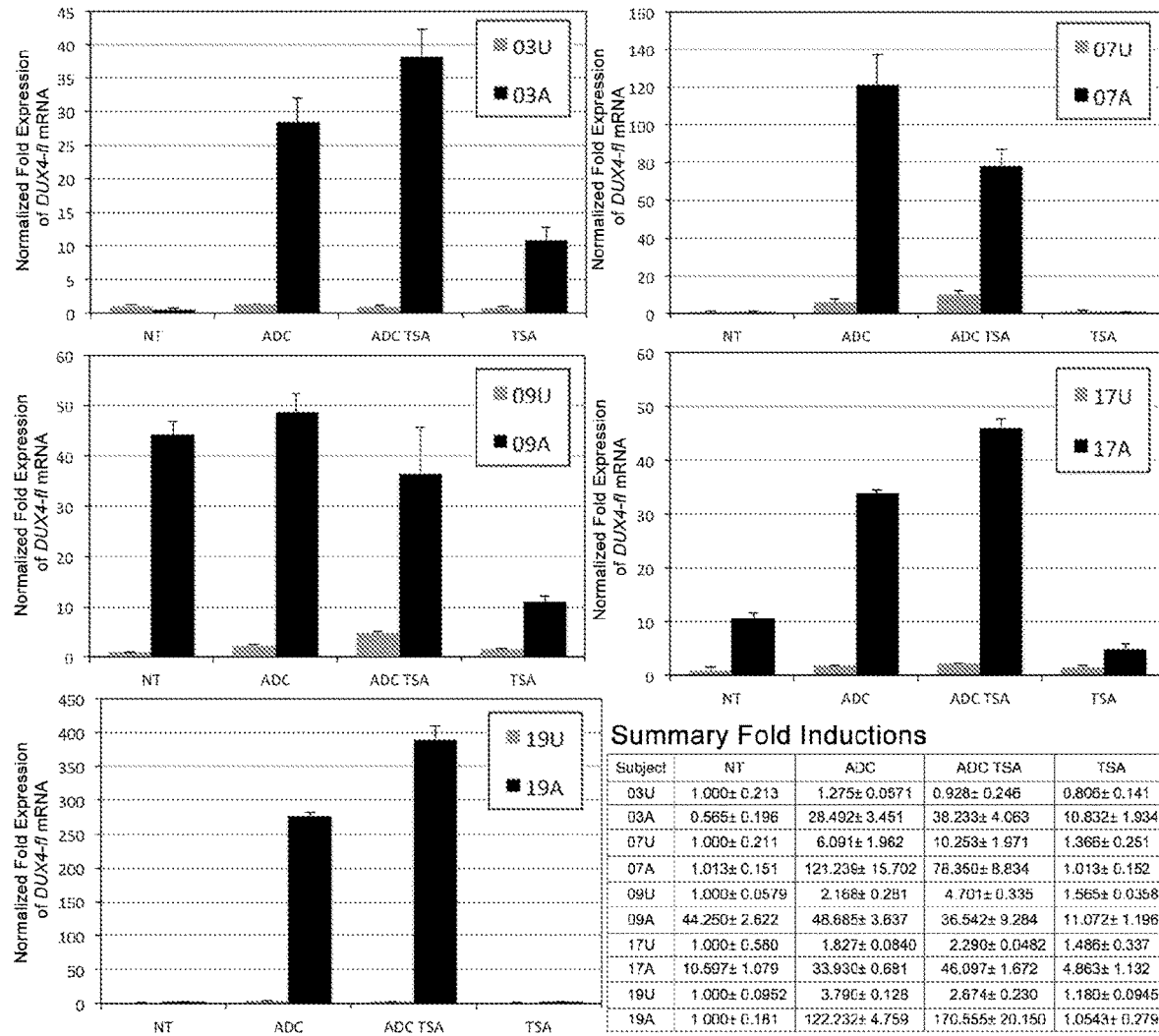

FIG. 20: Myocytes from FSHD1-affected subjects are epigenetically poised to express DUX4-fl. Myocytes from five family cohorts (03, 07, 09, 17, and 19) of clinically affected FSHD1 subjects (A) and healthy first-degree relative controls (U) were treated in parallel with Decitabine (ADC), TSA, ADC+TSA (ADC TSA), or left untreated (NT). DUX4-fl expression was analyzed by qRT-PCR and normalized to levels of 18S RNA. Data are plotted as fold expression relative to the untreated control sample for each cohort and summarized in the table, lower right. All assays were repeated three times and each qRT-PCR was performed in triplicate.

Figure 21:
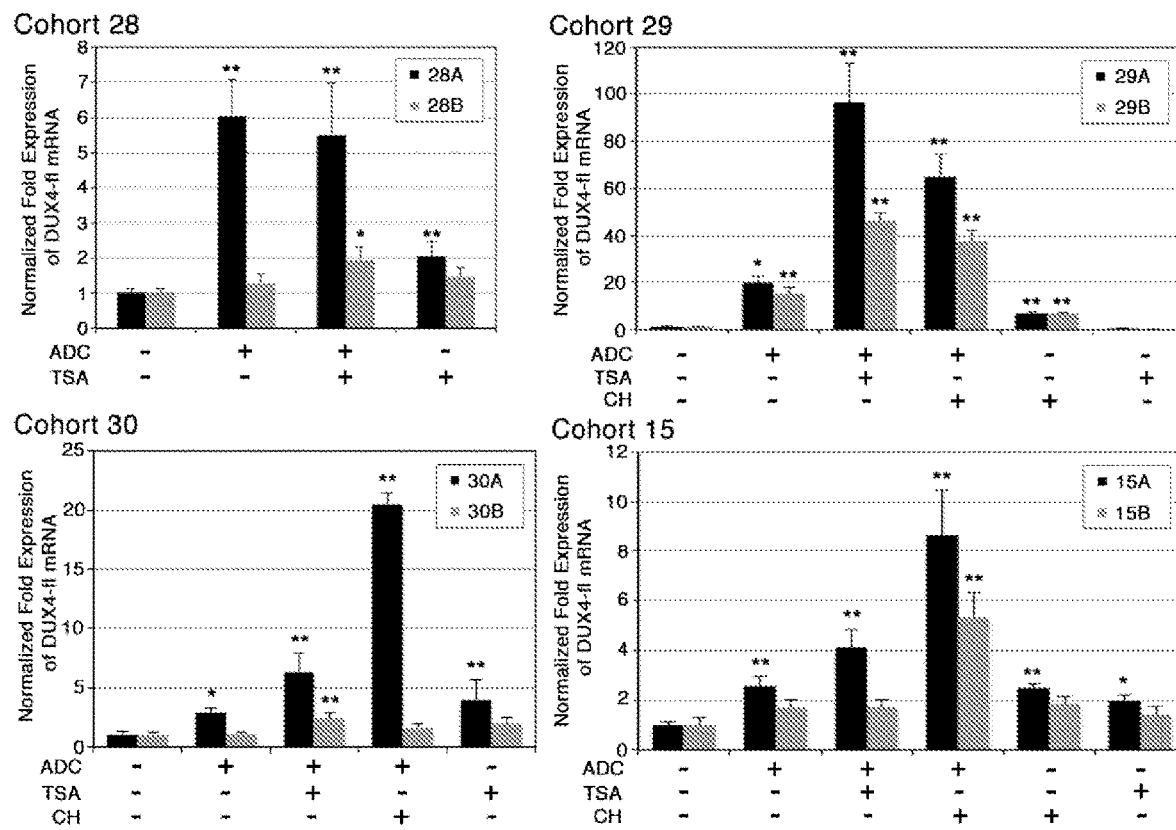

FIG. 21: Myocytes from FSHD1-nonmanifesting subjects are more refractory to expressing DUX4-fl than myocytes from FSHD1-affected relatives. Myocytes from four family cohorts (15, 28, 29, and 30) of FSHD1-affected subjects (black bars, "A" subjects) and FSHD1-nonmanifesting subjects (gray bars, "B" subjects) were treated in parallel with Decitabine (ADC), TSA, chaetocin (CH), or combinations of drug treatments, as indicated. DUX4-fl expression was analyzed by qRT-PCR, normalized to levels of 18S RNA, and plotted as fold expression compared to the untreated samples for each cell strain. Comparisons were made between FSHD1-affected and FSHD1-nonmanifesting for each treatment (* $P<0.05$;  $P<0.01$, * $P<0.001$, Student's t-test). All assays were repeated three times and each qRT-PCR was performed in triplicate.

Figure 22:
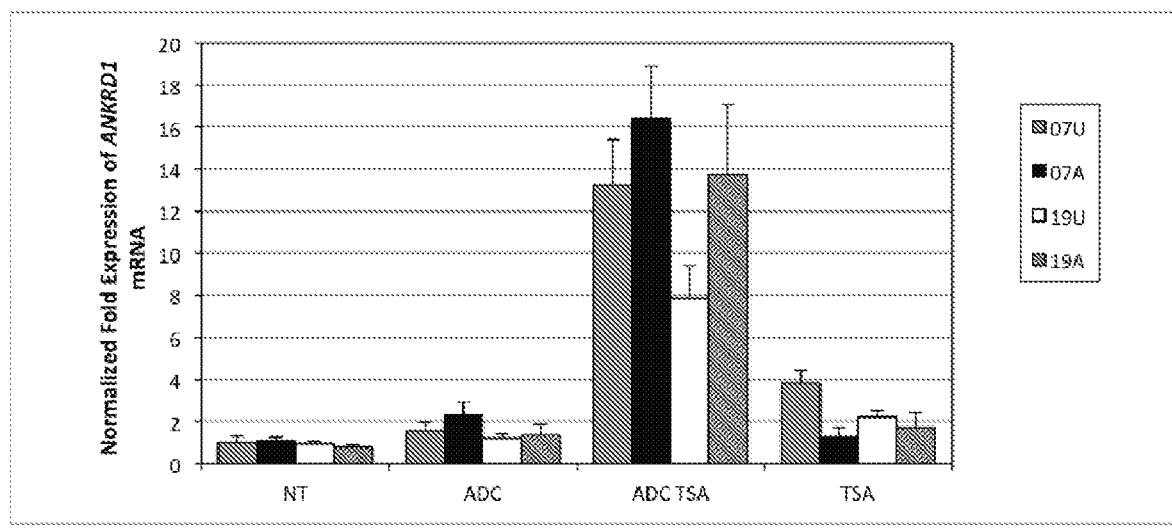

FIG. 22: Drug treatments have similar effects on control gene expression in FSHD1-affected and unaffected myocytes. Two cohorts (07 and 19) that showed the greatest drug-induced DUX4-fl expression were assayed for expression of Ankyrin Repeat Domain 1 (ANKRD1), a gene under epigenetic repression in myocytes. All four cell lines were similarly induced by each treatment with no significant differences between affected (A) and control (U) despite showing 20-fold and 32-fold induction for Decitabine (ADC) treatment and 7.5-fold and 65-fold induction for ADC TSA (cohort 07 and 19, respectively; FIG. 20). Interestingly, the TSA alone treatment induced ANKRD1 expression despite having no effect on DUX4-fl expression in these cohorts.

Figure 23:
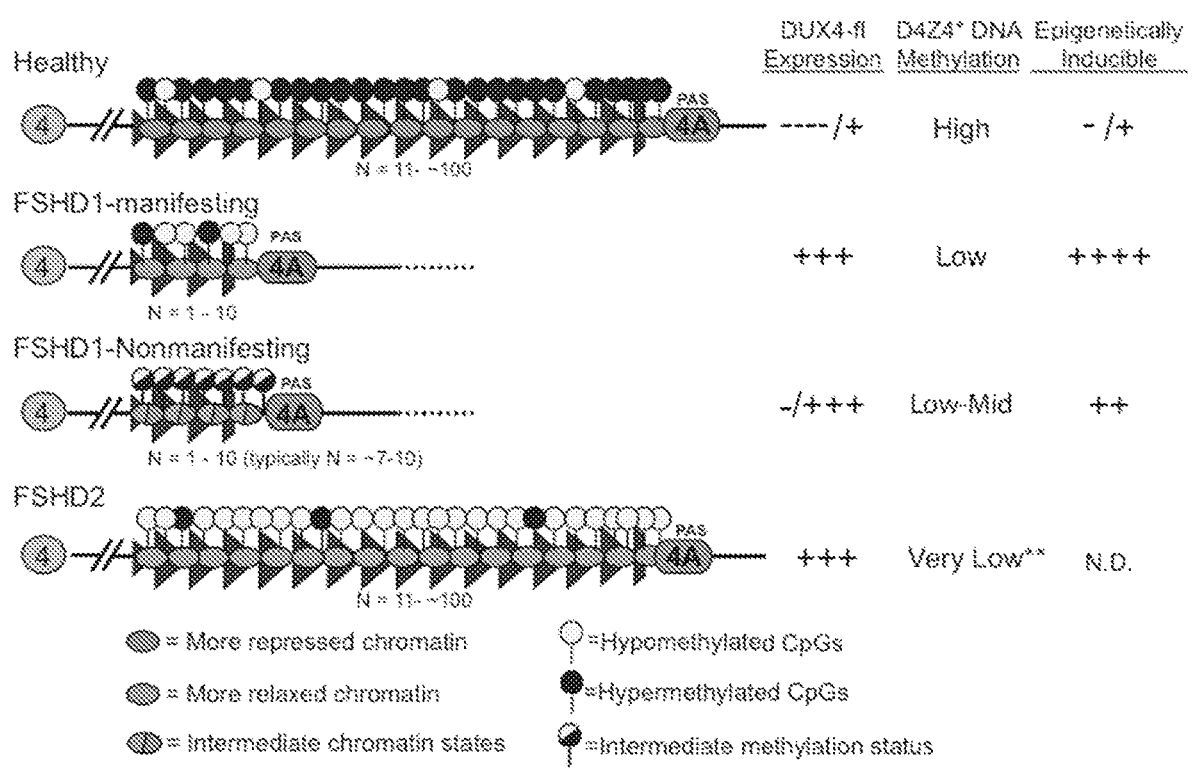

FIG. 23: FSHD1-manifesting, FSHD1-nonmanifesting, FSHD2, and healthy subjects are characterized by distinct states of epigenetic susceptibility to DUX4-fl expression. Model for the different epigenetic states that distinguish healthy vs. FSHD1 vs. nonmanifesting vs. FSHD2 subjects. Healthy, unaffected subjects are characterized by stable repression of the distal pathogenic D4Z4 repeat, as indicated by DNA hypermethylation and chromatin compaction. Cells from these subjects express very low or undetectable levels of DUX4-fl, and are refractory to epigenetic induction of DUX4-fl. Cells from FSHD1-affected subjects display de-repression at the distal pathogenic D4Z4, as indicated by DNA hypomethylation and loss of chromatin compaction. These cells express detectable DUX4-fl, which is further induced upon treatment with epigenetic drugs. Cells from FSHD1-nonmanifesting subjects display an intermediate level of repression at the distal pathogenic D4Z4, as indicated by levels of DNA methylation and DUX4-fl inducibility which fall between those of FSHD1-affected and healthy, unaffected subjects. Despite lacking a contracted D4Z4 allele, cells from FSHD2 subjects are distinguished by severe hypomethylation at D4Z4 arrays, indicating a pronounced de-repression in these regions, which results in detectable expression of DUX4-fl. *For FSHD1, only the contracted 4q D4Z4 is hypomethylated; **For FSHD2, both 4q and 10q D4Z4 arrays are hypomethylated. Refer to text for more details.

Figure 24:
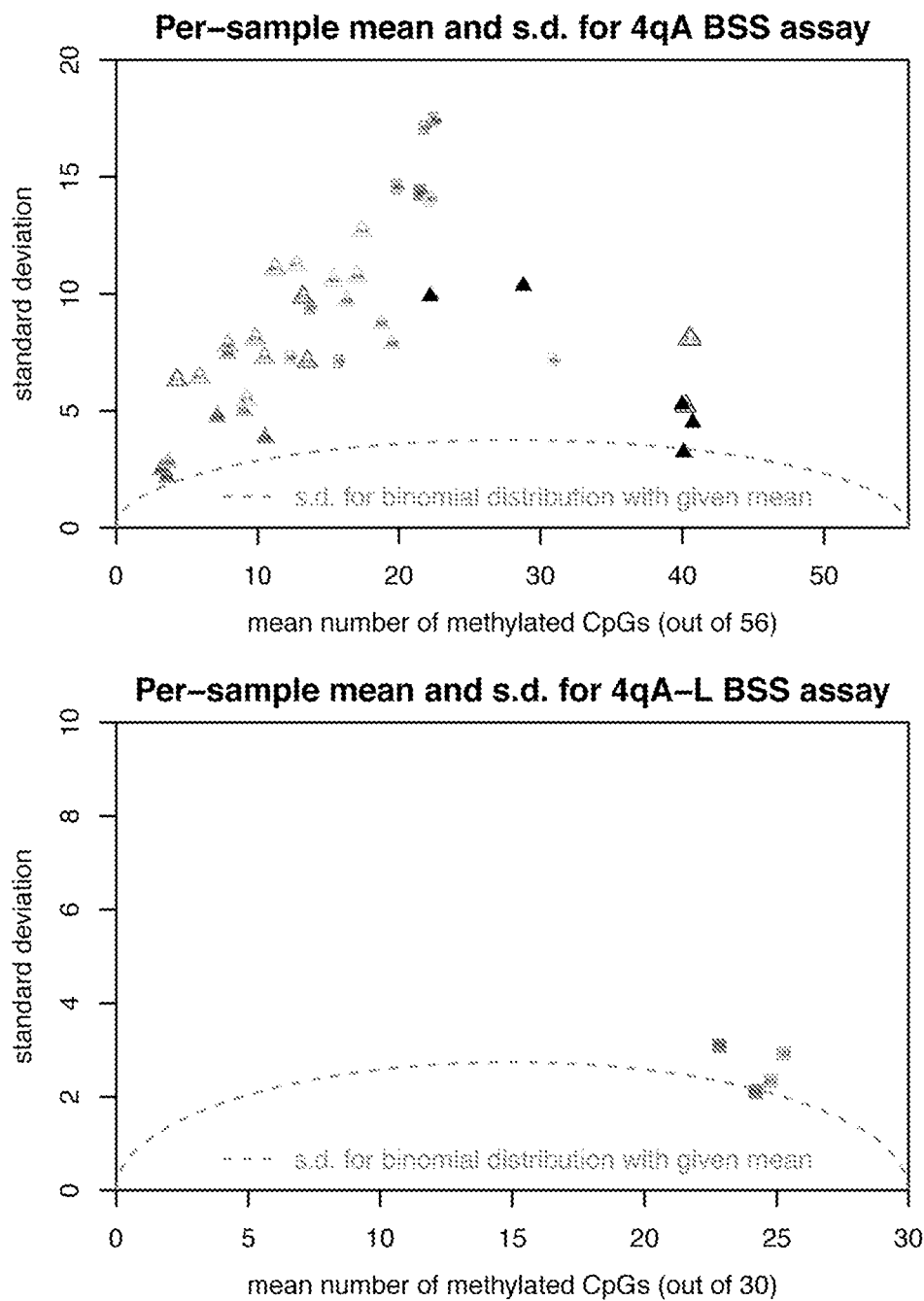

FIG. 24: Within-sample variability in the number of methylated CpGs in the DUX4 gene body is greater than expected for a binomial distribution. The observed mean and standard deviation in the number of methylated CpGs, out of N=56 total for 4qA assay (above) and N=30 total for the 4qA-L assay (below), for different BSS sequences is shown for each sample. (For this figure the rare sequences with missing CpG data at one or more site were excluded.) Points are coded by disease group: mid-grey for FSHD1 subjects with nonmanifesting relatives in the sample cohort, dark grey for the other FSHD1 subjects, light grey for nonmanifesting subjects, black for healthy controls. Solid symbols indicate myocyte samples, and empty symbols indicate blood samples. For the 4qA assay, triangles indicate genotypes with exactly one amplified 4qA allele (allele without ˆ or ˆˆ in Table 3), and circles indicate samples that have more than one amplified 4qA; for the latter group, but not the former, part of the overdispersion may be attributed to methylation differences between alleles. For the 4qA-L assay, squares indicate genotypes with exactly one 4qA-L allele, which happens to account for all points. The standard deviation for a binomial distribution with given mean and N is indicated by the dashed line. The observed overdispersion relative to a binomial distribution, even for samples with a single amplified 4qA allele, motivates the use of a more flexible beta binomial distribution to model allele-specific methylation.

Figure 25:
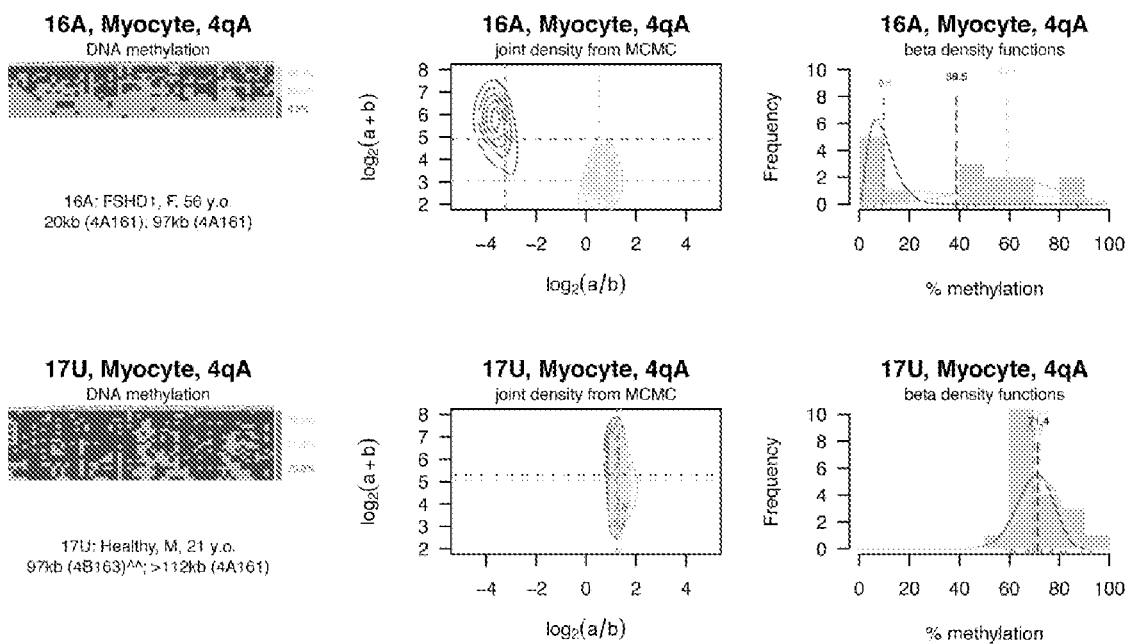

FIG. 25: Beta-binomial mixture model for the 4qA BSS assay. Plots of beta-binomial mixture model of DNA methylation for 4qA BSS assay in myogenic cells from sample 16A (top) and 17U (bottom). Each row has three panels: (Left) Grids show per-site CpG methylation for each bisulfite-sequenced clone (dark gray=methylated; light gray=not methylated), with clones sorted from highest percent methylation to lowest. Numbers in the right margin indicate estimated percent methylation for each of two alleles using a beta-binomial mixture model (allele 1 is dark, allele 2 is light), and using a single allele model (black). The bar in the right margin indicates confidence in assignment of each sequence to each allele (a blend of dark gray channel for posterior probability from allele 1 and light gray channel for posterior probability from allele 2). (Center) Contours of joint posterior probability density of parameters $r_i=\log(a_i/b_i)$ and $\log(s_i)=\log(a_i+b_i)$ for i=1 (dark gray) and i=2 (light gray) constructed from MCMC samples of mixture model. (Right) Histogram of observed methylation percentages for clones, with actual data points indicated by tick marks (jittered slightly to avoid overlap). Probability density functions for beta components of beta-binomial mixture model (using posterior mean estimates of $r_i$ and $s_i$) are overlaid in dark gray (i=1) and light gray (i=2); probability density functions for beta component of single allele beta-binomial model is shown in black.

Figure 26:
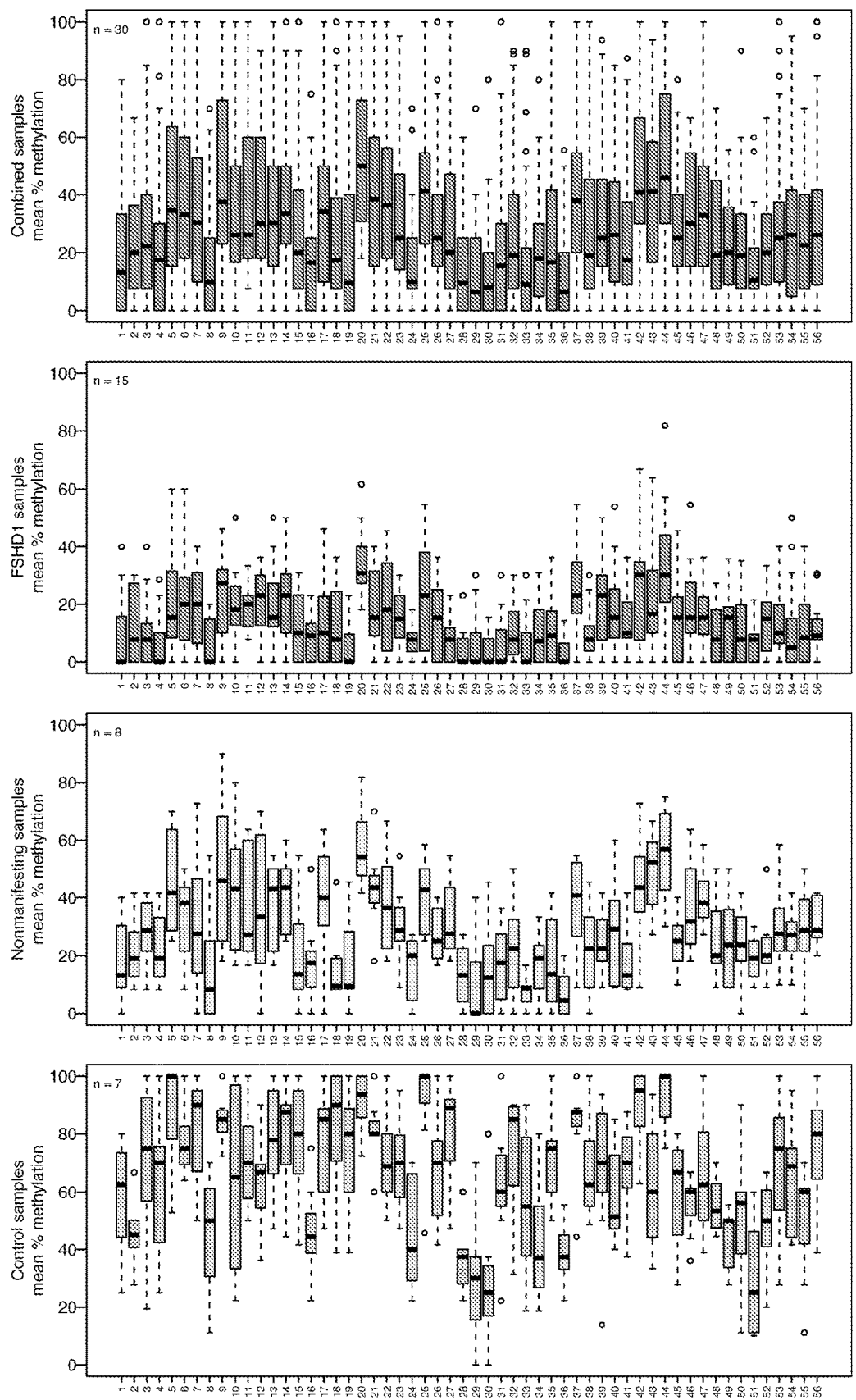

FIG. 26: CpG methylation probabilities vary across the sequence in the 4qA BSS assay. For each sample, the mean methylation percent at each of the 56 CpG sites was computed. These boxplots summarize the distribution of these per-site averages for different samples (bands indicate medians, and boxes extend from first quartile to third quartile). To sidestep complications due to mixtures of 4qA alleles, for these plots only those samples with a single amplified 4qA allele are included (alleles with ^ or ^^ symbol in Table 3 are not amplified). The upper plot shows 30 samples combined; the three other plots separate these samples into FSHD-affected (15 samples, combining what are elsewhere separated into FSHD(a) and FSHD(b)), nonmanifesting (8 samples) and healthy control (7 samples).

DETAILED DESCRIPTION OF THE INVENTION

A description of example embodiments of the invention follows.

Example 1

Figure 1:
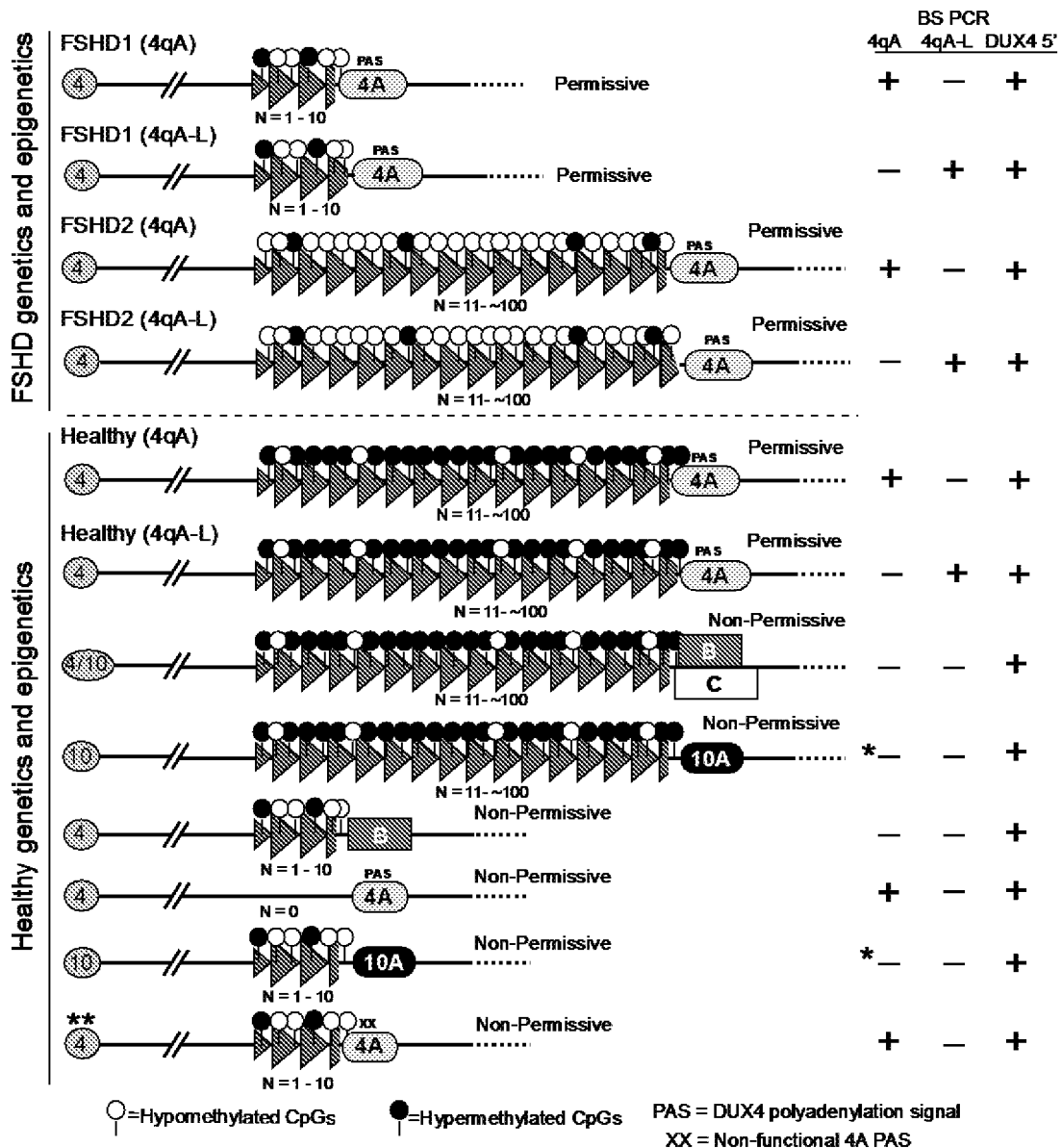
FIG. 1: The molecular signatures of FSHD are complex, as illustrated by healthy and FSHD-type chromosomes. In the general healthy population, each chromosome 4q arm has a large polymorphic array of D4Z4 repeats containing more than 10 RUs. In FSHD1, there is a dominant contraction of one 4q array to between 1 and 10 D4Z4 repeat units, whereas FSHD2 is contraction-independent. There are two main allelic variants in the subtelomere distal to the array, termed A and B. A rare third classification of subtelomere, termed C, is used for subtelomeres that do not hybridize with probes for A or B due to distal sequence changes [18]. In some instances, the distal-most repeat fragment of the 4q D4Z4 array contains additional ~2 kb of D4Z4 sequence, resulting in a longer terminal RU in cis with a 4qA subtelomere; this type of 4qA allele is referred to as 4qA-L [15]. Both FSHD1 and FSHD2 are exclusively linked to the 4qA subtelomere allelic variants containing a PAS for the DUX4-fl mRNA [12, 15]. In addition, both FSHD1 and FSHD2 require the epigenetic disruption of the D4Z4 array to a less methylated and more relaxed chromatin state. Results of the described BSS assays are indicated by "+" if a BS PCR product is produced and "−" if no BS PCR product is produced. *On rare occasions due to primer degradation a 10qA BS PCR product is detected; however sequencing eliminates these from analysis. **Diagnosis of this healthy chromosome requires genomic PCR and sequencing of the 4qA subtelomere to identify a non-permissive 4qA PAS.
Figures 2A, 2B, 2C:
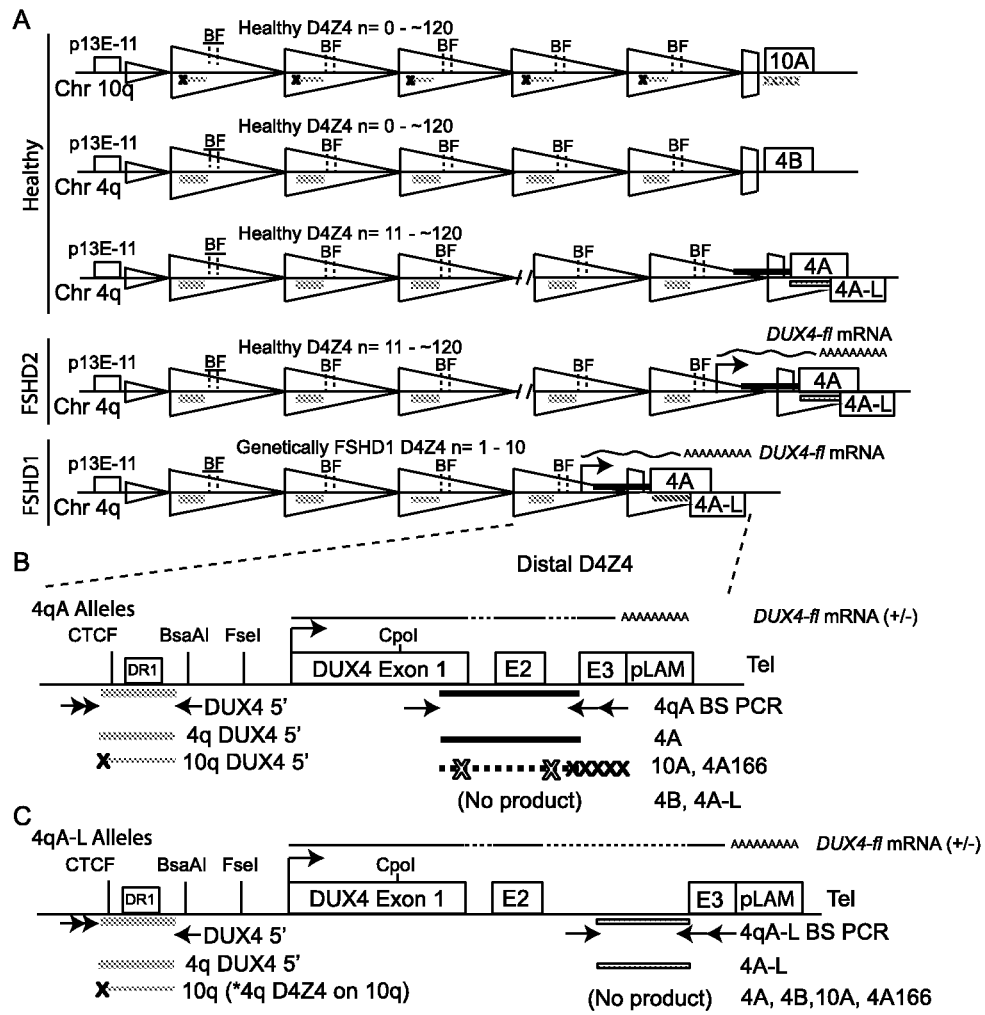
FIGS. 2A-2C: Schematic for BSS analysis of FSHD-associated 4qA chromosomes and 4q D4Z4 repeat units. A) Cartoon depicting the location of BS PCR products for the 4qA BSS assay (black), the 4qA-L BSS assay (black outline) and the DUX4 5' BSS assay (gray). For the DUX4 5' reaction, the nested primer has a preference for a 4q D4Z4 polymorphism ("x"); however, a fraction of D4Z4 units are amplified from chromosome 10q arrays (denoted by thin gray lines), (*) including chromosome 4q-type D4Z4 units present on chromosome 10q due to trans chromosomal rearrangements found in ~6% of subjects [18]. The proximal BsaAI (B) and FseI (F) methylation sensitive restriction enzyme sites analyzed by the southern blotting technique are indicated by underlining. B and C) Diagrams of the distal-most D4Z4 repeat that produces the polyadenylated DUX4-fl mRNA and is analyzed in the (B) 4qA BSS assay and (C) 4qA-L BSS assay. Arrows indicate BS PCR primers and "X"s indicate sequence differences with 4qA; rare 10qA products amplified in the absence of 4qA alleles and due to primer degradation are detected and eliminated from analysis by specific sequence polymorphisms (FIGS. 10A-10E). Neither 4q BSS assay amplifies the 4qB allelic variant.
Figure 3:
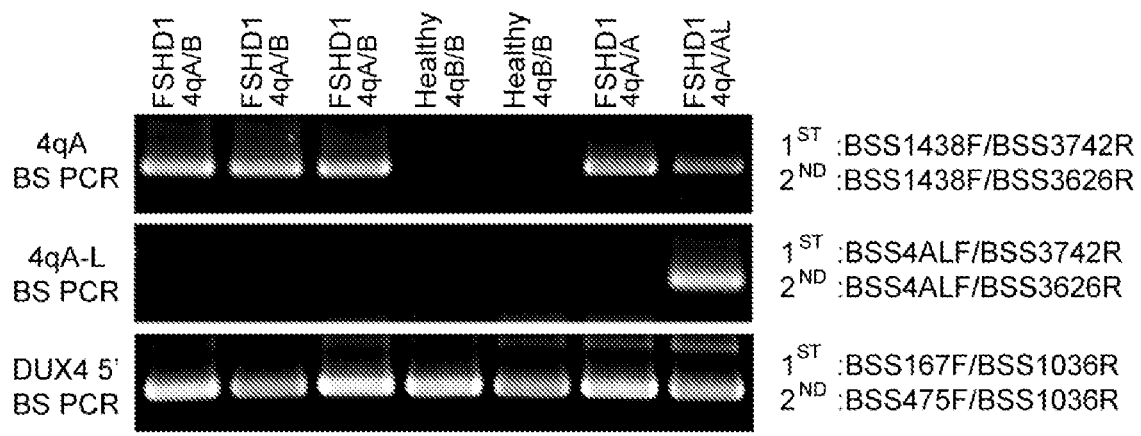
FIG. 3: BS PCRs using genomic DNAs from subjects with a range of 4q allelic combinations show the specificity of the three BSS assays. Nested PCRs were performed using bisulfite converted genomic DNAs from seven subjects, five FSHD1 and 2 healthy, with varying 4q haplotypes (4qA/A, 4qA/B, 4qB/B and 4qA/A-L, as indicated). The primer sets used are indicated to the right of each panel. The 4qA BS PCR (upper panel) amplified a product from all five subjects that contain at least 1 4qA allele and did not amplify any detectable product from the two subjects lacking a 4qA allele. The 4qA-L BS PCR (middle panel) only amplified a product from the one subject that possessed a 4qA-L allele. The DUX4 5' BS PCR (lower panel) amplified a product from all seven subjects. The identities of all BS PCR products were confirmed by sequencing.

Results and Discussion
Development of a Combined Distal 4qA-Specific and 4q/10q 5' D4Z4 DNA Methylation Assay Dramatic epigenetic differences at the 4q35 D4Z4 repeat array between healthy and disease states distinguish FSHD1 and FSHD2 from unaffected individuals. Epigenetic differences at the non-contracted 4q35 D4Z4 and the 10q26 D4Z4 arrays distinguish FSHD2 from FSHD1 and other myopathies. In all forms of FSHD, it is the distal 4q35 D4Z4 in cis with a disease permissive 4A subtelomere that produces the pathogenic DUX4-flmRNA [15]. However, this pathogenic D4Z4 repeat has never been specifically analyzed in FSHD1 or FSHD2 [17, 19, 20, 29]. Therefore, in order to study epigenetic changes at the disease-relevant D4Z4 repeat, we developed two BSS assays that specifically analyze the distal 4qA or 4qA-L associated D4Z4 RU (FIGS. 2A-2C). Utilizing polymorphisms in the BSS PCR primers that are exclusive to the disease-permissive 4A subtelomere and not found in 10A, the 4qA BSS assay analyzes the DNA methylation status of 56 CpGs (FIG. 10A) in the distal D4Z4 RU in cis with a 4A subtelomere (FIG. 2B). The 4qA BS-PCR product is amplified from all bisulfite-converted genomic DNAs from subjects possessing at least one 4qA allele (FIG. 3, upper panel). The D4Z4-4A fragments were sequenced and, importantly, all 56 CpGs predicted by the reference sequence were accounted for in >90% of the analyzed sequences from these clones, confirming the specificity of the reaction for the distal 4qA-derived D4Z4. The 4qA-L BSS assay utilizes the same 4A subtelomere-specific reverse BS PCR primers as above; however, these are paired with a 4qA-L-specific forward BS PCR primer. The 4qA-L BSS assay analyzes the DNA methylation status of 30 CpGs (FIG. 10D) in the distal D4Z4 repeat on 4qA-L chromosomes (FIG. 2C). The 4qA-L BS PCR product was amplified exclusively from bisulfite-converted genomic DNAs from the one subject possessing a 4qA-L allele and not from any of the six subjects lacking a 4qA-L allele (FIG. 3, middle panel). The 4qA-L fragment was sequenced and all 30 CpGs predicted by the reference sequence were accounted for in 100% of the analyzed sequences from these clones, confirming the specificity of the reaction for the distal 4qA-L-derived D4Z4. Neither the 4qA BS PCR nor the 4qA-L BS PCR produced a product from genomic DNAs isolated from either of the two healthy subjects with 4qB/B haplotypes. It is worth noting that due to the 4qA-specific SNPs residing at the 3'end of the 4qA BS PCR oligonucleotide primers, multiple rounds of primer freeze-thaw, which leads to partial primer degradation, results in a loss of specificity and a consequent amplification of minor products from genomic DNAs lacking the 4qA allele (* FIG. 10B). Sequence analysis of these rare amplicons from 4qB/B samples identified them as either a 10qA product (FIG. 10C) or a non-specific product not derived from any D4Z4 or 4qA/B allelic variant. In addition, since the BSS analysis is sequence-based and not product-based (as in qPCR or Southern blotting), any rare non-specific or 10qA amplifications present are easily identified and removed from the analysis. We conclude that these assay conditions amplify the distal D4Z4 sequence from 4qA chromosomes or 4qA-L chromosomes, depending on the assay, and neither assay amplifies 10A or 4B subtelomere-containing chromosomes.

To complement the distal D4Z4 methylation analysis and provide the context for both 4q35 D4Z4 arrays that is important for the determination of FSHD2 status, we designed a third BSS analysis upstream of the DUX4 open reading frame (referred to as the DUX4 5' BSS assay). This assay analyzes the methylation status of 59 CpGs preferentially in 4q35 D4Z4 RUs but also in 10q35 D4Z4 RUs (FIGS. 2A-2C and 10E). This DUX4 5' region can be amplified from all 4q35 and 10q26 D4Z4 RUs, does not amplify homologous D4Z4s elsewhere in the genome [30], and encompasses a putative CTCF binding site and the DR1 region found to be hypomethylated in all 4q and 10q D4Z4 RUs in FSHD2 cells [29, 31]. As anticipated, all seven of the bisulfite-converted genomic DNAs were successfully amplified using this protocol (FIG. 3, lower panel), validating the integrity of the bisulfite-converted DNAs from the two healthy subjects. Analysis of the DUX4 5' BSS products revealed that all 59 of the CpGs predicted by the reference sequence were accounted for in all sequences in this assay, confirming that these sequences were derived from 4q/10q D4Z4 RUs, which characteristically have very few polymorphisms, and not from homologous D4Z4s located elsewhere in the genome that contain numerous sequence polymorphisms [30]. Thus, combining the DUX4 5' BSS and 4qA/4qA-L BSS assays provides a detailed analysis of the DNA methylation status of the pathogenic distal 4qA D4Z4 RU in the context of overall 4q/10q D4Z4 DNA methylation.

Characterization of Healthy and FSHD1 DNA Methylation Patterns in the Distal D4Z4 Repeat Unit Using Blood and Saliva Epigenetic marks often show tissue specificity; thus, it is very important to carefully examine and compare each locus of interest when performing epigenetic studies on genomic DNAs isolated from different tissue sources [32]. Since FSHD is a myopathy and the pathogenic DUX4 mRNA is expressed predominantly in skeletal muscle [1, 33], the epigenetic status of myocytes is of particular interest. However, muscle biopsies require participants to visit a hospital or clinic, and can be expensive, painful, and difficult to obtain from FSHD patients of any age already exhibiting muscle atrophy. Fortunately, in FSHD1 and FSHD2, the DNA methylation status of the 4q35 D4Z4 is similar between PBMCs and myogenic cells [17]. For example, in FSHD1, the proximal repeats of the D4Z4 array on the contracted 4q35 allele are significantly hypomethylated in both PBMCs and myogenic cells compared to the non-contracted allele or healthy controls [17]. In order to assess the DNA methylation status of the pathogenic distal 4q35 D4Z4 repeat, we used our 4qA and 4qA-L BSS assays to analyze the distal D4Z4 in PBMCs from FSHD1 patients and healthy first-degree relatives. In addition, we are interested in analyzing the epigenetic signatures of large numbers of family members over time, including healthy individuals, some of whom may be identified as potential asymptomatic carriers. Therefore, in addition to testing our assay on genomic DNA isolated from PBMCs, we performed our analysis on saliva samples obtained from the same subjects for a comparison. The advantage of saliva samples is that they can be collected without additional help, there is no needle injection, and collection kits can be mailed to subjects who have undergone informed consent, with the stable 2 ml sample returned by standard mail. This type of testing would be particularly useful for children and in communities or countries where access to a phlebotomist is limiting or relatively expensive and/or standard genetic testing by PFGE or molecular combing is cost-prohibitive or unavailable.

Figures 4A, 4B:
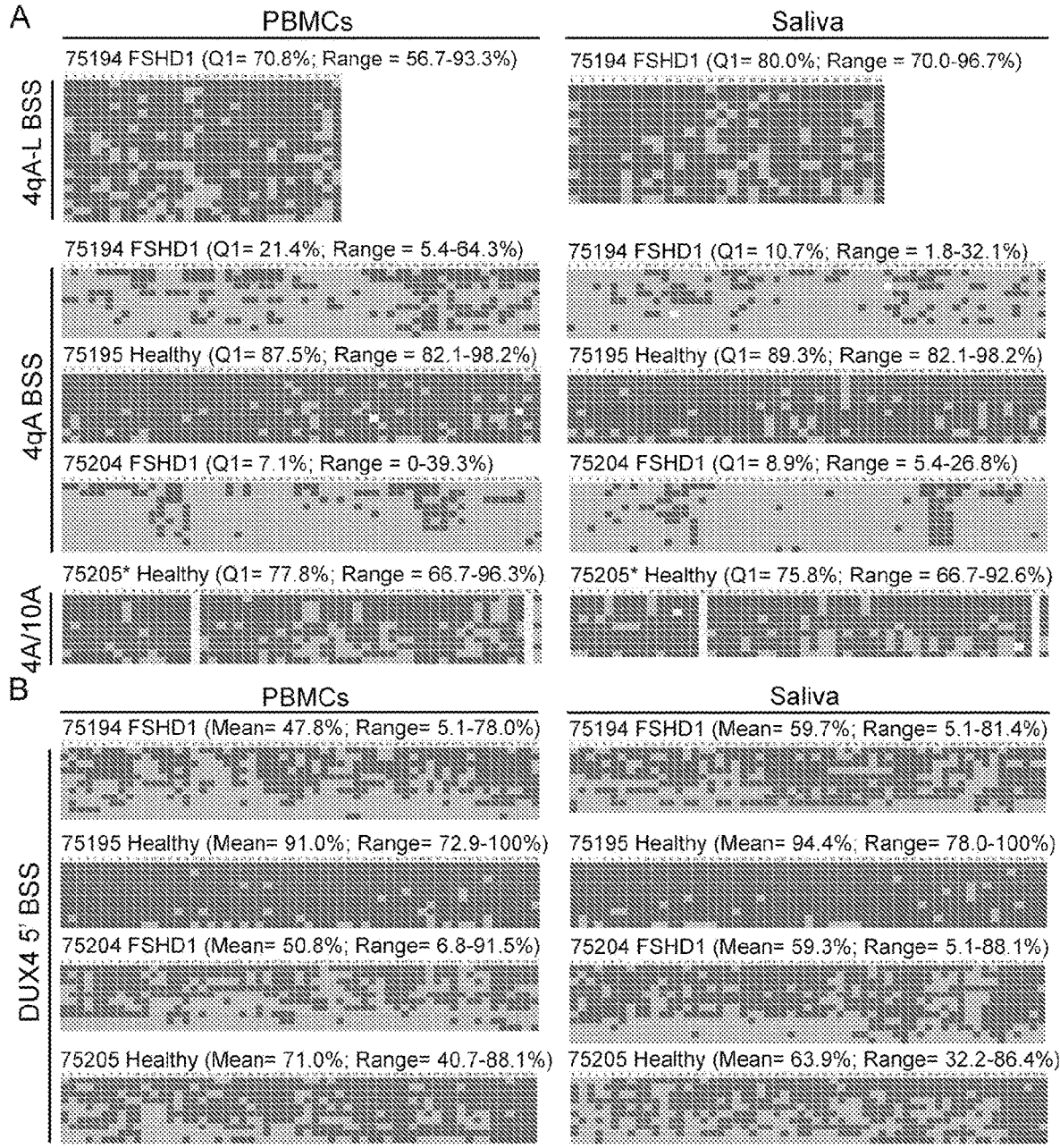
FIGS. 4A-4B: BSS analysis identifies distinct epigenetic signatures for FSHD1 and healthy controls that are similar between genomic DNA samples isolated from blood and saliva. Genomic DNAs isolated from PBMCs or saliva from the same four subjects were analyzed using the A) 4qA BSS assay and 4qA-L BSS assay and B) the DUX4 5' assay. Expected CpGs, based on predicted sequence composition of the unconverted region amplified, are listed in numerical order. Dark gray boxes indicate methylated CpGs, light gray boxes indicate unmethylated CpGs, and white boxes indicate no CpG at the expected site. The DNA methylation is reported (A) for the Q1 and (B) the mean methylation, along with the range from the lowest % methylation to the highest % methylation in the set. * Neither the 4qA BS PCR nor the 4qA-L BS PCR produced a product from this subject, indicating that no 4qA or 4qA-L alleles were present; therefore, an alternative BSS protocol that amplifies both 4qA and 10qA alleles was performed (see methods). The white boxes indicate no CpGs were detected at positions #16 and #55, which suggested these sequences were derived from 10qA. However, analysis of the complete BSS sequence data provided an additional non-CpG polymorphism that identified all sequences as being derived from 4C166H chromosomes.

A blind comparison of DNA methylation profiles using the three BSS protocols was performed on genomic DNAs isolated from blood and saliva from two clinically diagnosed and genetically confirmed FSHD1 subjects and two healthy first-degree relatives (FIGS. 4A-4B). The assays analyzed all 56 CpGs in the distal D4Z4 of each 4qA array, all 30 CpGs in the distal D4Z4 of 4qA-L linked arrays, when present, and 59 CpGs in the DUX4 5' region of all samples, as described above (FIGS. 2A-2C). All FSHD subjects will possess at least one 4qA (or 4qA-L) allele, and non-FSHD control subjects either have two, one, or no 4qA (or 4qA-L) alleles. Healthy control subjects with either one or two 4qA/4qA-L alleles are predicted to show DNA hypermethylation (>35% methylation) on all assayed chromosomes, whereas those with 4qB/B genotypes will not produce a BS PCR product or in some rare instances produce a 10qA product that is effectively removed from analysis by identifying sequence polymorphisms. FSHD1 subjects must have at least one 4qA allele in cis with a contracted D4Z4. In FSHD1 subjects with 4qA/B haplotypes, all of the analyzed chromosomes are derived from the contracted D4Z4 array and are expected to show hypomethylation. In FSHD1 subjects with 4qA/A or 4qA-L/A-L haplotypes, on average half of the analyzed chromosomes will be derived from the contracted array and are expected to show DNA hypomethylation while the other half will be derived from the non-contracted array and are expected to show hypermethylation. In subjects with 4qA/A-L haplotypes, all of the BSS clones in each assay will be derived from the same chromosome, either contracted or non-contracted.

To avoid diluting the signature of FSHD1 by averaging with the methylation levels of the non-contracted array, we use the $1^{st}$ quartile (Q1) of the methylation percent of all analyzed chromosomes as a summary statistic. This corresponds to dividing all sequences into two groups based on methylation percentage, and taking the median value of only those sequences in the lower group. (If the total number of sequences is odd, there is the issue of whether to include the central sequence in the lower group or not before taking the median; to give it half weight we compute the median both ways, then take the arithmetic average; this corresponds to the R function quantiles with type=5.)

In a 4qA/A FSHD1 subject for whom all chromosomes with the contracted array have lower 4qA BSS methylation than any chromosomes with the non-contracted array, Q1 gives an estimate of the median 4qA methylation of just the contracted array. (With n=10 sequences analyzed, there is a 5.4% chance that more than ¾ will arise from the non-contracted allele due to random sampling, so Q1 will not be an accurate reflection of the contracted allele; increasing n to 18 reduces the probability of this sort of failure to 1.5%.)

Note, however, that if there is any overlap in methylation levels between alleles (as may be expected in healthy controls, FSHD2 subjects, and potentially some FSHD1 subjects as well) then the half of analyzed sequences with lower methylation need not arise from a single allele, and Q1 underestimates the median methylation of any one allele. In the extreme case of no difference in methylation distributions between two 4qA alleles, or of 4qA/4qB genotypes (in which all sequences arise from a single allele), Q1 instead is an estimate of the lower quartile of methylation of one allele, rather than the median. This bias is tolerable for the present application, so for simplicity we use Q1 (Table 2) as a summary statistic uniformly for all samples, without requiring the genotype to be known; we have also developed a mixture-model based statistical approach that aims to mitigate this bias (T. Jones et al. 2014, unpublished observations).

As shown in FIG. 4A and Table 2, the distal 4qA D4Z4 was dramatically hypomethylated in both blood and saliva samples for subjects 75194 (Q1=21.4% methylated, PBMCs; Q1=10.7% methylated, saliva) and 75204 (Q1=7.1% methylated, PBMCs; Q1=8.9% methylated, saliva), and was hypermethylated in both blood and saliva of subject 75195 (Q1=87.5% methylated, PBMCs; Q1=89.3% methylated, saliva). The 4qA-L BSS analysis indicated that the A-L haplotype was only present in subject 75194 and this allele was hypermethylated (Q1=70.8% methylated, PBMCs; Q1=80.0% methylated, saliva). Neither of these 4qA-specific BS PCRs produced a product from either the PBMCs or saliva of subject 75205, indicating that this subject lacked any 4qA alleles. Based on this analysis we predicted that subjects 75194 and 75204 were FSHD patients, and subjects 75195 and 75205 were healthy controls.

Figures 5A, 5B:
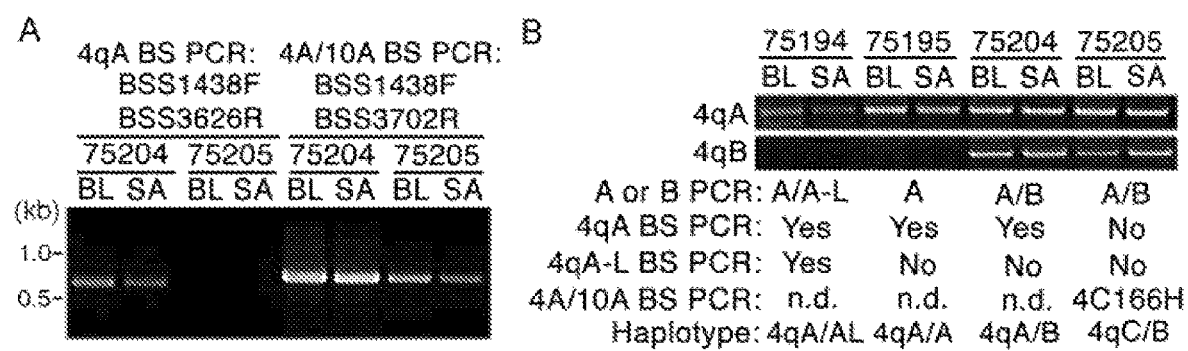
FIGS. 5A-5B: PCR haplotyping. A) BS PCR products for subjects 75204 and 75205 using the 4qA BSS primer set (left) or a primer set that non-specifically amplifies both 4qA and 10qA. BL: blood (PBMCs) and SA: saliva. B) Genomic PCR amplification for either the 4qA or 4qB subtelomeres [15], as indicated. Although the 4qA D4Z4 gene body BS PCR did not produce a product for subject 75205 (No), standard PCR for 4qA alleles did produce a PCR product (*). These products were sequenced and confirmed as being 4C166H. These data together indicate that subject 75205 has a 4qB/C166H genotype. Additional predicted genotypes are indicated.

To further investigate the BSS results, we performed a second BS PCR on DNAs from subjects 75204 and 75205 utilizing a BS PCR primer set (primers BSS1438F and BSS3702R) that amplifies the distal D4Z4 region from both 4qA and 10qA for nested PCR (FIG. 5A). The BSS profile of the 75205 products from both saliva and PBMCs showed no 4qA or 4qA-L chromosomes and suggested amplification of 10qA (FIG. 4A, 4A/10A row), as indicated by the lack of CpGs #16 and #55 (typically a 10A166 haplotype BSS signature). However, analysis of the entire amplified sequence revealed a polymorphism in all products that, when combined with the methyl-CpG profile, corresponded to the non-permissive 4C166H haplotype [18]. To confirm the haplotypes predicted by the BSS, genomic PCR was performed on all DNA samples to detect the presence of 4qA, 4qA-L, and 4qB subtelomeres (FIG. 5B), as described [15]. As suggested by the BSS results in FIG. 4A, subjects 75194, 75195, and 75204 all contained at least one 4qA allele and subject 75194 also contained one 4qA-L allele. Subjects 75204 and 75205 each tested positive for a 4qB allele. Interestingly, subject 75205 also tested positive for a 4qA allele from both PBMC and saliva DNAs despite producing no 4qA BS PCR product (FIG. 5B), indicating that this 4qA haplotyping PCR also amplifies 4qC chromosomes. Sequence analysis of the genomic PCR products confirmed that subject 75205 has one chromosome with a 4C166H haplotype, consistent with the BSS data (FIG. 4A), further supporting the specificity of the 4qA BSS assay. This more complete analysis supports our initial conclusions and provides additional information as follows: subjects 75194 (4qA/A-L) and 75204 (4qA/B) were FSHD patients and subjects 75195 (4qA/A) and 75205 (4qB/4C166H) were healthy controls.

BSS analysis of the DUX4 5' promoter region is more complex (FIGS. 2A-2C). This analysis was designed to preferentially detect all 4q D4Z4s regardless of haplotype from both the contracted and non-contracted 4q chromosome arrays. Because in FSHD1 only the contracted chromosome 4 D4Z4 is hypomethylated [17], the observed proportion of hypomethylated sequences is expected to depend on the number of D4Z4 RUs in the contracted 4q array relative to the number of D4Z4 RUs on the non-contracted 4q array, together with chromosome 4q-type RUs on hybrid chromosome 10s, if present. In addition, preference for the 4q D4Z4 is based on a conserved 4q-specific polymorphism at the 3' terminal base of a BSS PCR primer; however, since this relies on a single base polymorphism, there is the potential that a fraction of 10q-derived D4Z4 sequences could be amplified. In fact, sequence analysis of the DUX4 5' BS PCR products identified both 4qA-specific polymorphisms and 10q-specific polymorphisms, indicating that although the reaction has a preference for 4q, it does not preclude amplification of some 10q array RUs. Fortunately, this does not adversely affect our analysis. For healthy controls we anticipate that the vast majority of the analyzed chromosomes will show D4Z4 hypermethylation (>35% methylation) regardless of origin. By contrast, FSHD1 subjects should contain a combination of hypermethylated (from D4Z4 RUs residing in the non-contracted 4q array and both 10q arrays) and hypomethylated (from the D4Z4 RUs residing in the contracted 4q array) sequences with a clear minority of the analyzed D4Z4 RUs being hypomethylated; FSHD2 subjects should be hypomethylated (~<25% methylation) on most sequences analyzed. Thus, the DUX4 5' BSS assay is expected to be less sensitive than the 4qA and 4qA-L BSS assays in distinguishing FSHD1 from healthy controls; however, this assay should support those results, and would clearly distinguish FSHD2 from FSHD1 or healthy controls. Therefore, to more accurately distinguish FSHD1 from FSHD2 we use the mean percent methylation of each sample for comparison (Table 2).

The DUX4 5' BSS analysis was tested on the same eight genomic DNA samples as above (FIG. 4B). As with the 4qA BSS assay, DUX4 5' BS products from subjects 75195 (91.0% methylation mean, PBMCs; 94.4% methylation mean, saliva) and 75205 (71% methylation mean, PBMCs; 63.9% methylation mean, saliva) showed pronounced DNA hypermethylation in both PBMCs and saliva, suggesting that these two subjects were healthy controls. Subjects 75194 (47.8% methylation mean, PBMCs; 59.7% methylation mean, saliva) and 75204 (50.8% methylation mean, PBMCs; 59.3% methylation mean, saliva) showed less methylation than the putative controls but more methylation, on average, than found for these samples in the 4qA BSS analysis. However, in accordance with our predictions for FSHD1, these subjects contained a mixture of hypermethylated and hypomethylated DNA, resulting in a wide range of DNA methylation density per analyzed chromosome that reached much lower in subjects 75194 (5.1-78.0% methylation, PBMCs; 5.1-81.4% methylation, saliva) and 75204 (6.8-91.5% methylation, PBMCs; 5.1-88.1% methylation, saliva) compared with 75195 (72.9-100% methylation, PBMCs; 78.0-100% methylation, saliva) and 75205 (40.7-88.1% methylation, PBMCs; 32.2-86.4% methylation, saliva). This data supports that subjects 75194 and 75204 are FSHD1 and not FSHD2 patients, while subjects 75195 and 75205 are healthy controls. In each case, the genomic DNAs isolated from PBMCs and saliva samples produced similar BSS results for that subject.

Upon final analysis, subjects 75194 and 75204 exhibited D4Z4 hypomethylation detected by the 4qA BSS analysis (Q1<25% methylated), indicative of FSHD, and by the DUX4 5' BSS analysis they were clearly not FSHD2 (see below) and were thus predicted to be two FSHD1 patients. In fact, subjects 75194 and 75204 indeed had positive genetic tests for FSHD1. Importantly, subject 75204 (34 kb EcoRI/BlnI fragment corresponding to 9 D4Z4 RUs) and subject 75194 (27 kb EcoRI/BlnI fragment corresponding to 7 D4Z4 RUs) were both in the high end of the genetic FSHD1 contraction range, yet both were still accurately identified as FSHD1 by our analysis highlighting the sensitivity of these assays. Similarly, subjects 75195 and 75205, displaying hypermethylation at D4Z4 of all analyzed sequences by both the 4qA BSS and the DUX4 5' BSS methods, were accurately determined to be healthy controls. With respect to the distal 4qA BSS analysis, subject 75195 was accurately identified from both blood and saliva genomic DNA as a healthy control, while control subject 75205 was accurately determined to lack a 4qA allele at either chromosome 4 (see below).

Overall, genomic DNAs isolated from blood and saliva provided similar epigenetic profiles of the FSHD-associated D4Z4 array in FSHD1 affected patients and healthy first-degree relatives. This test analysis confirmed the specificity of the 4qA BSS and 4qA-L BSS protocols for 4qA alleles over 10qA alleles or 4qB alleles. In addition, we have applied this analysis to myogenic cells or PBMCs from an additional 20 subjects having a clinical and genetic diagnosis of FSHD1 and 10 subjects confirmed as healthy unaffected. The simple cutoff of Q1<30% for 4qA and 4qA-L methylation accurately classified 19 of the 20 FSHD subjects and 9 of the 10 healthy controls (p=7×10$^{-6}$ by Fisher's Exact Test); the one false positive was the only sample in the intermediate zone of 25%<Q1<35%. (T. Jones et al. 2014, unpublished observations). We conclude that the described BSS analysis can readily identify FSHD1 hypomethylation, is suitable for epigenetic analysis of the D4Z4 array in both FSHD1 and healthy subjects, and that saliva samples are comparable to PBMCs in terms of providing suitable genomic DNA for DNA methylation analysis of the 4q35 D4Z4.

Identification of the FSHD2 DNA Hypomethylation Signature

Figure 6A:
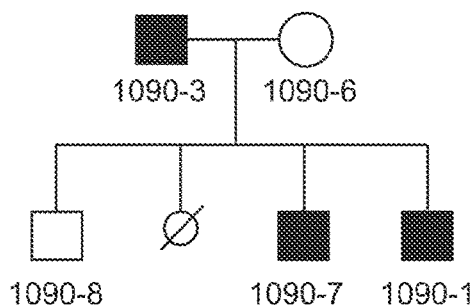
FIGS. 6A-6B: BSS analysis of genomic DNA samples distinguishes FSHD2 from FSHD1. A) Partial pedigree for family 1090, which has a known FSHD2 mutation in the SMCHD1 gene that segregates with disease [27]. B) The 4qA BSS analysis (left) and DUX4 5' BSS analysis (right) for genomic DNAs isolated from subjects in family 1090 or subject RB19518, as indicated. Genomic DNAs were isolated from fibroblasts for subject 1090-1 and PBMCs for all other subjects. Expected CpGs, based on predicted sequence composition of the unconverted region amplified, are listed in numerical order. Dark gray boxes indicate methylated CpGs, light gray boxes indicate unmethylated CpGs and white boxes indicate no CpG detected at the expected site. The Q1 percent methylation is indicated for the 4qA BSS assays and the mean percent methylation is indicated for the DUX4 5' BSS assays.
Figure 6B:
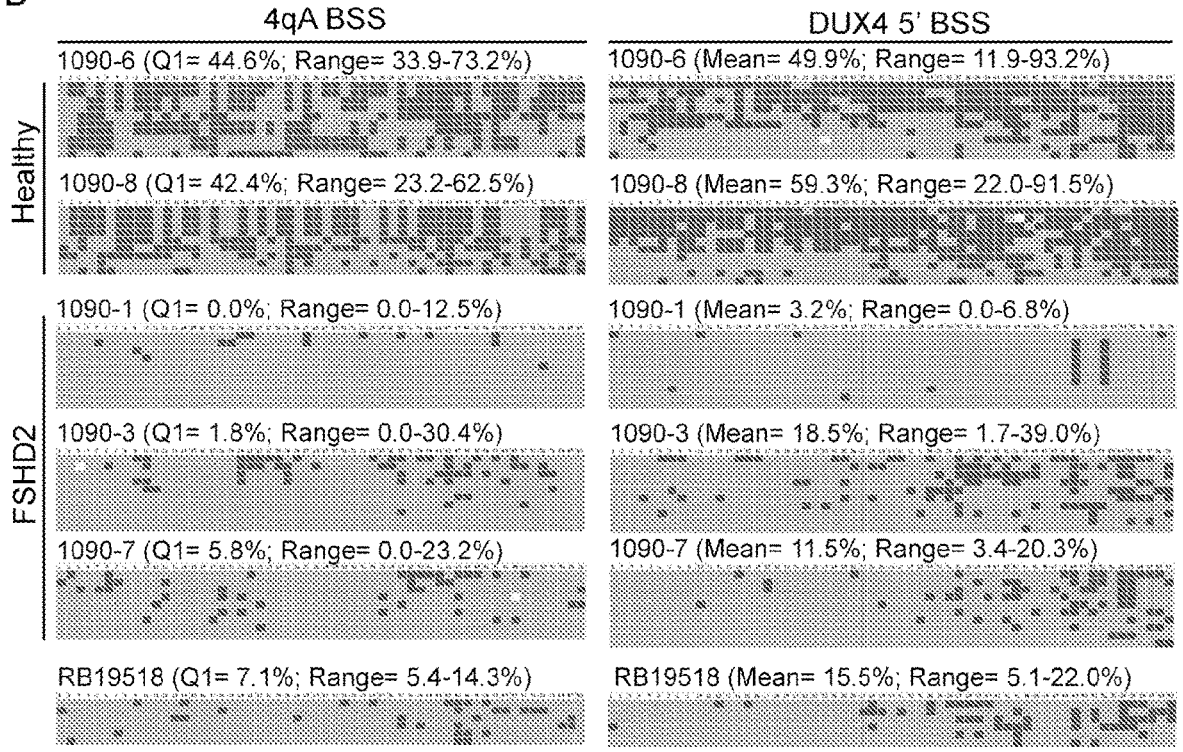

Current genetic testing for FSHD, either by PGFE or molecular combing, detects a contracted 4qA D4Z4 array (FSHD1), and produces a negative result in ~5% of clinically diagnosed FSHD cases. These subjects are candidates for FSHD2. FSHD2 can be diagnosed in two ways: genomic sequencing of the SMCHD1 gene for a known (or likely) FSHD2 mutation (valid for ~85% of cases) or epigenetic analysis of the D4Z4 array (valid for 100% of known cases). The distinguishing feature of FSHD2 is DNA hypomethylation (<25% methylation) of both the 4q35 and 10q26 D4Z4 arrays [19, 21]. In addition, as is the case with FSHD1, FSHD2 requires at least one permissive 4qA allele. Since our BSS analysis identifies 4qA haplotypes and determines the DNA methylation profiles of the D4Z4 arrays on both 4q chromosomes, we sought to determine if our method could be used to identify cases of FSHD2. We used genomic DNAs isolated from fibroblasts or blood obtained from a family containing three known FSHD2 subjects possessing a mutation in SMCHD1 and two unaffected relatives (FIGS. 6A-6B) [27]. Our BSS analysis of the DUX4 5' region showed extreme DNA hypomethylation (3.2%, 18.5%, and 11.5% methylation means; Q3<25%) in all three FSHD2 subjects and, conversely, DNA hypermethylation (49.9% and 59.3% methylation means; Q3>35%) of both healthy controls (FIG. 6B, right column). The 4qA BSS analysis positively detected at least one 4qA allele in each FSHD2 subject with concurrent DNA hypomethylation of all analyzed sequences, and healthy controls were hypermethylated on all 4qA chromosomes (FIG. 6B, left column). These DNA methylation profiles are strikingly distinct from those found for FSHD1 (FIGS. 4A-4B) and clearly identify these subjects as FSHD2. We conclude that our BSS assay can be used to positively detect an FSHD2 epigenetic signature with a permissive 4A subtelomere, readily distinguishable from that of FSHD1 or healthy controls, using standard genomic DNA preparations from multiple sources.

We further tested the utility of this assay by analyzing PBMC genomic DNA isolated from a subject (RB19518) who was clinically diagnosed with FSHD but had a negative genetic test result for FSHD1 by the standard PFGE technique. FSHD2 is characterized by <25% methylation of all four 4q and 10q D4Z4 arrays. In less than five days after obtaining the genomic DNA, the results of our FSHD BSS assays showed a 15.5% methylation mean in the DUX4 5' region, with a range of 5.1-22% methylation, and a Q1=7.1% methylation using the 4qA BSS assay, with a range of 5.4-14.3% methylation, indicating that all detected D4Z4s were hypomethylated (FIG. 6B, lower panels). This analysis indicated that this subject had a clear FSHD2 epigenetic signature and a likely permissive 4A subtelomere and thus, when combined with the clinical evaluation, is very likely FSHD2. We conclude that this assay is a quick and efficient way to determine FSHD2 epigenetic signatures and does not require HMW DNA.

Identification and Elimination of the Rare 10A176T and 4A166 Non-Permissive Haplotypes from BSS Analysis It is important to keep in mind that the majority of analyzed chromosomes in FSHD and healthy subjects will have chromosomes with standard 4qA (44%, including 4qA-L), 4qB (50%), and 10qA (91%) haplotypes; however, there are some important exceptions to consider [18]. Two of them are the rare, non-permissive 10A176T and 4A166 haplotypes, neither of which is identified by current standard diagnostic testing [18]. Since D4Z4 arrays of 10A176T have chromosome 4-like resistance to digestion with Bln-I, the enzyme used to distinguish chromosome 4 arrays from chromosome 10 arrays, this chromosome 10 haplotype can be misidentified as chromosome 4 by PFGE analysis and 4A166 linked arrays are indistinguishable from permissive 4qA arrays using PFGE. Thus, the presence of 10A176T or 4A166 can complicate genetic diagnosis and epigenetic analyses, particularly when these haplotypes are associated with a short D4Z4 array. Since the prevalence of 10A176T and 4A166 in the European population are ~2.5% and ~4.1%, respectively, it is to be expected that ~1 out of 15 FSHD patients, healthy control subjects, and even patients with other myopathies will carry one of these potentially confusing haplotypes [18]. Fortunately, the 10A176T and 4A166 alleles have several distinguishing polymorphisms and can be identified by PCR haplotyping of genomic DNA [15]. However, for our diagnostic purposes as well as epigenetic analyses, it is important to know if our 4qA and 4qA-L BSS assays can identify and/or eliminate these non-permissive 10A176T or 4A166 haplotypes from the BSS analysis.

Figures 7A, 7B:
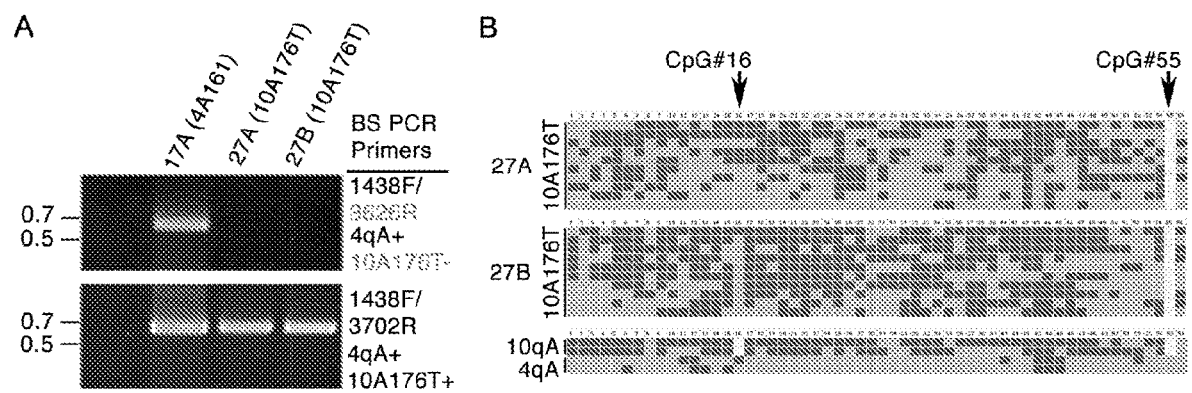
FIGS. 7A-7B: The 4qA BSS analysis does not amplify from 10A176T or 4A166 alleles. A) The 4qA BSS assay (upper panel) is specific for 4qA sequences (present in sample 17A) and does not amplify the non-permissive 10A176T or 4A166 alleles present in samples 27A and 27B. BSS PCR using oligonucleotide primers that do not distinguish between 4A and 10A176T (lower panel) amplifies robustly from all three samples. B) Sequence analysis of the products from samples 27A and 27B confirmed their origins as being from a 10A176T allele. The lack of a detectable CpG at position #55 but the presence of a CpG at position #16 identifies these as derived from a chromosome with a 10A176T haplotype. Expected CpGs, based on predicted sequence composition of the unconverted region amplified, are listed in numerical order. Dark gray boxes indicate methylated CpGs, light gray boxes indicate unmethylated CpGs, and white boxes indicate no CpG detected at the expected site.

Therefore, we tested our 4qA and 4qA-L BSS assays on genomic DNAs known to contain the 10A176T allele. We identified two subjects (27A and 27B) from the same family who have very short D4Z4 arrays in cis with the 10A176T haplotype and one 4A166 allele and one 4B allele [6]. As shown (FIG. 7A, upper panel), no BS PCR product was amplified from these subjects using these assays. This was not surprising considering both 4A166 and 10A176T share the same sequence polymorphisms in the primer BSS3626R that was used to eliminate BS PCR product amplification from non-permissive 10qA (FIGS. 10A-10E). To confirm the content and integrity of these bisulfite-converted DNAs, we used an alternative BSS primer that is not predicted to distinguish 4A from 10A176T for amplification (FIG. 7A, lower panel). Analysis of the amplified product revealed that all sequences matched the predicted polymorphisms for 10A176T, and not 4A or 10A, including the lack of CpG #55 but not CpG #16 (FIG. 7B). Therefore, this additional BSS assay can be used to both positively identify and study the methylation status of chromosomes with the 10A176T haplotype. We conclude that the 4qA and 4qA-L BSS assays do not amplify the 10A176T or 4A166 haplotypes and effectively eliminate them from the methylation analysis.

Combined Analysis and Epigenetic Diagnosis of FSHD

Figure 8:
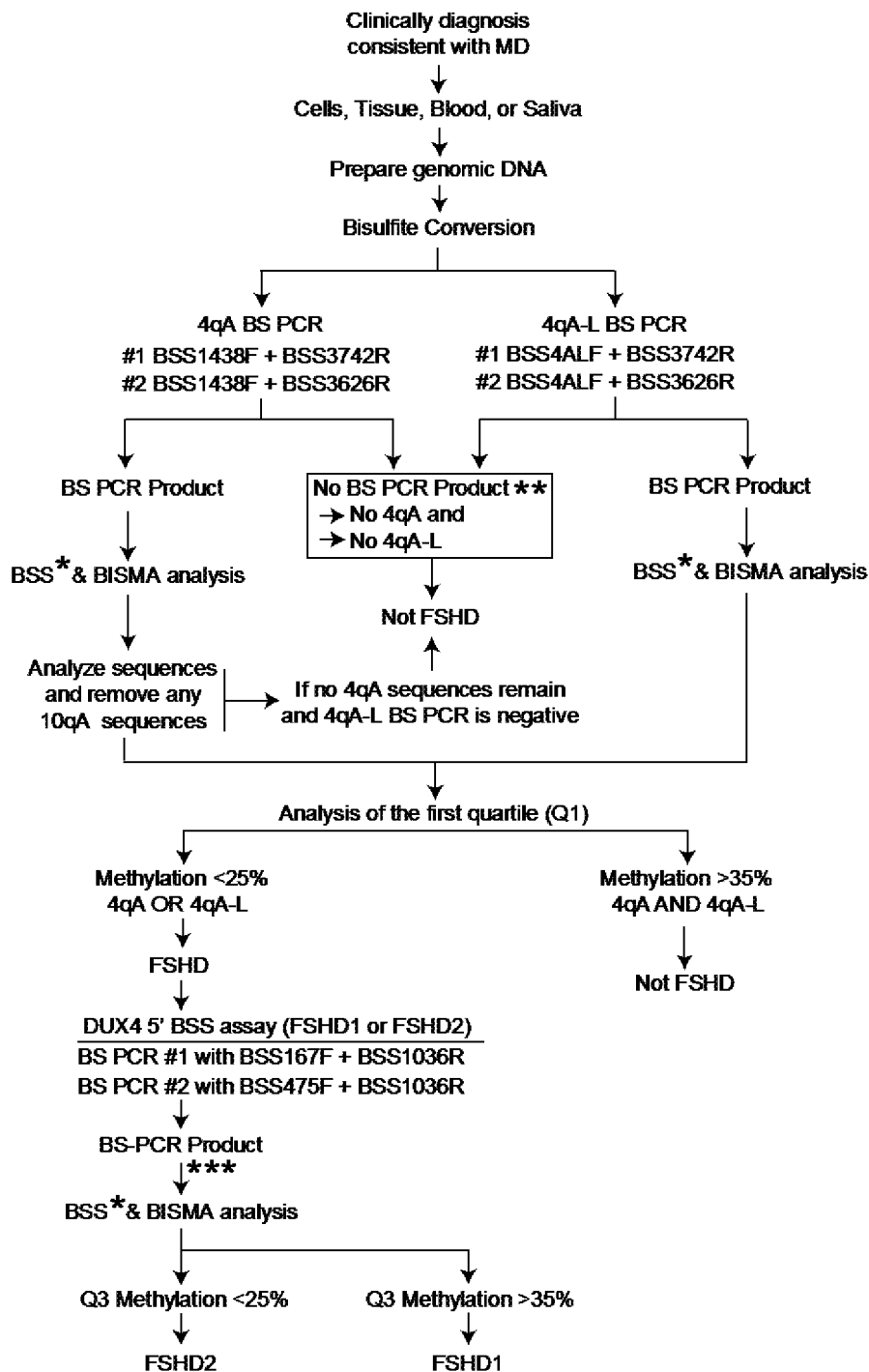
FIG. 8: Flow chart of epigenetic diagnosis of FSHD1 and FSHD2 by BSS. Clinical samples, including saliva, blood, muscle tissue, or cells, from patients with a clinical diagnosis of neuromuscular disease consistent with FSHD can be used for genomic DNA isolation and an epigenetic diagnosis of FSHD1 or FSHD2. The first level BSS assays, the 4qA and 4qA-L BSS assays, identifies FSHD. The second level assay, the DUX4 5' assay, distinguishes between FSHD1 and FSHD2. * Sequence analysis can be performed by subcloning and Sanger sequencing of a minimum of 10 independent clones; alternatively, a NGS approach can be used. Sequences are screened for 10A, 10A176T, and 4A166 and, if present, those sequences are removed from the analysis. The lower quartile (Q1) of the percent methylation is computed for the remaining sequences, to improve sensitivity for detecting hypomethylation on a contracted allele when roughly half the sequences are from a non-contracted allele and are hypermethylated.  If no BS PCR product is generated then the subject likely lacks a permissive 4A haplotype. Genomic PCRs for A- and B-type subtelomeres and sequencing can be used to confirm the results. * Sequence analysis of the BS PCR product, which is derived from both 4q and 10q arrays and thus present in all samples, can be performed by subloning and Sanger sequencing of a minimum of 10 independent clones; alternatively, a NGS approach can be used. The DNA methylation of 10 sequences is not expected to identify strong changes in FSHD1 patients since the vast majority of sequences are likely derived from either the noncontracted 4q or either of the 10q D4Z4 arrays (Q3>35%); however, FSHD2 shows hypomethylation (Q3<25% methylation) on both 4q and both 10q D4Z4 arrays.
Figure 9:
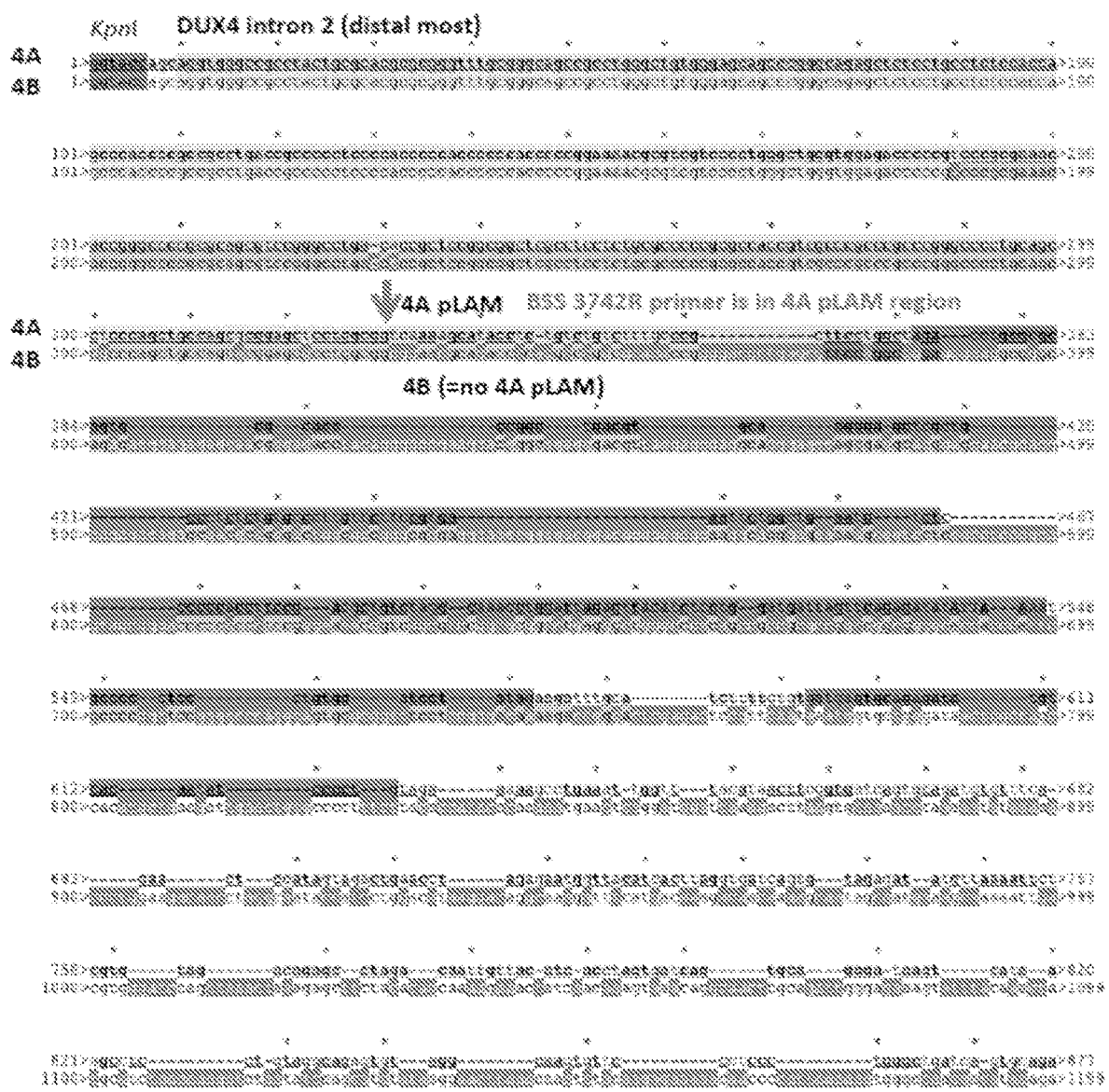
FIG. 9 shows a 4qA sequence (4A) (SEQ ID NO: 4) and a 4qB telomere sequence (4B) (SEQ ID NO: 5).

The three BSS assays presented use DNA methylation levels of the terminal D4Z4 RU to distinguish FSHD from healthy unaffected subjects as well as FSHD1 from FSHD2 (FIG. 8). However, in describing the BSS methods here, only two FSHD1 subjects, four FSHD2 subjects, and four unaffected control subjects were used for this proof-of-principle analysis (FIGS. 4A-4B and 6A-6B). To confirm that the epigenetic signatures of the distal 4qA and DUX4 5' regions could truly be used in the diagnosis of FSHD, we analyzed data produced from our much more extensive epigenetic study of FSHD1-affected and FSHD1-nonmanifesting subjects, which applied this protocol to a larger number of samples (T. Jones et al. 2014, unpublished observations). PBMCs or myogenic cells from a total of 20 clinically affected FSHD1 and 10 healthy subjects, all confirmed by PFGE as FSHD1 or unaffected, were analyzed. The FSHD1 contractions ranged from 14-32 kb EcoRI/BlnI fragments in cis with a permissive A subtelomere, while the shortest 4qA allele EcoRI/BlnI fragment from all unaffected healthy controls was >53 kb. Our analysis of DNA methylation using the 4qA BSS assay with cutoff of Q1<30% accurately classified 19 of the 20 FSHD subjects and 9 of the 10 healthy controls. Interestingly, our previous analysis of DUX4 expression showed that myogenic cells from the false positive, sample 16U, express DUX4-fl mRNA and protein [6], consistent with our epigenetic analysis. This is in stark contrast to the recent BSS method for FSHD published by Gaillard et al. [34], which reported significant population differences between FSHD1 and healthy subjects, but has limited diagnostic benefit on an individual basis. This is not surprising considering the authors use an approach that assays all D4Z4 repeat units from chromosome 4 and chromosome 10 (and perhaps other D4Z4 repeats as well, given the large number of polymorphisms observed in CpG sites [30]), since sequences from the contracted 4q allele then make a small and highly variable contribution to the overall average methylation level. Methylation levels for control samples showed a coefficient of variation (SD/mean) of ~15% in FIG. 5C (left) by Gaillard et al. [34]; thus if only ~10% of sequences in an FSHD1 sample are derived from the contracted allele (as would be expected with, for example, 5 D4Z4 RU on the contracted 4q allele and 45 D4Z4 RU on the non-contracted 4q allele, a conservative estimate as it ignores D4Z4 repeats on other chromosomes), their impact on the observed average methylation level is less than the normal variation between control subjects.

Even a small false positive rate (e.g. 1%) can result in poor positive predictive value when applied to populations in which FSHD prevalence is smaller still (such as the general population). But because individuals with a variety of non-FSHD muscular dystrophies have D4Z4 methylation-levels similar to healthy controls [17], our assay can be used as a differential diagnostic between FSHD and other diseases when applied to patients with clinical characteristics consistent with FSHD. In addition, all of the samples from FSHD1 subjects that were tested with the DUX4 5' BSS assay showed Q3 DNA methylation levels above 25%, consistent with an FSHD1 diagnosis and not FSHD2. Conversely, all FSHD2 subjects showed DNA methylation levels well below 25% in both the DUX4 5' and 4qA BSS assays, Q3 and Q1 respectively, providing clear evidence for FSHD2 as opposed to FSHD1. However, while this assay is specific for the generally FSHD permissive 4qA allele, as with standard FSHD1 testing by PFGE or molecular combing [24], it does not positively identify a functional DUX4 PAS, which is required of a truly permissive 4qA allele. We conclude that the combination of these two assays used for individuals with clinical symptoms of FSHD is diagnostic for FSHD1 and FSHD2 (FIGS. 6A-6B).

Conclusions

We have developed a PCR-based technique to identify and distinguish all forms of FSHD from DNA methylation profiles in blood, saliva, or fibroblasts. The combination of two BSS assays allows the analysis of the DNA methylation profile of a portion of the distal 4q35 D4Z4 RU associated with all forms of FSHD. These assays are specific for 4q chromosomes with the FSHD-associated A-type subtelomere and do not amplify D4Z4 sequence from B-type subtelomeres. Sequences from non-permissive 10qA (including 10qA176T) and 4A166 are not amplified in most assays and, if present (a sign of PCR primer degradation), are readily removed from analysis. The DNA methylation profiles produced by this assay clearly distinguish between FSHD and healthy subjects (FIG. 8). We also describe a companion BSS assay that analyzes the DNA methylation status of a region 5' of the DUX4 gene that is present on all 4q35 and 10q26 D4Z4 repeats. Utilizing the three BSS assays in combination discloses the DNA methylation status of the distal D4Z4 in the context of overall 4q35 D4Z4 DNA methylation. Therefore, in addition to determining contracted 4qA-specific DNA hypomethylation characteristic of FSHD1 and overall D4Z4 hypermethylation in healthy controls, this assay identifies FSHD2-specific DNA hypomethylation signatures on the 4qA allele and clearly distinguishes them from FSHD1 signatures (FIG. 8). Importantly, this analysis does not require HMW genomic DNA and can be performed on genomic DNAs isolated from blood or saliva, producing similar results. Additionally, the protocols can readily be modified with bar-coded oligonucleotide primers such that data acquisition and analysis can be performed using next-generation sequencing technology.

Methods

Subjects and methods: The appropriate local ethics committees approved this study; participants provided written informed consent. Patients 75194, 75204, and RB19518 were clinically diagnosed as FSHD. Patients 75194 and 75204 each had a positive genetic test for FSHD1 and RB19518 had a negative genetic test for FSHD1. Subjects 75205 (healthy relative of 75204) and 75195 (healthy relative of 75194) were clinically unaffected. The FSHD2 family cohort (1090) was previously described [27] and contains a mutation in the SMCHD1 gene that segregates with disease. Myogenic cells for cohort 27 were obtained from the previously described Wellstone Center cell repository housed at the University of Massachusetts Medical School [6, 35].

Sample collection and DNA preparation: Saliva samples (2 ml) were collected from subjects using the DNAgenotek Oragene Discover (ORG-500) DNA collection kit and genomic DNAs were isolated using the manufacturer's recommended protocol. Genomic DNAs from blood samples were isolated using the Qiagen Puregene DNA isolation kit using the recommended protocol.

DNA methylation analysis: DNA methylation was analyzed by BSS assay. Bisulfite conversion was performed on 1 µg of genomic DNA using the EpiTect Bisulfite Kit (Qiagen) as per manufacturer's instructions, and 200 ng of converted genomic DNA was used per PCR. For the 4qA BSS analysis, converted DNA was amplified by nested PCR using oligonucleotide primers and thermocycling conditions that amplify 4qA but not 4qB; the initial PCR was performed with oligonucleotide primers BSS1438F (5'-GTTTTGTTG-GAGGAGTTTTAGGA (SEQ ID NO: 8)) and BSS3742R (5'-AAC̲ATTCAACCAAAATTTCACRAAA⃗ (SEQ ID NO: 2)) and then followed by nested PCR with oligonucleotide primers BSS1438F and BSS3626R (5'-AACAAAAATATACTTTTAACCRCCAAAA̲A̲ (SEQ ID NO: 10)) using 10% of the first PCR product as template. Polymorphic nucleotide changes that preferentially amplify the 4A subtelomeric region are underlined. The BSS3742R sequence does not exist in 4B or 10B and utilizes a polymorphic change at bp 7946 in FJ439133 to eliminate 10A166, and BSS3626R utilizes polymorphic changes at bp 7827 in FJ439133 to eliminate 10A, 4B, and 10B [15]. All PCRs were performed using GoTaq Hot Start Polymerase (Promega) as follows: 94° C. for 2 min, 25 cycles of 94° C. for 15 sec, 58° C. for 20 sec, and 72° C. for 50 sec, followed by a final extension at 72° C. for 10 min. The 593-bp PCR product spans the end of full-length DUX4 exon 1 to the beginning of DUX4 exon 3, therefore allowing specific analysis of the methylation status of the most distal 4qA D4Z4 repeat, which contains 57 CpGs (FIG. 10A). For the 4qA-L BSS analysis, converted DNA was similarly amplified by nested PCR. The initial PCR was performed with oligonucleotide primers BSS4qALF (5'-TTATTTAT-GAAGGGGTGGAGTTTGTT (SEQ ID NO: 11)) and BSS3742R, and then followed by nested PCR with oligonucleotide primers 4qALF and BSS3626R using 10% of the first PCR product as template. All PCRs were performed using GoTaq Hot Start Polymerase (Promega) as follows: 94° C. for 2 min, 25 cycles of 94° C. for 15 sec, 58° C. for 20 sec, and 72° C. for 30 sec followed by a final extension at 72° C. for 10 min. The 354-bp PCR product spans the 3' end of the extended 4qA-L D4Z4 repeat to the beginning of DUX4 exon 3, therefore allowing specific analysis of the methylation status of the most distal 4qA D4Z4 repeat sequence, which contains 30 CpGs (FIG. 10D). When no PCR product was obtained with either the 4qA-or 4qA-L-specific BS PCRs, DNA methylation status of same distal D4Z4 region was analyzed using primer BSS3702R (5'-AAAACCAACRAACTCCCTTACAC (SEQ ID NO: 12)) instead of BSS3626R. BSS3702R amplifies distal D4Z4 from both 10A and 4A. For the DUX4 5' region, bisulfite-converted DNA was amplified by nested PCR as described above. The initial PCR was performed with oligonucleotide primers BSS167F (5'-TTTTGGGTTGGGTGGAGATTTT (SEQ ID NO: 13)) and BSS1036R (5'-AACACCRTAC-CRAACTTACACCCTT (SEQ ID NO: 14)) and then followed by nested PCR with oligonucleotide primers BSS475F (5'-TTAGGAGGGAGGGAGGGAGGTAG (SEQ ID NO: 15)) and BSS1036R. A polymorphic nucleotide change at bp 6748 in FJ439133 (underlined) was used to preferentially amplify the 4A subtelomeric region. This 578-bp PCR product contains 61 CpGs to preferentially analyze the methylation status of the DUX4 5' region of chromosome 4-type D4Z4 repeats (FIG. 10E).

All BS-PCR products were cloned into the pGEM-T Easy Vector system I (Promega) for sequencing analysis. At least 10 clones were sequenced for each subject and their methylation status was analyzed using web-based analysis software BISMA (biochemjacobs-university.de/BDPC/BISMA/) [36] with the default parameters. Default parameters have a lower threshold of 90% identity to the reference sequence, a lower threshold of bisulfite conversion rate of 95%, and remove identical sequences derived from the same genomic template based on conversion artifacts. To remove PCR amplification bias, 1 CpG in BSS3626R primer and 2 CpGs in BSS1036R primer were removed from the analysis; therefore, a total of 56 CpGs, 30 CpGs, and 59 CpGs were analyzed for the 4qA, 4qA-L, and DUX4 5' region, respectively. The "R" designation in primer sequences represents a purine (A or G).

Detection of 10A176T haplotype: BSS analysis using our 4qA-specific BSS primers and conditions does not amplify 10A176T alleles and will eliminate 10A176T from analysis. To confirm a 10A176T haplotype or analyze its DNA methylation status, oligonucleotide primer BSS3626R was replaced with BSS3702R. The bases corresponding to the 55th CpG in the 4qA BSS fragment are "TA" in 10A176T alleles due to the G7820A polymorphic change, and the C7808A polymorphism can be identified as an "A" instead of a "T" at this position in the bisulfite-converted 10A176T [15].

Detailed genotyping of 4q chromosomes: Standard genomic PCR was performed on non-converted DNA to identify the 4qA, 4qA-L and 4qB chromosome as described [15].

Abbreviations

Bp base pair
BS PCR bisulfite PCR
BSS bisulfite sequencing
FSHD facioscapulohumeral muscular dystrophy
HMW high molecular weight
Kb kilobase
PAS polyadenylation signal
PBMC peripheral blood mononuclear cells
PCR polymerase chain reaction
PFGE pulse-field gel electrophoresis
Q1 first quartile
RUrepeat unit

REFERENCES

1. Padberg G W: Facioscapulohumeral Disease [thesis]. Leiden, the Netherlands: Leiden University. 1982.
2. Tawil R, Van Der Maarel S M: Facioscapulohumeral muscular dystrophy. *Muscle Nerve* 2006, 34:1-15.
3. Deenen J C, Arnts H, van der Maarel S M, Padberg G W, Verschuuren J J, Bakker E, Weinreich S S, Verbeek A L, van Engelen B G: Population-based incidence and prevalence of facioscapulohumeral dystrophy. *Neurology* 2014.
4. Brouwer O F, Padberg G W, Wijmenga C, Frants R R: Facioscapulohumeral muscular dystrophy in early childhood. *Arch Neurol* 1994, 51:387-394.
5. Chen T H, Lai Y H, Lee P L, Hsu J H, Goto K, Hayashi Y K, Nishino I, Lin C W, Shih H H, Huang C C, et al: Infantile facioscapulohumeral muscular dystrophy revisited: Expansion of clinical phenotypes in patients with a very short EcoRI fragment. *Neuromuscul Disord* 2013.
6. Jones T I, Chen J C, Rahimov F, Homma S, Arashiro P, Beermann M L, King O D, Miller J B, Kunkel L M, Emerson C P, Jr., et al: Facioscapulohumeral muscular dystrophy family studies of DUX4 expression: evidence for disease modifiers and a quantitative model of pathogenesis. *Hum Mol Genet* 2012, 21:4419-4430.
7. Ricci G, Scionti I, Sera F, Govi M, D'Amico R, Frambolli I, Mele F, Filosto M, Vercelli L, Ruggiero L, et al: Large scale genotype-phenotype analyses indicate that novel prognostic tools are required for families with facioscapulohumeral muscular dystrophy. *Brain* 2013, 136:3408-3417.
8. Schaap M, Lemmers R J, Maassen R, van der Vliet P J, Hoogerheide L F, van Dijk H K, Basturk N, de Knijff P, van der Maarel S M: Genome-wide analysis of macrosatellite repeat copy number variation in worldwide populations: evidence for differences and commonalities in size distributions and size restrictions. *BMC Genomics* 2013, 14:143.
9. Wijmenga C, Frants R R, Brouwer O F, Moerer P, Weber J L, Padberg G W: Location of facioscapulohumeral muscular dystrophy gene on chromosome 4. *Lancet* 1990, 336:651-653.
10. Wijmenga C, Hewitt J E, Sandkuijl L A, Clark L N, Wright T J, Dauwerse H G, Gruter A M, Hofker M H, Moerer P, Williamson R, et al: Chromosome 4q DNA rearrangements associated with facioscapulohumeral muscular dystrophy. *Nat Genet* 1992, 2:26-30.
11. van Deutekom J C, Wijmenga C, van Tienhoven E A, Gruter A M, Hewitt J E, Padberg G W, van Ommen G J, Hofker M H, Frants R R: FSHD associated DNA rearrangements are due to deletions of integral copies of a 3.2 kb tandemly repeated unit. *Hum Mol Genet* 1993, 2:2037-2042.

12. Lemmers R J, de Kievit P, Sandkuijl L, Padberg G W, van Ommen G J, Frants R R, van der Maarel S M: Facioscapulohumeral muscular dystrophy is uniquely associated with one of the two variants of the 4q subtelomere. *Nat Genet* 2002, 32:235-236.
13. Lemmers R J, Wohlgemuth M, Frants R R, Padberg G W, Morava E, van der Maarel S M: Contractions of D4Z4 on 4qB subtelomeres do not cause facioscapulohumeral muscular dystrophy. *Am J Hum Genet* 2004, 75:1124-1130.
14. Lemmers R J, Wohlgemuth M, van der Gaag K J, van der Vliet P J, van Teijlingen C M, de Knijff P, Padberg G W, Frants R R, van der Maarel S M: Specific sequence variations within the 4q35 region are associated with facioscapulohumeral muscular dystrophy. *Am J Hum Genet* 2007, 81:884-894.
15. Lemmers R J, van der Vliet P J, Klooster R, Sacconi S, Camano P, Dauwerse J G, Snider L, Straasheijm K R, van Ommen G J, Padberg G W, et al: A unifying genetic model for facioscapulohumeral muscular dystrophy. *Science* 2010, 329:1650-1653.
16. de Greef J C, Lemmers R J, Camano P, Day J W, Sacconi S, Dunand M, van Engelen B G, Kiuru-Enari S, Padberg G W, Rosa A L, et al: Clinical features of facioscapulohumeral muscular dystrophy 2. *Neurology* 2010, 75:1548-1554.
17. van Overveld P G, Lemmers R J, Sandkuijl L A, Enthoven L, Winokur S T, Bakels F, Padberg G W, van Ommen G J, Frants R R, van der Maarel S M: Hypomethylation of D4Z4 in 4q-linked and non-4q-linked facioscapulohumeral muscular dystrophy. *Nat Genet* 2003, 35:315-317.
18. Lemmers R J, van der Vliet P J, van der Gaag K J, Zuniga S, Frants R R, de Knijff P, van der Maarel S M: Worldwide population analysis of the 4q and 10q subtelomeres identifies only four discrete interchromosomal sequence transfers in human evolution. *Am J Hum Genet* 2010, 86:364-377.
19. de Greef J C, Lemmers R J, van Engelen B G, Sacconi S, Venance S L, Frants R R, Tawil R, van der Maarel S M: Common epigenetic changes of D4Z4 in contraction-dependent and contraction-independent FSHD. *Hum Mutat* 2009, 30:1449-1459.
20. van Overveld P G, Enthoven L, Ricci E, Rossi M, Felicetti L, Jeanpierre M, Winokur S T, Frants R R, Padberg G W, van der Maarel S M: Variable hypomethylation of D4Z4 in facioscapulohumeral muscular dystrophy. *Ann Neurol* 2005, 58:569-576.
21. Lemmers R J, Tawil R, Petek L M, Balog J, Block G J, Santen G W, Amell A M, van der Vliet P J, Almomani R, Straasheijm K R, et al: Digenic inheritance of an SMCHD1 mutation and an FSHD-permissive D4Z4 allele causes facioscapulohumeral muscular dystrophy type 2. *Nat Genet* 2012, 44:1370-1374.
22. Lemmers R J L, de Kievit P, van Geel M, van der Wielen M J, Bakker E, Padberg G W, Frants R R, van der Maarel S M: Complete allele information in the diagnosis of facioscapulohumeral muscular dystrophy by triple DNA analysis. *Ann Neurol* 2001, 50:816-819.
23. Wijmenga C, Frants R R, Hewitt J E, van Deutekom J C, van Geel M, Wright T J, Padberg G W, Hofker M H, van Ommen G J: Molecular genetics of facioscapulohumeral muscular dystrophy. *Neuromuscul Disord* 1993, 3:487-491.
24. Nguyen K, Walrafen P, Bernard R, Attarian S, Chaix C, Vovan C, Renard E, Dufrane N, Pouget J, Vannier A, et al: Molecular combing reveals allelic combinations in facioscapulohumeral dystrophy. *Ann Neurol* 2011, 70:627-633.
25. Lemmers R J, van der Maarel S M, van Deutekom J C, van der Wielen M J, Deidda G, Dauwerse H G, Hewitt J, Hofker M, Bakker E, Padberg G W, Frants R R: Inter- and intrachromosomal sub-telomeric rearrangements on 4q35: implications for facioscapulohumeral muscular dystrophy (FSHD) aetiology and diagnosis. *Hum Mol Genet* 1998, 7:1207-1214.
26. Lemmers R J, van der Wielen M J, Bakker E, Padberg G W, Frants R R, van der Maarel S M: Somatic mosaicism in FSHD often goes undetected. *Ann Neurol* 2004, 55:845-850.
27. Mitsuhashi S, Boyden S E, Estrella E A, Jones T I, Rahimov F, Yu T W, Darras B T, Amato A A, Folkerth R D, Jones P L, et al: Exome sequencing identifies a novel SMCHD1 mutation in facioscapulohumeral muscular dystrophy 2. *Neuromuscul Disord* 2013, 23:975-980.
28. Winston J, Duerden L, Mort M, Frayling I M, Rogers M T, Upadhyaya M: Identification of two novel SMCHD1 sequence variants in families with FSHD-like muscular dystrophy. *Eur J Hum Genet* 2014.
29. Hartweck L M, Anderson L J, Lemmers R J, Dandapat A, Toso E A, Dalton J C, Tawil R, Day J W, van der Maarel S M, Kyba M: A focal domain of extreme demethylation within D4Z4 in FSHD2. *Neurology* 2013, 80:392-399.
30. Zeng W, Chen Y Y, Newkirk D A, Wu B, Balog J, Kong X, Ball A R, Jr., Zanotti S, Tawil R, Hashimoto N, et al: Genetic and Epigenetic Characteristics of FSHD-Associated 4q and 10q D4Z4 that are Distinct from Non-4q/10q D4Z4 Homologs. *Hum Mutat* 2014, 35:998-1010.
31. Ottaviani A, Schluth-Bolard C, Gilson E, Magdinier F: D4Z4 as a prototype of CTCF and lamins-dependent insulator in human cells. *Nucleus* 2010, 1:30-36.
32. Wu H C, Wang Q, Chung W K, Andrulis I L, Daly M B, John E M, Keegan T H, Knight J, Bradbury A R, Kappil M A, et al: Correlation of DNA methylation levels in blood and saliva DNA in young girls of the LEGACY study. *Epigenetics* 2014, 9.
33. Himeda C L, Debarnot C, Homma S, Beermann M L, Miller J B, Jones P L, Jones T I: Myogenic enhancers regulate expression of the facioscapulohumeral muscular dystrophy associated DUX4 gene. *Mol Cell Biol* 2014, 34:1942-1955.
34. Gaillard M C, Roche S, Dion C, Tasmadjian A, Bouget G, Salort-Campana E, Vovan C, Chaix C, Broucqsault N, Morere J, et al: Differential DNA methylation of the D4Z4 repeat in patients with FSHD and asymptomatic carriers. *Neurology* 2014.
35. Homma S, Chen J C, Rahimov F, Beermann M L, Hanger K, Bibat G M, Wagner K R, Kunkel L M, Emerson C P, Jr., Miller J B: A unique library of myogenic cells from facioscapulohumeral muscular dystrophy subjects and unaffected relatives: family, disease and cell function. *Eur J Hum Genet* 2012, 20:404-410.
36. Rohde C, Zhang Y, Reinhardt R, Jeltsch A: BISMA—fast and accurate bisulfite sequencing data analysis of individual clones from unique and repetitive sequences. *BMC Bioinformatics* 2010, 11:230.

TABLE 1

Summary of DNA methylation analysis

| Subject provided herein | Cells | BSS assay | Mean | Min | Q1 | Median |
|---|---|---|---|---|---|---|
| PT-1090-1 | Cells | BSS4qA | 2.68 | 0 | 0 | 0.89 |
| PT-1090-1 | HDF | BSSDUX5' | 3.22 | 0 | 3.39 | 3.39 |
| PT-1090-3 | HDF | BSS4qA | 10.38 | 0 | 1.79 | 4.46 |
| PT-1090-3 | PBMC | BSSDUX5' | 18.47 | 1.69 | 11.86 | 20.34 |
| CTL-1090-6 | PBMC | BSS4qA | 53.57 | 33.93 | 44.64 | 52.68 |
| CTL-1090-6 | PBMC | BSSDUX5' | 49.92 | 11.86 | 18.97 | 53.39 |
| PT-1090-7 | PBMC | BSS4qA | 9.15 | 0 | 5.8 | 8.93 |
| PT-1090-7 | PBMC | BSSDUX5' | 11.53 | 3.39 | 6.78 | 11.86 |
| CTL-1090-8 | PBMC | BSS4qA | 51.59 | 23.21 | 42.41 | 60.71 |
| CTL-1090-8 | PBMC | BSSDUX5' | 59.25 | 22.03 | 27.12 | 66.95 |
| 75194 | PBMC | BSS4qA | 31.07 | 5.36 | 21.43 | 26.79 |
| 75194 | Saliva | BSS4qA | 17.56 | 1.79 | 10.71 | 17.86 |
| 75194 | PBMC | BSSDUX5' | 47.77 | 5.08 | 24.15 | 64.41 |
| 75194 | Saliva | BSSDUX5' | 59.66 | 5.08 | 50.85 | 66.95 |
| 75195 | PBMC | BSS4qA | 91.04 | 82.14 | 87.5 | 90.97 |
| 75195 | Saliva | BSS4qA | 90.54 | 82.14 | 89.29 | 89.29 |
| 75195 | PBMC | BSSDUX5' | 94.24 | 72.88 | 93.22 | 96.61 |
| 75195 | Saliva | BSSDUX5' | 94.41 | 77.97 | 93.22 | 95.76 |
| 75204 | PBMC | BSS4qA | 16.25 | 0 | 7.14 | 12.5 |
| 75204 | Saliva | BSS4qA | 14.11 | 5.36 | 8.93 | 13.39 |
| 75204 | PBMC | BSSDUX5' | 50.85 | 6.78 | 35.59 | 58.47 |
| 75204 | Saliva | BSSDUX5' | 59.32 | 5.08 | 31.36 | 74.58 |
| 75205 | PBMC | BSS4qA | 80.56 | 66.67 | 77.78 | 80.56 |
| 75205 | Saliva | BSS4qA | 84.09 | 66.67 | 75.81 | 85.19 |
| 75205 | PBMC | BSSDUX5' | 71.02 | 40.68 | 57.63 | 73.73 |
| 75205 | Saliva | BSSDUX5' | 63.9 | 32.2 | 55.93 | 61.86 |
| RB19518 | PBMC | BSS4qA | 10.12 | 5.36 | 7.14 | 9.82 |

TABLE 2

Summary of DNA methylation analysis

| subject | Cells | BSS assay | mean | min | Q1 | median |
|---|---|---|---|---|---|---|
| PT-1090-1 | HDF | BSS4qA | 2.68 | 0 | 0 | 0.89 |
| PT-1090-1 | HDF | BSSDUX5' | 3.22 | 0 | 3.39 | 3.39 |
| PT-1090-3 | PBMC | BSS4qA | 10.38 | 0 | 1.79 | 4.46 |
| PT-1090-3 | PBMC | BSSDUX5' | 18.47 | 1.69 | 11.86 | 20.34 |
| CTL-1090-6 | PBMC | BSS4qA | 53.57 | 33.93 | 44.64 | 52.68 |
| CTL-1090-6 | PBMC | BSSDUX5' | 49.92 | 11.86 | 18.97 | 53.39 |
| PT-1090-7 | PBMC | BSS4qA | 9.15 | 0 | 5.8 | 8.93 |
| PT-1090-7 | PBMC | BSSDUX5' | 11.53 | 3.39 | 6.78 | 11.86 |
| CTL-1090-8 | PBMC | BSS4qA | 51.59 | 23.21 | 42.41 | 60.71 |
| CTL-1090-8 | PBMC | BSSDUX5' | 59.25 | 22.03 | 27.12 | 66.95 |
| 75194 | PBMC | BSS4qA | 31.07 | 5.36 | 21.43 | 26.79 |
| 75194 | Saliva | BSS4qA | 17.56 | 1.79 | 10.71 | 17.86 |
| 75194 | PBMC | BSSDUX5' | 47.77 | 5.08 | 24.15 | 64.41 |
| 75194 | Saliva | BSSDUX5' | 59.66 | 5.08 | 50.85 | 66.95 |
| 75195 | PBMC | BSS4qA | 91.04 | 82.14 | 87.5 | 90.97 |
| 75195 | Saliva | BSS4qA | 90.54 | 82.14 | 89.29 | 89.29 |
| 75195 | PBMC | BSSDUX5' | 94.24 | 72.88 | 93.22 | 96.61 |
| 75195 | Saliva | BSSDUX5' | 94.41 | 77.97 | 93.22 | 95.76 |
| 75204 | PBMC | BSS4qA | 16.25 | 0 | 7.14 | 12.5 |
| 75204 | Saliva | BSS4qA | 14.11 | 5.36 | 8.93 | 13.39 |
| 75204 | PBMC | BSSDUX5' | 50.85 | 6.78 | 35.59 | 58.47 |
| 75204 | Saliva | BSSDUX5' | 59.32 | 5.08 | 31.36 | 74.58 |
| 75205 | PBMC | BSS4qA | 80.56 | 66.67 | 77.78 | 80.56 |
| 75205 | Saliva | BSS4qA | 84.09 | 66.67 | 75.81 | 85.19 |
| 75205 | PBMC | BSSDUX5' | 71.02 | 40.68 | 57.63 | 73.73 |
| 75205 | Saliva | BSSDUX5' | 63.9 | 32.2 | 55.93 | 61.86 |
| RB19518 | PBMC | BSS4qA | 10.12 | 5.36 | 7.14 | 9.82 |

Example 2

Results

There are several key distinguishing aspects of our analysis. We studied our well-characterized FSHD1 family cohorts of myogenic cells derived from muscle biopsies [33, 45, 46], thus minimizing differences related to genetic background and also allowing the analysis of multiple cohorts of FSHD1-affected subjects and nonmanifesting carriers containing the same D4Z4 contraction. FSHD is a myopathy and DUX4-fl expression is induced in differentiated myogenic cells [47]; thus, the use of these cells, as opposed to the lymphocytes used in most other studies, allowed analysis of epigenetic status and pathogenic gene expression in the most affected cell type. In contrast to earlier studies which analyzed very few CpGs, our study used bisulfite sequencing (BSS), enabling analysis of the methylation status for >50 CpGs each in both the gene body and 5' promoter region of DUX4 [48]. Importantly, our BSS amplifications were specific to the 4qA D4Z4 (4qA and 4qA-L BSS assays) or the 4q and 10q D4Z4 RUs (DUX4 5' BSS assay). Our assays did not amplify and assess the numerous D4Z4 homologs from other regions of the genome that are not associated with or epigenetically dysregulated in FSHD [48, 49]. Finally, we specifically analyzed the pathogenic distal-most D4Z4 repeat for both DNA methylation status and stability of epigenetic repression as indicated by DUX4-fl expression. This is in contrast to most other studies which have analyzed four centromere-proximal D4Z4 repeats (two from 10q, one from the contracted 4q, and one from the non-contracted 4q); these studies do not specifically assess the pathogenic chromosome and they focus on a region far from the site of stable DUX4-fl expression [25]. Our unique approach provides the first epigenetic analysis of the distal DUX4 gene associated with FSHD, and identifies distinct epigenetic characteristics of healthy, FSHD1-affected, and FSHD1-nonmanifesting states.

The frequency of DUX4-FL expression is stable in culture.

Myogenic cells obtained from different individual donors have large differences in the frequency of DUX4-FL protein expression [33]. Therefore, we first determined if DUX4-FL levels in myogenic cells were stable upon repeated culturing. Our earlier study [33] raised the possibility that DUX4-FL expression frequencies differed depending on the donor; however, that study examined DUX4-FL protein in only one culture for most donors and did not determine if the number of population doublings affected DUX4-FL expression. In addition, DUX4-FL expression in myogenic cells is almost exclusive to differentiated myocytes, as identified by expression of myosin heavy chain (MyHC) [47]; our previous study reported the number of DUX4-FL-positive nuclei per 1,000 total nuclei in the cultures and thus did not account for possibly differing extents of differentiation among different cultures. Thus, to extend our previous study, we examined DUX4-FL expression frequencies at different population doublings (PD) using a serial subculturing assay (see Methods) with differentiated FSHD and unaffected cells derived from the biceps or deltoid muscles of multiple individual donors (Table 3). Upon repeated subculturing, we found that the doubling times of these primary cultures in growth medium began to slow by PD~55-60, therefore we limited DUX4-FL expression experiments to differentiated cultures derived from myogenic cells at PD≤~47, which was prior to the replicative limit.

Figures 11A, 11B:
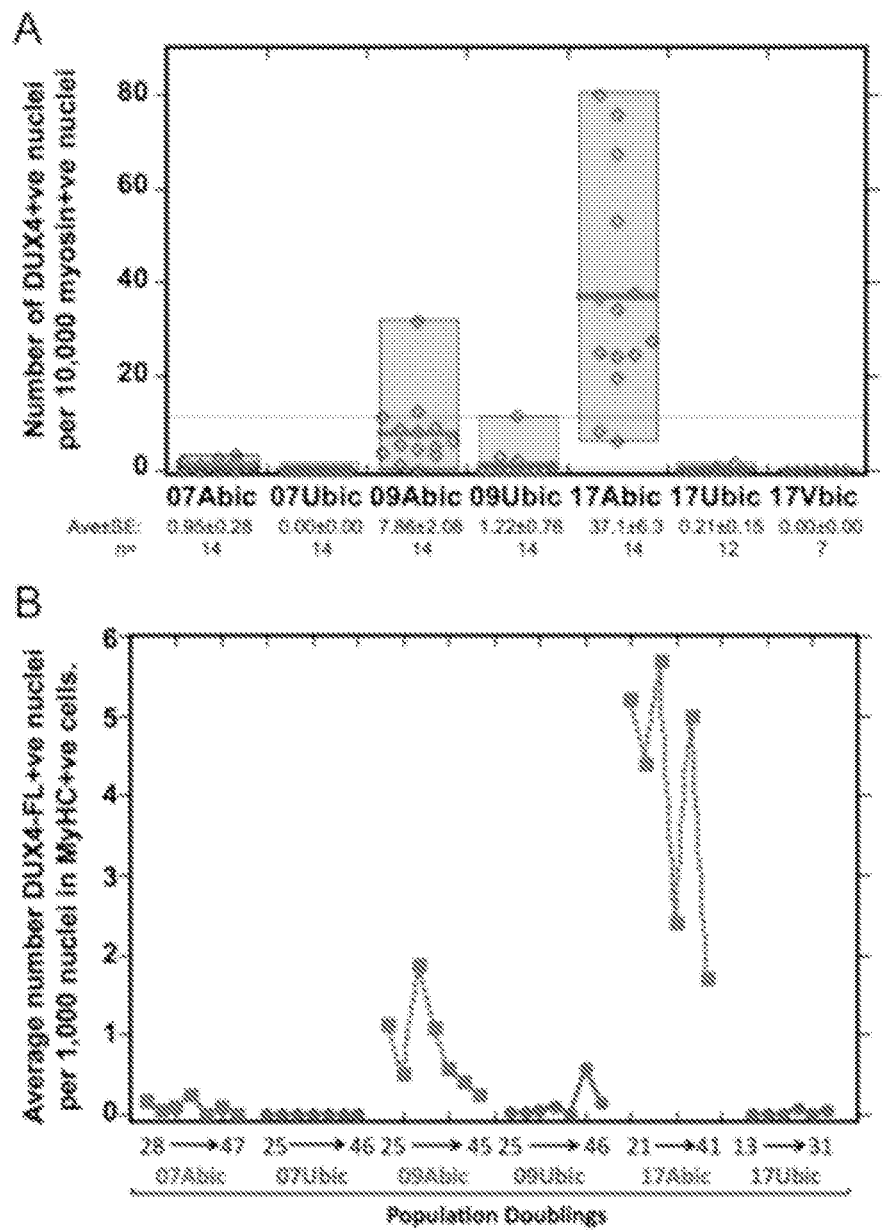
FIGS. 11A-11B: Myogenic cells from different individuals have consistently different and stable frequencies of DUX4-FL expression. A) Myogenic cells from different individuals have different extents of DUX4-FL expression. DUX4-FL expression frequency, expressed as number of DUX4-FL-positive nuclei per 1000 nuclei in myosin-positive cells, was measured in multiple independent cultures of myogenic cells from three FSHD patients (07Abic, 09Abic, and 17Abic) and their unaffected (control) family members (07Ubic, 09Ubic, and 17Ubic, respectively). Within each family, differentiated FSHD cells had a significantly higher frequency of DUX4-FL expression than differentiated unaffected control cells ($P<0.01$; t-tests; n=12-14). In addition, the DUX4-FL expression frequencies of differentiated cells from each FSHD patient differed significantly from each other, with 17Abic>09Abic>07Abic ($P<0.01$; t-tests; n=12-14). Open diamonds=FSHD cultures; closed circles=unaffected control cultures; horizontal bar=average; ave±SE and "n" are shown below each culture name. B) DUX4-FL expression frequency does not show a clear change upon serial subculture. Cultures of cells from the same FSHD and unaffected controls as in panel A were serially subcultured through 6 or 7 passages and DUX4-FL expression frequency was measured at each passage in differentiated cultures as described in Methods. Each point (open diamonds for FSHD, closed circles for unaffected controls) shows results for a single passage, with the passage number increasing from left to right in sequence. The beginning and ending number of total population doublings (PD) undergone for each cell strain is shown below the strain name (e.g., for 07Abic, the cells were first examined at PD=28 and these reached PD=47 at the final passage examined). For cells from each donor, there was no clear change in the frequency of endogenous DUX4-FL nuclei with increased population doublings.

Differentiated cells from three FSHD donors showed an almost 50× difference in average frequency of DUX4-FL expression, with the frequency of DUX4-FL-positive nuclei per 1,000 nuclei in myosin-expressing cells ranging from ~0.1 (for 07Abic cultures) to ~4.7 (for 17Adel cultures) (Table 4). In addition, DUX4-FL expression frequencies were approximately equal for the biceps- and deltoid-derived cultures for each donor (Table 4). We noted that DUX4-FL expression frequencies in these three cohorts inversely correlated with D4Z4 array length as measured by EcoRI-BlnI restriction fragment length (Tables 3 & 4), which, despite the limited sample size, is potentially intriguing considering short 4q D4Z4 arrays (<5 RUs) are associated with severe FSHD disease while longer arrays show more inter-individual variation in clinical severity [20, 25]. For these three FSHD donors, cultures of biceps-derived (Abic) and deltoid-derived (Adel) myogenic cells from 17A consistently had the highest frequencies of DUX4-FL expression, whereas cells from 09A typically had intermediate levels, and cells from 07A typically had the lowest level of DUX4-FL expression (FIGS. 11A-11B). Thus, FSHD cells obtained from different donors maintained consistently different frequencies of DUX4-FL expression upon repeated sub-culturing and over a range of total population doublings. For cells from each of three FSHD donors, the frequency of DUX4-FL-positive nuclei showed a weak trend to lower frequency of expression at higher passages and population doublings ($R^2$=0.16 for 07Abic, 0.32 for 09Abic, and 0.39 for 17Abic).

Consistent with our earlier work [33], we also detected a low frequency of DUX4-FL expression in nuclei within differentiated (MyHC-positive) cells from two of the four healthy (non-FSHD) donors (Table 4). Cells from these two unaffected donors showed a weak trend to higher DUX4-FL expression after repeated subculturing ($R^2$=0.31 for 09Ubic and 0.26 for 17Ubic). As with our previous study investigating DUX4-FL expression in large single cultures of myogenic cells from 9 of the Wellstone Center cohorts (03, 07, 09, 12, 15, 16, 17, 18, 20) [33], for each of the three donor families (07, 09, 17), the average frequency of DUX4-FL-expressing nuclei was higher in differentiated cells from the FSHD donor than from the unaffected donor across multiple cultures (Table 4, n=4-14); this difference reached significance (P<0.05, t-test) in every case except 07Adel vs. 07Udel (P<0.15) (Table 4). Thus, the percentage of myonuclei that expressed DUX4-FL varied among cell cultures isolated from different individuals, but remained relatively stable among different cultures derived from the same donor biopsy. In cultures from all individuals tested, derived from 13 different biopsies, the number of DUX4-FL expressing nuclei remained stable upon repeated subculturing, indicating that the mechanisms regulating DUX4-FL expression are similarly stable in myocyte cell culture.

Myogenic cells derived from FSHD1-affected subjects are significantly hypomethylated at the distal D4Z4 unit of a contracted 4q array compared with the noncontracted allele and healthy controls.

Figures 12A, 12B, 12C:
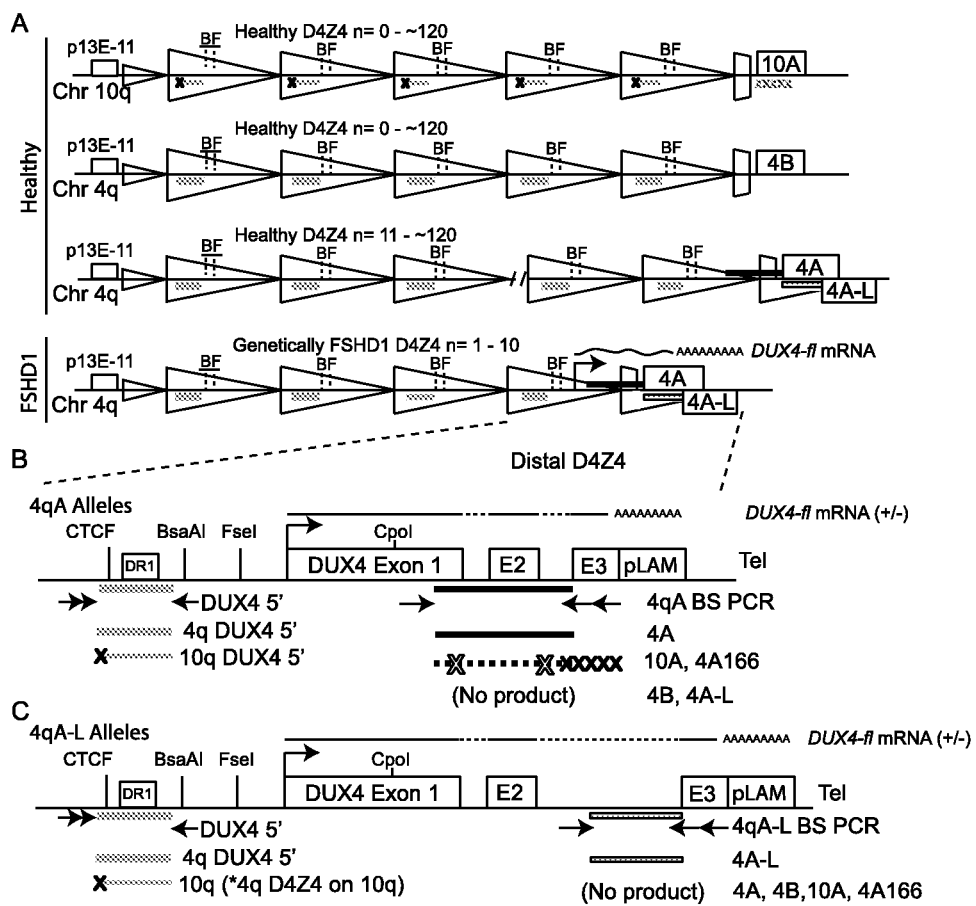
FIGS. 12A-12C: A) Schematic representations of D4Z4 arrays on 4q and 10q chromosomes. Healthy unaffected individuals have any combination of two of the non-contracted 4q chromosomes; FSHD1 is not associated with 4qB or 10qA chromosomes. FSHD1-affected and nonmanifesting subjects have at least one contracted 4qA array and are distinguished clinically by disease presentation. The regions assayed by BSS are indicated as follows: 4qA BSS assay (black bars), 4qA-L BSS assay (open bars), and DUX4 5' BSS assay (gray bars). B=BsaAI and F=FseI restriction sites often used for DNA methylation analysis. B) Schematic of the distal 4qA and C) 4qA-L D4Z4 RUs that are analyzed in this study. Black arrows indicate PCR primer locations. Rare 10qA products can be amplified in the 4qA BSS assay if PCR primers degrade; however, these are clearly identified by sequence polymorphisms (Xs) and removed from analysis.

Overall DNA methylation levels of the 4q35 D4Z4 repeat array differ significantly between healthy cells, which are hypermethylated (>50% methylation of assayed restriction enzyme sites) on both 4q alleles, and cells derived from FSHD1-affected subjects, which are comparatively hypomethylated (<35% methylation of assayed restriction enzyme sites) on the contracted 4q allele [4, 20, 50]. While an earlier study found no significant correlation between disease severity and methylation among FSHD1-affected subjects [20], it did suggest that hypomethylation may, like disease severity, be more pronounced for those subjects with shorter D4Z4 arrays. As mutations in the chromatin regulator SMCHD1 can increase clinical severity in FSHD1 families [6, 29], it is likely that the overall epigenetic state of the 4q35 D4Z4 array can affect the clinical phenotype, even when taking D4Z4 array length into account. Of note, previous reports on FSHD1 DNA methylation assayed only a few CpGs in methylation-sensitive restriction sites either in rare genotypes [20, 50] or in a combined analysis of the most centromeric D4Z4 repeat of both 4q and 10q chromosomes as a proxy for the epigenetic status of the array [4, 25], or analyzed all 4q and 10q D4Z4 RUs as a group (FIGS. 12A-12C) [51]. In particular, one recent epigenetic study did not distinguish the contracted chromosome from the three other non-pathogenic chromosomes [51]. Another study used global estimates of methylation as a function of D4Z4 repeat lengths to detect deviation from predicted average methylation [25], which requires complete knowledge of genotype and cannot ascribe deviation from the predictions to any particular allele. Regardless of the chosen method, all previous studies failed to capture the epigenetic status of the pathogenic distal D4Z4 repeat on the contracted FSHD1 allele [4, 20, 25, 50-52], which may differ between genetically FSHD1 individuals. Considering the stable differences in the number of DUX4-FL expressing myonuclei among cultures from FSHD1-affected subjects, we therefore investigated the DNA methylation profiles of the distal D4Z4 repeat on healthy and FSHD1 alleles, and assessed the stability of epigenetic repression in myocytes at the 4q35 D4Z4 array using DUX4-fl mRNA expression as a read-out for chromatin relaxation. To further address potential connections to FSHD1 disease severity, without the confounding effects of 4qA contraction length or haplotype, we also analyzed familial nonmanifesting carriers of FSHD1-sized contractions.

We developed two BSS assays specific for analyzing the DNA methylation status of the distal D4Z4 on 4qA chromosomes (FIGS. 12A-12C, and [48]) by utilizing polymorphisms in the primers that are exclusive to 4A and not found in 10A or 4B [17]. The 4qA BSS assay analyzes 56 CpGs in the distal D4Z4 RU on 4qA-containing chromosomes, as diagrammed in FIG. 12B. A fraction of chromosomes characterized as 4qA are actually an allelic variant termed 4qA-L; these contain an additional 2 kb of D4Z4 sequence at the distal repeat, resulting in a much larger DUX4 intron 2, while the distal exon 3 and A-type subtelomere are unchanged. Thus, the 4qA-L BSS assay utilizes the same 4A-specific reverse BS-PCR primers as the 4qA assay, but analyzes a distinct set of 30 CpGs in the distal repeat on 4qA-L chromosomes. For comparisons with our 4qA and 4qA-L BSS analyses, as well as with other published studies [51, 52], we designed a BSS analysis upstream of the DUX4 open reading frame (DUX4 5' BSS assay, FIGS. 12A-12C), which analyzes the methylation status of 59 CpGs. This DUX4 5' region is amplified exclusively from all 4q/10q-type D4Z4 RUs, not from other D4Z4 homologs [49], and encompasses a putative CTCF binding site and the DR1 region that is hypomethylated in all 4q/10q D4Z4 RUs in FSHD2 cells [52, 53]. It was critically important that we found these BSS assays to be specific to 4q (4qA and 4qA-L BSS assays) or 4q/10q D4Z4s (DUX4 5' BSS assay), as indicated by the >99.8% coverage of expected CpGs when compared to the reference sequences (FIGS. 13, 14, 15, 16, 17, and 18), because there are D4Z4 homologs on chromosomes 3, 13, 14, 15, 21, 22, and Y which do not show epigenetic changes in FSHD [49]. Fortunately, the 4q and 10q D4Z4s have very high sequence conservation and very few polymorphisms, so even if occasional non-4q/10q D4Z4s were amplified, they would be readily distinguished by their high degree of sequence polymorphisms and discarded from analysis [49]. Thus, combining the 4qA/4qA-L BSS and DUX4 5' BSS provides a specific and detailed analysis of DNA methylation patterns at the pathogenic distal 4qA D4Z4 in the context of overall 4q/10q D4Z4 DNA methylation in FSHD1-affected, nonmanifesting, and healthy control cells.

Figure 14:
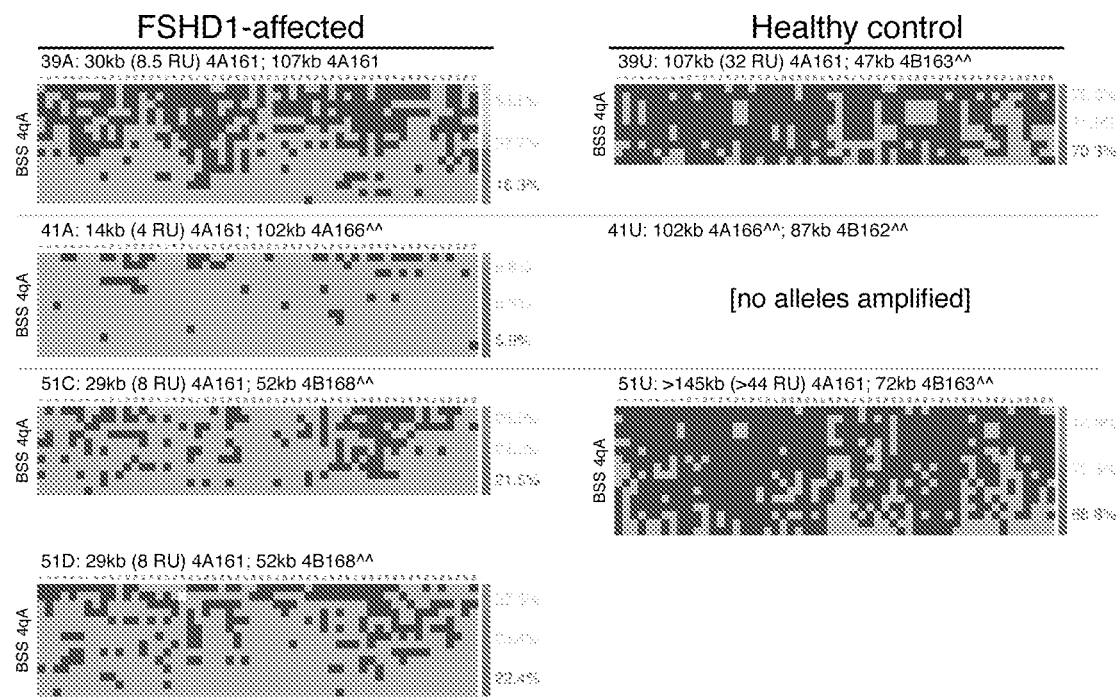
FIG. 14: DNA methylation levels in PBMCs at the distal D4Z4 repeat on the contracted 4qA chromosome correlate with disease. BSS analysis (as described in FIG. 13) of the distal pathogenic D4Z4 RU in family cohorts of PBMCs derived from blood of FSHD1-affected (left column) and healthy unaffected (right column) subjects. Refer to the FIG. 13 legend for additional details and descriptions.
Figure 15:
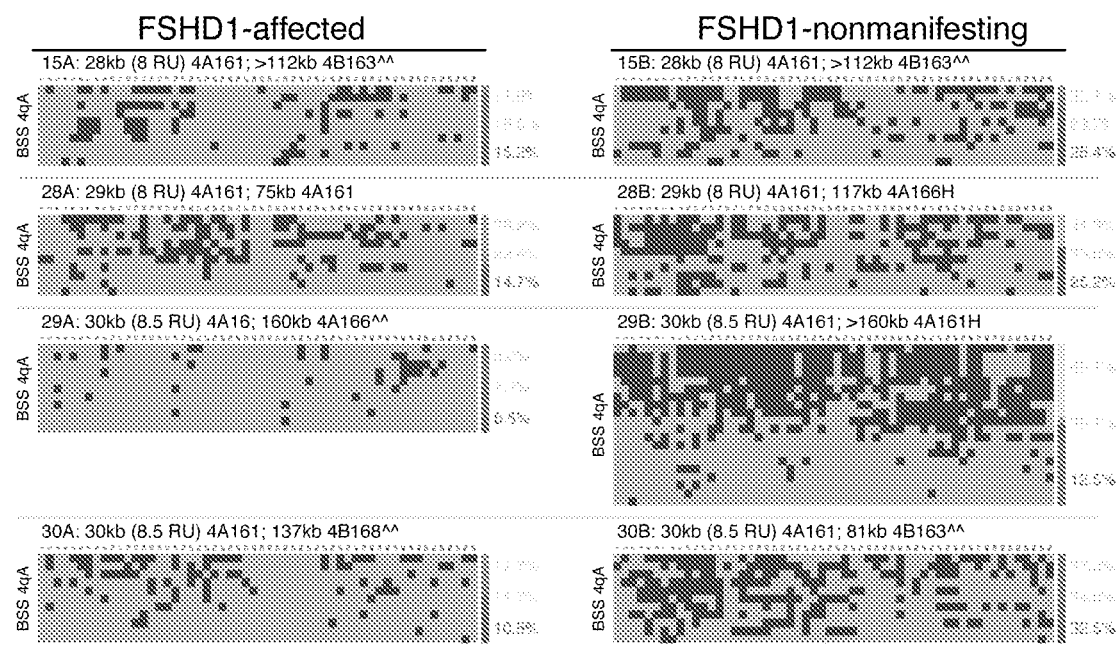
FIG. 15: FSHD1-affected subjects have lower DNA methylation levels in myocytes at the distal pathogenic D4Z4 repeat than nonmanifesting relatives. BSS analysis (as described in FIG. 13) of the distal pathogenic D4Z4 RU in family cohorts of myogenic cells from FSHD1-affected (left column) and FSHD1-nonmanifesting (right column) subjects. As in FIG. 13, on average >99% of the predicted CpGs for the 4qA D4Z4 region were identified in the sequences analyzed for each sample, indicating that the amplified BSS products are specific to 4qA. Refer to the FIG. 13 legend for additional details and descriptions.
Figure 16:
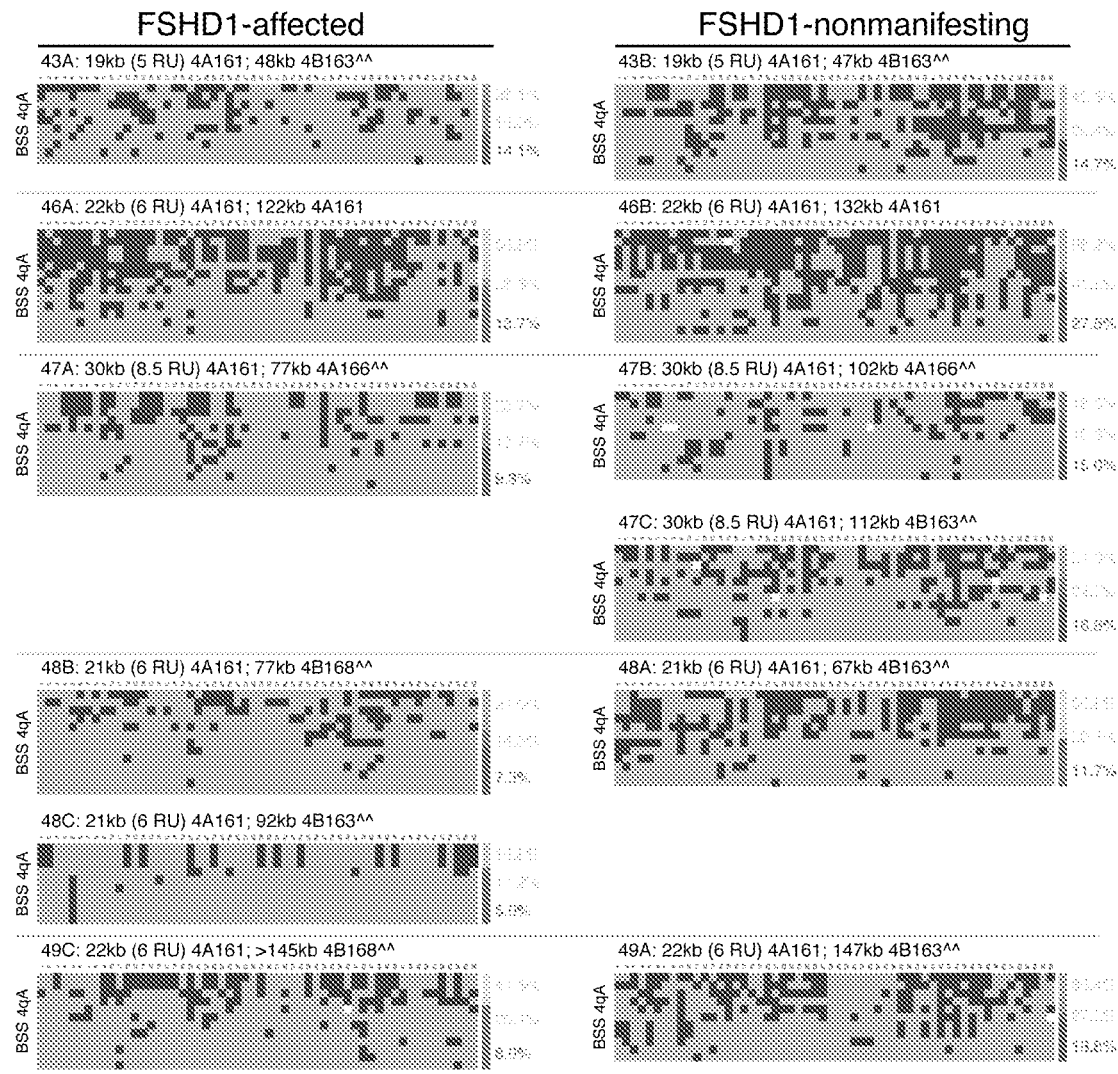
FIG. 16: FSHD1-affected subjects have lower DNA methylation levels in PBMCs at the distal pathogenic D4Z4 repeat than nonmanifesting relatives. BSS analysis (as described in FIG. 13) of the distal pathogenic D4Z4 RU in family cohorts of PBMCs from FSHD1-affected (left column) and FSHD1-nonmanifesting (right column) subjects. Refer to the FIG. 13 legend for additional details and descriptions.
Figure 17:
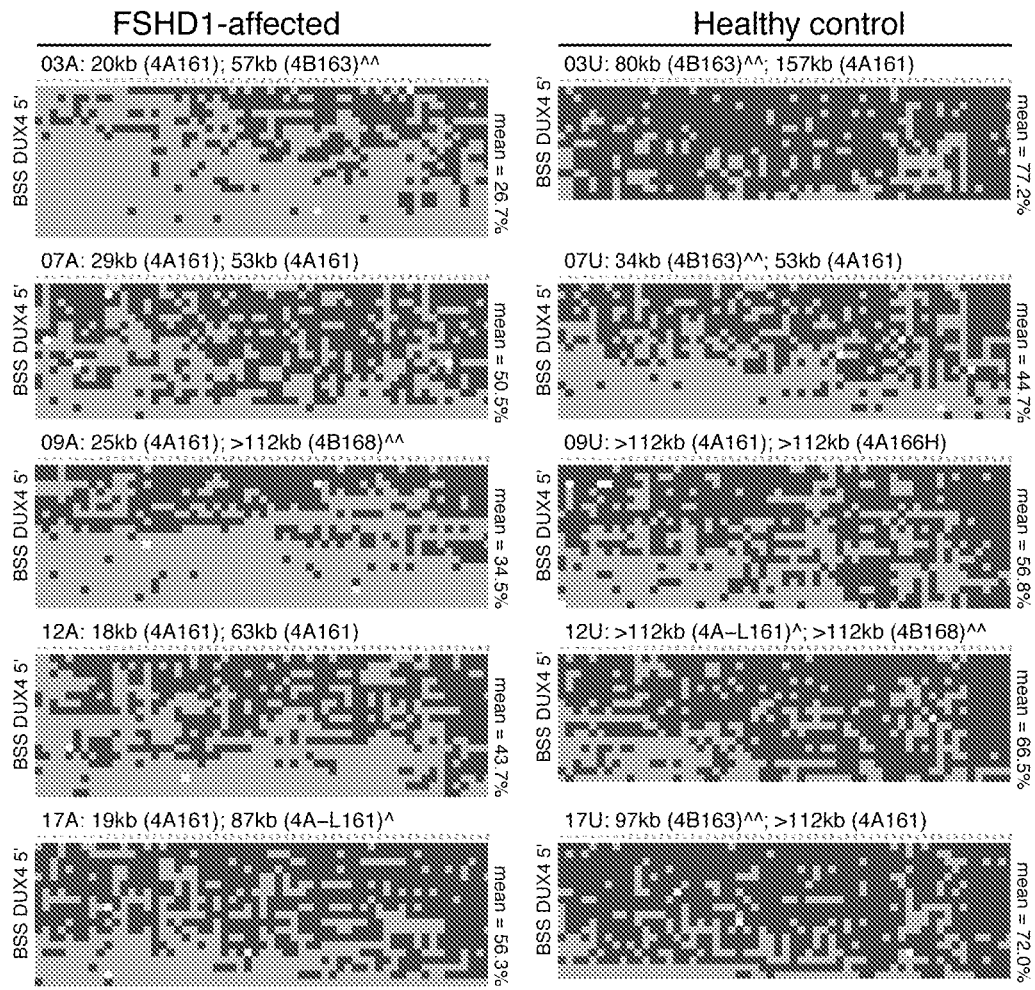
FIG. 17: FSHD1-affected subjects are distinguished by lower levels of DNA methylation than healthy subjects at the 4q/10q D4Z4 5' region. BSS analysis (as described in FIG. 13) of the D4Z4 5' region (FIG. 12) in family cohorts of myogenic cells (03, 07, 09, 12, and 17) derived from biceps of FSHD1-affected (A) vs healthy, unaffected subjects (U). Overall, 56 CpGs were assayed and ~95-100% of the predicted CpGs for the 4q/10q D4Z4 region were identified in all of the sequences analyzed, indicating that the amplified BSS reactions are specific to 4q and 10q D4Z4 repeats.

We used the BSS assays described above to compare DNA methylation profiles (FIG. 13) in myogenic cells from eight familial cohorts (03, 07, 09, 12, 16, 17, 19, and 21) representing clinically affected (manifesting) FSHD1 subjects that showed low (03A, 07A), mid-level (09A), and high (17A) percentages of DUX4-FL expressing myonuclei, and healthy controls (U). In addition, we assayed peripheral blood mononuclear cells (PBMCs) from three familial cohorts (39, 41, and 51) (FIG. 14). In subjects with only one 4qA allele (Table 3), all of the 4qA BSS data was derived from a single allele. Similarly, in subjects with one 4qA-L allele (Table 3), all of the 4qA-L BSS data was derived from a single allele. In subjects with two 4qA alleles, 50% of the BSS sequences are expected to originate from each of the two 4q alleles (although the precise percent may differ due to random sampling fluctuations). Thus, for FSHD1 subjects, 50% of the sequences are expected to originate from the pathogenic D4Z4 RU and 50% from the non-contracted distal D4Z4 RU. However, to prevent high and variable methylation at the non-contracted allele from masking or diluting the signal from the contracted allele, we used a statistical mixture-model to estimate the average percent methylation for just the least-methylated of the 4qA or 4qA-L alleles (see Methods). As expected, the cells from unaffected subjects were hypermethylated (on average 71% methylation across the region for myocytes, 62% for PBMCs) and the cells from eleven FSHD1-affected subjects were hypomethylated (on average 7% for myocytes, 14% for PBMCs). However, despite a >50-fold range in DUX4-FL expressing myonuclei between the FSHD1 samples (FIGS. 11A-11B, and [33]), there were only small differences in average 4qA DNA methylation (03A=5.8%, 07A=17.8%, 09A=6.7%, and 17A=9.2%) for the contracted 4qA chromosomes analyzed for each subject. BSS analysis of the DUX4 5' region supported these results (FIG. 17). Cells from FSHD1-affected subjects displayed higher overall average methylation at the DUX4 5' region than at the 4qA region, but this is to be expected because the non-contracted 4q and both 10q chromosomes are included in analysis of the 5' region; moreover, since any D4Z4 repeat (not just the distal-most) may be amplified in this PCR assay, the contracted 4qA allele makes a proportionately smaller contribution to the overall methylation.

Overall, in cells from FSHD1-affected subjects the contracted 4qA allele is specifically hypomethylated and the non-contracted allele remains hypermethylated. DNA methylation levels at the distal D4Z4 unit are dramatically higher for healthy than for FSHD1-affected cells ($p=2 \times 10^{-12}$, likelihood ratio test [LRT]), correlating with the correspondingly lower numbers of DUX4-FL expressing myonuclei in healthy cells. However, DNA methylation levels alone do not explain differences in the number of DUX4-FL expressing myonuclei among cells from different FSHD1-affected subjects, or explain why so few FSHD1-affected myonuclei in a culture express DUX4-FL. Since DNA methylation is only one component the epigenetic regulation, it is likely that there are additional differences in the overall chromatin state that can account for these changes in expression levels and frequency.

Myogenic cells from FSHD1-nonmanifesting subjects have intermediate DNA methylation levels at the distal DUX4 on the contracted 4q allele.

Figure 18:
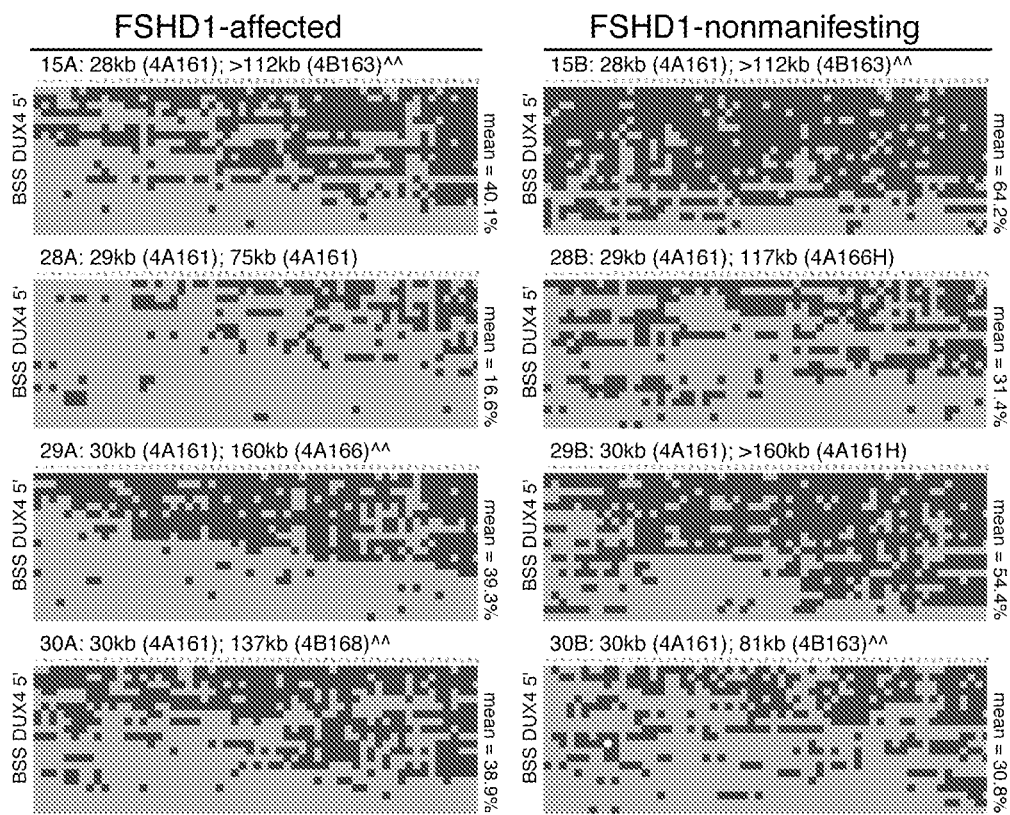

The existence of nonmanifesting carriers of FSHD1-sized 4q35 D4Z4 arrays in FSHD1-affected families has been known for many years, and more recently a high prevalence of D4Z4 array contractions with FSHD-permissive alleles in the general healthy population has been reported [33, 54-60]. Considering that the 4q35 epigenetic status is dramatically different between FSHD1-affected and healthy subjects, we hypothesized that these differences could account for the different disease outcomes between FSHD1 subjects and relatives possessing the same genetic deletion but varying manifestations of weakness. Therefore, 9 family cohorts of genetic FSHD1 subjects with manifesting and nonmanifesting members (Table 3) [33] were profiled with the 4qA/A-L BSS analysis, 4 using myogenic cells and 5 using PBMCs (FIGS. 15 and 16) [33]. Within each family, myocytes from the nonmanifesting subject(s) had higher estimated D4Z4 DNA methylation arising from the contracted allele than myocytes from the manifesting subject(s) (Table 5). DNA methylation analysis of the DUX4 5' region for 4 of the cohorts revealed a similar trend upstream of the gene body with higher average levels of DNA methylation for each nonmanifesting subject compared with the familial manifesting subject (FIG. 18). Thus, despite having the same FSHD1-sized allele, cells from nonmanifesting individuals had higher DNA methylation levels compared with those of manifesting subjects in both the pathogenic distal DUX4 gene body and the DUX4 promoter regions. In every case, nonmanifesting individuals were about the same age or much older than their manifesting relative (Table 3), indicating that increased age does not correlate with loss of methylation.

In summary, higher DNA methylation levels at the distal 4q35 D4Z4 unit on the contracted 4qA allele were significantly correlated with decreased FSHD disease severity in individuals who shared the same FSHD1 deletion ($p=0.004$ by a t parametric sign test, for any choice of which subject to include for the two cases of two affected or two nonmanifesting subjects in a family). This increased level of DNA methylation in nonmanifesting vs. manifesting subjects was also significant in a parametric linear mixed-effects analysis (see Methods), in which levels for nonmanifesting carriers of FSHD1 contractions are slightly but significantly higher than for manifesting subjects ($p=0.02$, LRT), but significantly lower than for healthy controls ($p=1 \times 10^{-7}$, LRT). Notably, there was no significant difference between myogenic cells and blood cells ($p=0.53$, LRT), which makes blood samples appealing as a less-invasive alternative to muscle biopsies, at least for studies of DUX4 methylation.

We conclude that, with respect to the pathogenic distal D4Z4 repeat on the contracted 4qA allele (when appropriate), healthy subjects display DNA hypermethylation, FSHD1 subjects manifesting weakness display hypomethylation, and FSHD1-nonmanifesting subjects display intermediate levels of methylation, slightly but significantly higher than those of FSHD1-affected subjects.

Stability of epigenetic repression is variable between myogenic cells derived from FSHD1-affected and nonmanifesting subjects.

In myogenic cell cultures, cells from FSHD1-affected subjects have a very small percentage of nuclei (1:300-1:10,000) that express detectable levels of DUX4-FL protein (FIGS. 11A-11B), and levels of DUX4-fl mRNA are extremely low [30, 33]. However, virtually all D4Z4-contracted chromosomes analyzed from FSHD1-affected subjects showed robust DNA hypomethylation (FIGS. 13, 14, 15, 16, and 19), indicating that epigenetic repression of DUX4 expression (or stability) is still maintained in the vast majority of myonuclei. Since chromatin states are complex and DNA methylation levels are only one indication of the local chromatin environment, we asked if there were differences in the stability of D4Z4 repression in our family cohorts. To interrogate the epigenetic repression of the 4q35

D4Z4 arrays, cultures of myogenic cells were treated with 5-aza-2'-deoxycytidine (Decitabine/ADC) [61] and/or Trichostatin A (TSA) [62] and DUX4-fl mRNA expression was assayed by qRT-PCR (FIGS. 20 and 21). Decitabine treatment directly leads to decreases in DNA methylation levels [61, 63] and, at certain loci, indirectly causes the reduction of repressive histone marks and the establishment of a permissive chromatin environment marked by nucleosome depletion and histone acetylation [64-66]. TSA is a broad-spectrum histone deacetylase (HDAC) inhibitor that can alter chromatin content by blocking the removal of acetyl groups from histones (and other acetylated nonhistone targets) and inhibiting recruitment of some heterochromatin proteins [62, 67, 68]. Treatment with either Decitabine or TSA relieves epigenetic repression of certain loci, leading to gene activation [69, 70], and the combination of the two drugs can have a synergistic effect [71]. We tested whether treatment with these small molecule enzyme inhibitors might decrease the repressive chromatin content of the D4Z4 array and potentially affect DUX4-fl expression levels.

As seen previously for DUX4-FL protein expression (FIGS. 11A-11B), initial DUX4-fl mRNA levels for the five cohorts analyzed were variable among the FSHD1 cells, while healthy control cells expressed DUX4-fl at much lower levels. FSHD1-affected and control cells were treated with Decitabine, TSA, or both, and DUX4-11 expression was assayed by qRT-PCR (FIG. 20). DUX4-fl was detected in FSHD1-affected cells from both cohorts and, at much lower levels, in healthy controls, consistent with our previous study [33]. Surprisingly, Decitabine treatment of healthy cells, which are hypermethylated at the 4q35 D4Z4 array, only mildly induced DUX4-11 levels and the absolute levels never approached those found in Decitabine-treated cells from FSHD1-affected subjects (FIG. 20). Similarly, treatment with TSA had no effect on DUX4-fl levels in any of the healthy controls. Interestingly, the combination of Decitabine and TSA treatment had a small effect on induction in two of the five healthy lines (09U, 4.7-fold; 07U, 10.2-fold); however, again, the resulting DUX4-11 levels were well below those of the treated cells from all five FSHD-affected subjects (FIG. 20). To control for efficacy of drug treatment we assayed the expression of the ANKRD1 (Ankyrin Repeat Domain 1) gene, which is known to be epigenetically regulated in myocytes [72], and found that Decitabine/TSA treatment significantly induced its expression equally in both unaffected and affected cells (FIG. 22). Thus, in respect to DUX4-fl expression, healthy control cells are refractory to these epigenetic drug treatments, suggesting that normal repression of the non-contracted D4Z4 array is very stable.

Conversely, Decitabine treatment of FSHD1-affected cells, which are already hypomethylated compared with controls at the distal D4Z4 RU (FIGS. 13 and 14), significantly induced DUX4-fl in four of the five subjects (03A, 50-fold; 07A, 120-fold; 17A, 3.2-fold; 19A, 122-fold) with three of the five showing >50-fold induction. The lone cell line (09A) that did not show induction by Decitabine had the highest levels of DUX4-fl mRNA in the untreated sample, and >40-fold more than its corresponding control cell line (09U), suggesting that these cells may have already reached the maximum level of epigenetic relaxation attainable. Of the five cohorts, only 03A, which expressed the lowest levels of DUX4-fl of all the untreated FSHD-affected cells, showed induction by TSA alone. We conclude that myogenic cells from FSHD1-affected subjects have less stable epigenetic repression of DUX4 than their healthy counterparts, and, although the majority of cells do not express DUX4-fl, they are epigenetically poised for DUX4-fl expression.

Similarly, four family cohorts of myogenic cells from FSHD1-affected and nonmanifesting subjects were assayed for their response to Decitabine and/or TSA treatment (FIG. 21). Again, Decitabine induced DUX4-fl expression in cells from FSHD1 individuals manifesting weakness in all four cohorts (15A, 28A, 29A, and 30A), while TSA alone had little to no effect. For 29A, the combination of Decitabine and TSA synergistically induced DUX4-fl expression. In parallel, cells from familial nonmanifesting subjects were subjected to the same set of drug treatments and assayed for DUX4-fl expression. For cells from nonmanifesting subject 29B, the pattern of induction was similar, although less pronounced, to that for cells from FSHD1 subject 29A. However, cells from nonmanifesting subjects 15B, 28B, and 30B showed little to no response to Decitabine or TSA, either alone or in combination.

In addition to FSHD-dependent changes in DNA methylation and histone acetylation states, changes in histone methylation at the FSHD locus have also been reported. These changes include reduced histone H3 lysine 9 trimethylation (H3K9me3) and loss of its binding protein, heterochromatin protein 1 (HP1) [21, 49]. Reducing the levels of H3K9me3 with chaetocin (CH), an inhibitor of the SUV39H1 methyltransferase responsible for establishing H3K9me3, induces DUX4-fl expression in immortalized human KD3 myoblasts [49, 73, 74]. Therefore, we assessed DUX4-fl induction by CH in these cohorts of FSHD-affected and nonmanifesting cells (FIG. 21). Similar to treatment with Decitabine, treatment with CH alone induced DUX4-fl expression, and the combination of both increased expression even further. Again, for each treatment, cells from FSHD1 subjects manifesting weakness had higher DUX4-fl levels than cells from their nonmanifesting relatives with the identical 4qA allele. Thus, the repression of DUX4-fl in cells from nonmanifesting carriers is more refractory to induction by epigenetic drugs than in cells from their clinically affected relatives, despite sharing the same D4Z4 contraction.

Discussion

Patterns of DNA methylation at the pathogenic D4Z4 correlate with disease outcome in FSHD, and can distinguish between FSHD1-affected, FSHD1-nonmanifesting, and healthy controls.

Studies investigating FSHD1 families have identified asymptomatic individuals that share the same FSHD1 genetic diagnosis as their affected relatives, yet report no noticeable muscle weakness [25, 33, 54, 56-58]. Similarly, larger studies of normal individuals with no known FSHD relatives revealed that there are many individuals—reportedly ~1-3% of certain populations—that fit the current FSHD1 genetic diagnostic criteria yet show no clinical manifestation of the disease [60, 75]. It is established that the overall epigenetic status of the 4q35 D4Z4 macrosatellite is distinctly altered between FSHD-affected and healthy control subjects [4, 20, 21, 49, 50, 76]. Therefore, we hypothesized that epigenetic changes, including DNA methylation at the 4q35 D4Z4 array and stability of epigenetic repression of the DUX4-fl mRNA, between individuals could account, at least in part, for the wide variability in clinical presentation of FSHD and similarly for the large number of asymptomatic individuals that fit the genetic criteria for FSHD1 [1, 12, 15, 17, 60, 75, 77]. Supporting this hypothesis, we found that myogenic cells from these FSHD1-nonmanifesting subjects have an intermediate epigenetic status at the pathogenic distal 4q35 D4Z4 repeat that is not as relaxed as that found in FSHD1 subjects manifesting weakness, but not as repressed as that found in healthy control subjects. In addition, DNA methylation levels at this region correlate with clinical disease, showing significant differences between the high methylation levels of healthy controls, the intermediate levels of FSHD1-nonmanifesting subjects, and the low levels of FSHD1-affected subjects. These differences in DNA methylation levels were significant in both a simple paired comparison between family members, and also in a mixed-effect model including all samples (FIG. 19).

This conclusion is in general agreement with a very recent publication that utilized the methyl-sensitive Southern blot method to investigate combined 4q and 10q D4Z4 DNA methylation levels at the proximal D4Z4 RU in FSHD1-affected and asymptomatic/nonpenetrant (comparable to our nonmanifesting) individuals [25]. The authors found that for those genetically FSHD1 subjects carrying 7-10 RUs at their shortest FSHD-permissive allele, affected subjects have significantly less DNA methylation than predicted based on their 4q and 10q D4Z4 array sizes, while asymptomatic subjects do not. This was interpreted as suggesting that for 7-10 RUs, additional factors beyond array size are likely involved in determining methylation levels, and clinical severity, for those with borderline contracted alleles [25]. This is in agreement with our finding that DNA methylation levels on the contracted allele for nonmanifesting subjects differ significantly from those for FSHD1-affected and healthy controls, representing an intermediate level of DNA methylation and epigenetic stability.

In light of this, there are several distinguishing features of our study. We show that in FSHD1 subjects, DNA methylation levels are altered specifically at the contracted distal 4qA D4Z4 RU, and these alterations correlate with disease severity. Importantly, our study goes beyond assaying CpG methylation levels in these subjects and shows that differential DNA methylation is functionally relevant, correlating with general epigenetic repression or relaxation of the contracted 4q35 D4Z4 array, as assayed by the expression of DUX4-fl. Myogenic cells from FSHD1-nonmanifesting subjects, which have intermediate DNA methylation at the distal 4q35 D4Z4 RU of the contracted allele, exhibit greater repression of DUX4-fl than cells from FSHD1-affected subjects, but less repression than healthy control cells. Interestingly, there is also variability in epigenetic repression among FSHD1-affected cells isolated from different subjects, suggesting that an individual's epigenetic status may be an important aspect of clinical progression as well as disease presentation.

Considering that stable pathogenic DUX4-fl expression originates in the distal D4Z4 RU and extends to the permissive A-type subtelomere, it stands to reason that the distal unit on the contracted 4qA allele is the most critical region to analyze. However, due to technical limitations, all previous FSHD epigenetic studies had focused either on the proximal, non-pathogenic 4q/10q D4Z4 RU or on the random analysis of all 4q/10q D4Z4 RUs [4, 20, 25, 50, 51, 76]. Our findings for this distal unit confirm earlier reports that hypomethylation in FSHD1 is restricted to the contracted 4q allele in subjects disomic for chromosome 4 type D4Z4 arrays [4], and moreover offer improved resolution of the allele-specific DNA methylation in two ways: first, in case of 4qA/4qA-L genotypes, the methylation of the two alleles is measured independently; second, for 4qA/4qA genotypes the measurement of methylation at multiple CpG site per molecule allows us to estimate average methylation for each allele separately, rather than simply measuring the average methylation for both alleles combined.

The epigenetic status of the 4q35 distal D4Z4 region, as assayed by CpG methylation and DUX4-fl mRNA induction in response to epigenetic drugs, not only differs strongly between FSHD1-affected subjects and healthy controls, and between FSHD1-nonmanifesting subjects and healthy controls, but also differs between FSHD1-affected and FSHD1-nonmanifesting subjects within families (FIGS. 19 and 21). In fact, DNA methylation analysis of the distal 4qA D4Z4 RU could be used effectively as an FSHD biomarker that distinguishes healthy subjects from FSHD1-affected or FSHD1-nonmanifesting subjects. Within families, analysis of DNA methylation alone can generally distinguish between FSHD-affected and FSHD-nonmanifesting relatives (Table 5; cohorts 15, 28, 29, 30, 46, 47, 48, 49); however, the differences in methylation levels between these genetically FSHD1 groups, while significant at the population-level, are smaller than the differences found between either of the groups and healthy controls (FIG. 19, Table 6). Occasional families in which differences between affected and nonmanifesting subjects are minimal (e.g. cohort 43), and variability in methylation levels between families, suggest that epigenetic factors in addition to DNA methylation are involved in determining if a subject will be clinically affected or disease nonmanifesting. Still, from a diagnostic standpoint, when combined with a clinical evaluation, this DNA methylation analysis will clearly identify both FSHD1-affected and FSHD1-nonmanifesting subjects from healthy (or non-FSHD) controls; the presence or absence of clinical symptoms consistent with FSHD will differentiate the two hypomethylated groups.

The current diagnostic techniques for FSHD1 include pulsed-field gel electrophoresis (PFGE) and molecular combing [78, 79]. These tests can be diagnostic for FSHD1 in a patient with clinical symptoms if a contraction of the 4q35 D4Z4 array is identified ranging between 1 and 10 D4Z4 RUs in cis with an A-type subtelomere [15]; however, many people with RUs in the higher range (7-10 D4Z4 RUs) do not show any clinical manifestation of disease [20, 33]. Therefore, PFGE and molecular combing have much less prognostic value for patients possessing D4Z4 contractions at the high end of the FSHD1 range. However, the epigenetic status of the distal D4Z4 RU does correlate with clinical manifestation and thus may be of more prognostic value.

Our results contrast with a recent study by Gaillard et al. [51], in which D4Z4 DNA methylation levels at the 3' end of D4Z4s (near our 4qA BSS assay) were reported to be unchanged between FSHD1-affected, asymptomatic, and control cells while DNA methylation changes at the D4Z4 5' region (similar to our DUX4 5' BSS assay) could at best only distinguish some FSHD1-affected cells from some unaffected cells, grouping FSHD1 asymptomatic and healthy subjects together. Surprisingly, the authors report D4Z4 DNA methylation levels for FSHD1-asymptomatic cells that were equivalent across the repeat to those found in healthy control cells [51]. This discrepancy between the two studies must be addressed, as it has significant implications for both the clinic, with respect to diagnostics and potentially genetic counseling, and the lab, with respect to understanding disease establishment and mechanism as well as the design of therapeutic approaches. We have identified several critical technical differences between these two studies that can reconcile the data. First, we utilized familial cohorts of FSHD1 subjects with or without disease manifestations who all have D4Z4 repeat arrays of 5-8.5 RU (Table 6); the asymptomatic subjects analyzed in the Gaillard et al. study had 7-10 RU, which is the typical described range for asymptomatic subjects [56, 57, 75, 80]. In our analysis, these FSHD1-affected subjects were analyzed separately (FIG. 19) from FSHD1-affected subjects without familial non-manifesting subjects, which tend to have smaller contracted alleles with less DNA methylation that could skew the analysis [20]. Additionally, our methylation analysis and interpretation of the DUX4 gene body is based on the distal 4qA D4Z4 RU; thus, either 100% (4qA/B) or ~50% (4qA/A) of the assayed chromosomes are from the contracted 4qA array. Therefore, we have specifically analyzed the methylation status of multiple independent sequences from the FSHD1-associated D4Z4, which is important because in FSHD1 only the contracted 4q D4Z4 array shows epigenetic changes [76]. In contrast, the Gaillard et al. study combined all FSHD1-affected subjects, regardless of repeat size or familial relationship, which potentially skewed the average methylation for FSHD1-affected subjects to be lower than if only FSHD1-affected subjects with similar repeat sizes as their FSHD1-asymptomatic subjects were analyzed. In addition, the BSS assays utilized by Gaillard et al., similar to our DUX4 5' assay, do not distinguish between 4q and 10q D4Z4s, and are therefore dominated by D4Z4 sequences derived from the expanded 4q/10q D4Z4 arrays, with sizes averaging between 25-60 RUs and potentially reaching over 100 RUs each, leaving D4Z4s from the much smaller contracted FSHD1-associated 4q D4Z4 array (n≤11) as a clear minority in, and potentially altogether absent from, the assayed population. Therefore, in the analysis of 10 randomly amplified D4Z4s, the impact of sequences from contracted 4qA alleles on the overall average methylation is expected to be small, and likely within the range of normal variation for the other alleles; thus, their analysis has severely limited statistical power. A further complication involves the sequence variability of BSS amplicons. 4q and 10q D4Z4 repeats have very few sequence polymorphisms [49], data supported by both of our BSS assays, which both show >99.8% identity to the expected reference sequence (FIGS. 13, 14, 15, 16, 17, and 18), and others [52]. The presence of numerous sequence polymorphisms affecting expected CpG dinucleotides in the Gaillard et al. BSS analysis strongly suggests that D4Z4s were amplified from non-4q/10q D4Z4 homologs [49]. Considering that these D4Z4 homologs are not associated with FSHD or epigenetically altered in the disease [49], any inclusion of these sequences further complicates the methylation analysis, as it further dilutes the signal from the contracted 4qA allele (important for FSHD1) and also dilutes the signal from combined 4q/10q alleles (important for FSHD2). Thus, the discrepancy between our study and the Gaillard et al. study is likely due to differences in: 1) class of subjects analyzed, 2) specificity of the BSS assays, and 3) statistical power of the analysis. It could be suggested that differences might result from our analysis being performed on fewer subjects; however, the fact that the smaller number of samples in our study produced much clearer and more significant differences actually highlights the power of our technique.

Overall, the DNA methylation results produced by our analysis are consistent with the majority of published literature for FSHD1-affected subjects and healthy controls, and the sequences analyzed are clearly specific for the FSHD1-associated D4Z4 array. Therefore, we conclude that FSHD1-nonmanifesting subjects have an intermediate DNA methylation state at the distal D4Z4 on the contracted 4qA allele that distinguishes them from FSHD1 subjects with muscle weakness and from healthy control subjects. In addition, this intermediate state is functionally relevant in that myocytes from FSHD1-nonmanifesting subjects exhibit more stable epigenetic repression than their counterparts from FSHD1-affected first-degree relatives. These different epigenetic states of the distal 4qA D4Z4 repeat can be used effectively as disease biomarkers that clearly distinguish between FSHD1 subjects and healthy controls regardless of any familial relation [48], have clinical implications for FSHD diagnostics and therapy development, and provide a basis for understanding the mechanism of disease establishment. For example, our results suggest that restoring even an intermediate level of DNA methylation or small increases in heterochromatinization of the D4Z4 array might be sufficient to lower DUX4-fl expression to a non-pathogenic level. In addition, DNA methylation has been found to decrease with age, and these aging-related changes are not global within a cell; some genomic regions change while others do not, and the changes are tissue-specific [81-83]. It is not known if the 4q35 D4Z4 array is susceptible to age-related changes in DNA methylation, but it is possible that the initial epigenetic status of contracted D4Z4 arrays could affect age-related demethylation and thus age of onset or severity of disease.

FSHD1-sized D4Z4 arrays have characteristics of metastable epialleles.

The epigenome consists of DNA methylation, histone post-translational modifications, and histone variants throughout the genome that together form an integral component of gene regulatory mechanisms [84-86]. Initially established during development, the epigenome organizes chromatin to restrict or facilitate the access of regulatory factors to DNA. Epigenetic marks provide a mechanism for regulatory memory that is passed on to subsequent cellular generations and is vital for maintaining cell-type specific patterns of expression and repression. The epigenetic modifications at the 4q35 D4Z4 array are established during early development [30] and differ among individuals. Potentially, variable aspects of the contracted D4Z4 array such as size or inherited DNA methylation patterns, when combined with an individual's expression level or functional status of chromatin modifying proteins such as SMCHD1, could shift the establishment of D4Z4 epigenetic repression in either direction. Similarly, stress, nutrition, and exposure to other environmental factors during critical points in development could influence the overall epigenetic state at the D4Z4 arrays. Once established, the epigenetic state would persist and provide protection from or susceptibility to aberrant DUX4-fl expression in muscle.

In addition to the strong influence of epigenetic regulation, another important aspect of FSHD1 contracted D4Z4 regions is the variegated gene expression of DUX4-fl mRNA, as both traits are characteristic of metastable epialleles. Metastable epialleles (reviewed in [43, 44]), as opposed to traditional alleles, have variable expressivity leading to phenotypic mosaicism between individuals, as well as variegated cellular expression leading to phenotypic mosaicism between cells. This variable expression is not due to genetic heterogeneity, but rather is dependent on the epigenetic state, which is established in a probabilistic manner during development and then maintained in subsequent cellular generations. FSHD presents clinically with great variability in age of onset, affected muscles, rate of progression, and ultimate severity, even within families and among monozygotic twins [87-91]. The variegated DUX4-fl expression patterns in FSHD1 myogenic cells and the variable clinical manifestation in genetically FSHD1 individuals appear consistent with the FSHD1-associated DUX4 allele functioning as a metastable epiallele [8].

Conclusions

FSHD is characterized by epigenetic dysregulation [8]. Here, we show that in the context of an FSHD1 disease-permissive allele, consisting of a contracted 4q D4Z4 in cis with a permissive A-type subtelomere, the epigenetic state of the 4q35 array is dominant over the genetic state in terms of disease outcome (FIG. 23). Our DNA methylation analysis has uncovered distinct epigenetic states at the distal 4q D4Z4 array for unaffected, FSHD1-affected, and FSHD1-nonmanifesting subjects, and has the potential to be used for diagnostic purposes. These different epigenetic states affect the stability of gene repression and potentially the splicing of the pathogenic DUX4-fl isoform. In addition, the contracted 4qA allele in genetically FSHD1 subjects has the characteristics of a metastable epiallele, which may impact disease establishment and progression, and provide an avenue to therapy via epigenetic manipulation.

Methods

Human Subjects. This study was approved by the Johns Hopkins School of Medicine Institutional Review Board. Families with a member diagnosed with FSHD1 were invited to participate. Individuals were genotyped and considered to be affected with FSHD1 if a 4qA EcoRI/BlnI fragment <35 kb was identified using genomic DNAs isolated from peripheral blood mononuclear cells (PBMC) or considered to be healthy controls if they lacked a contracted 4qA allele (Table 4). Haplotypes for both 4q alleles were determined for all subjects, as described [17]. All FSHD1 individuals were examined by an experienced neuromuscular physician (KRW). FSHD1 individuals were further characterized as "manifesting" disease (affected) if they had weakness in the distribution classic for FSHD (e.g. face, shoulder girdle, biceps) or "nonmanifesting" if they had full strength in this distribution.

Clinical samples. Myogenic cells derived from biceps muscles of genetically FSHD1 subjects (03Abic, 07Abic, 09Abic, 12Abic, 17Abic, 15Abic, 15Bbic, 16Abic, 19Abic, 21Abic, 28Abic, 28Bbic, 29Abic, 29Bbic, 30Abic, and 30Bbic) and their healthy unaffected first-degree relatives (03Ubic, 07Ubic, 09Ubic, 12Ubic, 16Ubic, 17Ubic, 17Vbic, 19Ubic, and 21Ubic) were used in this study (as previously described, Homma et al). All cells were obtained from the Paul. D. Wellstone Muscular Dystrophy CRC for FSHD at the University of Massachusetts Medical School, Worcester, Mass. (www.umassmed.edu/wellstone/). Myogenic cells were selected by FACS for CD56 expression such that all cultures were >90% desmin-positive [33, 45]. Myogenic cells were grown on gelatin-coated dishes in high serum growth medium for proliferation, then switched to low serum differentiation medium to induce myotube formation [33, 45]. As described [92], proliferation of primary cultures of human myogenic cells began to slow at 55-60 population doublings as cells neared replicative limits. Therefore, all cells were used at <30 population doublings, except where indicated in subculturing experiments when cultures were examined at up to 47 population doublings. For all subjects in cohorts 39, 41, 43, 46, 47, 48, 49, and 51, DNA methylation analysis was performed on genomic DNAs isolated from PBMCs collected under IRB-approved protocols at the appropriate institution.

Serial sub-cultures. Myogenic cells were cultured in growth medium on gelatin-coated plates to ~80% confluence, at which time cells were counted to calculate population doublings and passaged at 1:10 dilution. At each passage, cells were cultured in parallel on one 100 mm plate and one gelatin-coated four-well chamber slide. The culture in each plate was used to maintain myoblasts in growth medium for additional passaging, whereas the culture in each chamber slide was used to generate differentiated myotubes, which were analyzed for DUX4-FL and MyHC expression after four days in differentiation medium.

Drug treatment. Stock solutions of 100 mM 5-Aza-2'-deoxycytidine/Decitabine, (Sigma-Aldrich A3656) in DMSO, 5 mM Trichostatin A solution (TSA, Sigma-Aldrich T1952), and 10 mM chaetocin (Sigma-Aldrich C9492) in DMSO were stored at −20° C. and diluted with PBS just before adding to the culture. To minimize culturing artifacts, low passage (<30 population doublings) myoblast cultures were used for all experiments and culture pairs for affected vs healthy or affected vs nonmanifesting were within 1 passage of each other in all instances. Myoblasts were seeded on collagen-coated plates at a cell density of $1.9 \times 10^3/cm^2$. Starting the following day, Decitabine (5 µM final concentration) was added daily for a total of 3 days. When used, TSA (200 nM final concentration) or chaetocin (50 nM final concentration) was added to the cells for the last 24 hrs prior to sampling.

Immunostaining. Myogenic cell cultures were fixed and co-immunostained for DUX4-FL and myosin heavy chain (MyHC). DUX4-FL was detected with either P4H2 mouse mAb as described [33] or rabbit mAb E5-5 (Epitomics, Burlingame, Calif.) as described [47]. MyHC isoforms were detected with either mouse mAb MF20 or mouse mAb F59 [93], which were obtained from the Developmental Studies Hybridoma Bank developed under the auspices of the NICHD and maintained by the University of Iowa, Department of Biology, Iowa City, Iowa. Nuclei were stained with bisbenzimide. The number of DUX4-FL-positive nuclei was determined from manually scanning the entire culture area. The number of nuclei in MyHC-positive cells and the total number of nuclei was approximated for each cell strain by counting 10 random fields of known area at 10× magnification and extrapolating to the total area of the well. 60,000 to 150,000 nuclei were screened for each cell culture. Cultures were imaged with a Nikon E800 fluorescence microscope with Spot camera and software, version 4.6 (Diagnostic Instruments, Inc., Sterling Heights, Mich.).

BSS DNA methylation analysis. For all subjects in cohorts 03, 07, 09, 12, 15, 16, 17, 19, 21, 28, 29, and 30, DNA methylation analysis was performed on genomic DNAs isolated from myocytes. For all subjects in cohorts 39, 41, 43, 46, 47, 48, 49, and 51, DNA methylation analysis was performed on genomic DNAs isolated from PBMCs. DNA methylation of the 4qA and 4qA-L distal regions was analyzed using the 4qA BSS and 4qA-L BSS assays, as described [23, 48]. BSS analysis of 59 CpGs in the DUX4 promoter region (DUX4 5' BSS assay) of 4q and 10q D4Z4 repeats was performed using primers BSS167F: TTTTGGGTTGGGTGGAGATTTT and BSS1036R: AACACCRTACCRAACTTACACCCTT, then followed by nested PCR with BSS475F: TTAGGAGGGAGGGAGG-GAGGTAG and BSS1036R using 10% of the first PCR product. PCR products were cloned into the pGEM-T Easy vector (Promega), sequenced, and analyzed using web-based analysis software BISMA (biochemjacobs-university.de/BDPC/BISMA/) [94] with the default parameters.

Allele-specific DNA methylation estimation. The percentage of methylated CpG sites in a region can vary between alleles, and can also vary between cells for the same allele. To prevent high methylation on the non-contracted 4qA allele from masking or diluting the signal for reduced methylation on the contracted 4qA allele (a weakness with methods that only measure overall average methylation [20]), we wish to estimate methylation for just the allele with lower methylation. For the purpose of distinguishing FSHD1-affected subjects from healthy controls we proposed a simple score, the lower quartile (Q1) of percent methylation of all sequenced clones [48]. If two alleles have non-overlapping ranges of methylation and are represented in roughly equal proportions, this will approximate the median for just the allele with lower methylation. But if two alleles have overlapping ranges of methylation, Q1 is biased toward underestimating the median for the allele with lower methylation. Likewise, and akin to the extreme cases in which two alleles have identical distributions, Q1 will underestimate the median methylation in cases where only one allele is amplified by the PCR assay, e.g. if the other allele is a 4B, 4A-L, or 4A166 haplotype, which may not be known in advance. To reduce this bias, here we use a parametric model-based method for estimating allele-specific methylation.

The distribution of counts of methylated CpG sites across clones is not satisfactorily modeled by a binomial distribution, as the observed variance is typically ~4 times greater than that of a binomial distribution with the same mean and N (where N is the number of CpG sites; N=56 for the 4qA assay, and N=30 for the 4qA-L assay) (FIG. 24). This overdispersion is not simply due to the presence of two alleles with different methylation probabilities, as it is also seen when restricting the analysis to samples for which all clones arise from a single 4qA allele (e.g. 4qA/4qB genotypes). This overdispersion can also not be addressed by allowing site-specific methylation probabilities for each CpG site (as in [95]) since by a convexity argument the resulting Poisson binomial distribution has variance at most as large as a standard binomial distribution with the same mean and same N.

To account for the overdispersion, the number of methylated CpGs for each allele (i=1, 2) was modeled as a beta binomial distribution, where each clone (indexed by j) from the allele has an average methylation probability $p_{ij}$ drawn independently from a beta distribution with parameters $a_i$ and $b_i$ and the observed number of methylated CpGs follows a binomial distribution with probability $p_{ij}$ and sample size N. This distribution has the expected average CpG methylation fraction $a_i/(a_i+b_i)$, with variance decreasing as $a_i+b_i$ increases, approaching a binomial distribution in the limit of large $a_i+b_i$. A Bayesian two-component mixture model was used to infer the parameters of the beta binomial distributions for each of the alleles, and to compute the posterior probability of each sequence having originated from each allele, based on the observed methylation data. (Note that unlike refs [95, 96] we model just the total count of methylated CpGs, and not site-specific methylation probabilities; we also differ in using full Bayesian inference rather than maximum likelihood estimation.)

The beta binomials were re-parameterized by $r_i=\log(a_i/b_i)$ and $s_i=a_i+b_i$ for i=1, 2. To break the symmetry between the two alleles and impose a labeling of alleles so that $r_1 \leq r_2$ we use a $N(\mu=0, \sigma=2)$ prior for the average of $r_1$ and $r_2$, and a zero-inflated gamma(k=1, ($\beta$=0.5) distribution as a prior for the difference $d=r_1-r_2 \geq 0$. The zero-inflation puts a 0.5 prior probability mass on the difference being exactly zero, so the model can be used for 4qA/4qA, 4qA/4qB, or unknown genotypes. One could also adjust the prior based on known genotype data, or use the posterior probability that d>0 as a measure of evidence for allele-specific methylation. We use a gamma(k=1, $\beta$=0.025) prior for $s_1$ and $s_2$. A small fraction of sequences are missing methylation data at a small number (1-3) of sites; N was decreased accordingly for these sequences. Posterior means for the parameters of interest were computed using Markov Chain Monte Carlo (MCMC), with the Rjags (v3-14) interface to the JAGS (v3.3.0) sampler. We used 1000 MCMC steps for burn-in, followed by 30000 MCMC steps for inference; convergence was monitored with the Gelman-Rubin diagnostic (PFSR<1.01) [97] based on three chains run in parallel.

FIG. 25 (top) shows an example (16Abic) in which clones clearly separate into two clusters with distinct methylation percentages, and the two components of the mixture correspond to these two clusters, while allowing for slight deviations from 50% of clones in each cluster; FIG. 25 (bottom) shows an example (17Ubic) in which the clones do not clearly separate into two clusters and the two estimated mixture components are nearly the same, with the allele of origin ambiguous for all clones; as the genotype of this sample is 4qA/4qB, we do not expect to see evidence of allele specific methylation here. Bayesian allele-specific estimates depend on the prior probability distributions specified, but we confirmed that the reported differences between groups remained significant for other choices of parameters for the priors (two-fold increase or decrease for standard deviation $\sigma$ of normal prior and rate parameters $\beta$ for gamma priors).

Comparisons of DNA methylation between disease classes. For comparisons of DUX4 gene body methylation between FSHD-affected, nonmanifesting, and control samples, we first used the procedure described above to estimate the average methylation percentage for the 4A allele with lowest average methylation. For FSHD1 samples this is expected to be the contracted D4Z4 4A allele. We use the same procedure for control samples with no contracted alleles for uniformity. We likewise use this procedure for samples believed to have only one amplified 4A allele; in such cases the two allele-specific methylation estimates are typically quite close (within a percent or two, although larger deviations did sometimes occur, particularly in blood, perhaps representing increased mixing of multiple cell lineages).

We used a linear mixed effect (LME) model to fit the values y=log(a/b) for each sample, with fixed effects for cell type (myocyte or blood) and disease class (FSHD-affected, nonmanifesting, or control), including interactions between them, and a random effect for family. We also included an additive fixed effect for assay type (4qA or 4qA-L), as these assess different CpG sites that may have different baseline methylation percentages; indeed, for the 4qA assay there are variations in CpG methylation probabilities across the length of the sequence, with the central third of the CpG sites typically showing less methylation than the first third (FIG. 26). Because we had limited 4qA-L data, we did not attempt to model interactions between assay type and cell type or disease class here. For sample 17A, which had both 4qA and 4qA-L alleles, we used the 4qA assay as it gave a smaller value of y. This corresponded to the shorter allele (19 kb vs. 87 kb) as desired; however, in the absence of genotyping data a known baseline difference in methylation between 4qA and 4qA-L alleles could be adjusted for in deciding which should be regarded as the less methylated allele.

Note that y is equal to the log odds ratio $\log(p/(1-p))$, where p is the average fraction of CpG sites methylated. This logit transformation avoids the compression of values near p=0 and p=1. Estimated means and confidence intervals were transformed back to percentages in figures and tables. Models were fit using the R package lme4 (v1.1-7), and likelihood ratio tests were used for assessing significance. Because FSHD-affected subjects with nonmanifesting first-degree relatives may as a group differ from other FSHD subjects (due e.g. to nonmanifesting individuals tending to have borderline D4Z4 repeat lengths), we performed these tests with FSHD subjects divided into two subgroups, allowing nonmanifesting subjects to be compared with just their affected relatives (subgroup FSHD(b)) in a joint model that also includes the other FSHD cases (subgroup FSHD(a)). (For these particular FSHD samples, the two subgroups did not differ significantly; p=0.29 by LRT). Likelihood ratios were computed between the full model and models with two of the four disease-call subgroups collapsed, or with the two cell types collapsed, with the 1me4 anova function.

qRT-PCR. Total RNAs were extracted using Trizol (Invitrogen) and purified using the RNeasy Mini kit (Qiagen) after on-column DNase I digestion. Total RNA (2 µg) was used for cDNA synthesis using Superscript III Reverse Transcriptase (Invitrogen), and 200 ng of cDNA were used for DUX4-fl qPCR analysis as described [33]. All data were normalized to levels of 18S rRNA [98]. Oligonucleotide primer sequences are provided in [33]. For the analysis of ANKRD1 mRNA expression, 40 ng of cDNA were used with primers hANKRD1 For: GCCTACGTTTCTGAAGGCTG (SEQ ID NO: 16) and Rev: GTGGATTCAAGCATATCACGGAA (SEQ ID NO: 17).

Abbreviations

ADC: 5-aza-2'-deoxycytidine (Decitabine)
BSS: bisulfite sequencing
BS PCR: bisulfite PCR
CH: Chaetocin
FSHD: Facioscapulohumeral muscular dystrophy
MyHC: myosin heavy chain
PCR: polymerase chain reaction
qRT-PCR: quantitative reverse transcriptase PCR
RU: repeat unit
TSA: Trichostatin A

REFERENCES

1. Padberg G W: Facioscapulohumeral Disease [thesis]. Leiden, the Netherlands: Leiden University. 1982.
2. Tawil R: Facioscapulohumeral muscular dystrophy. *Neurotherapeutics* 2008, 5:601-606.
3. Padberg G W, van Engelen B G: Facioscapulohumeral muscular dystrophy. *Curr Opin Neurol* 2009, 22:539-542.
4. de Greef J C, Lemmers R J, van Engelen B G, Sacconi S, Venance S L, Frants R R, Tawil R, van der Maarel S M: Common epigenetic changes of D4Z4 in contraction-dependent and contraction-independent FSHD. *Hum Mutat* 2009, 30:1449-1459.
5. Lemmers R J, Tawil R, Petek L M, Balog J, Block G J, Santen G W, Amell A M, van der Vliet P J, Almomani R, Straasheijm K R, et al: Digenic inheritance of an SMCHD1 mutation and an FSHD-permissive D4Z4 allele causes facioscapulohumeral muscular dystrophy type 2. *Nat Genet* 2012, 44:1370-1374.
6. Sacconi S, Lemmers R J, Balog J, van der Vliet P J, Lahaut P, van Nieuwenhuizen M P, Straasheijm K R, Debipersad R D, Vos-Versteeg M, Salviati L, et al: The FSHD2 Gene SMCHD1 Is a Modifier of Disease Severity in Families Affected by FSHD1. *Am J Hum Genet* 2013, 93:744-751.
7. van der Maarel S M, Miller D G, Tawil R, Filippova G N, Tapscott S J: Facioscapulohumeral muscular dystrophy: consequences of chromatin relaxation. *Curr Opin Neurol* 2012.
8. Himeda C L, Jones T I, Jones P L: Facioscapulohumeral muscular dystrophy as a model for epigenetic regulation and disease. *Antioxidants & redox signaling* 2014, In press.
9. Prevalence of rare diseases: Bibliographic data in Orphanet Report Series: Rare Diseases Collection [http://www.orpha.net/orphacom/cahiers/docs/GB/Prevalence_of_rare_diseases_by_alphabetical_list.pdf]
10. Deenen J C, Arnts H, van der Maarel S M, Padberg G W, Verschuuren J J, Bakker E, Weinreich S S, Verbeek A L, van Engelen B G: Population-based incidence and prevalence of facioscapulohumeral dystrophy. *Neurology* 2014.
11. Wijmenga C, Hewitt J E, Sandkuijl L A, Clark L N, Wright T J, Dauwerse H G, Gruter A M, Hofker M H, Moerer P, Williamson R, et al: Chromosome 4q DNA rearrangements associated with facioscapulohumeral muscular dystrophy. *Nat Genet* 1992, 2:26-30.
12. van Deutekom J C, Wijmenga C, van Tienhoven E A, Gruter A M, Hewitt J E, Padberg G W, van Ommen G J, Hofker M H, Frants R R: FSHD associated DNA rearrangements are due to deletions of integral copies of a 3.2 kb tandemly repeated unit. *Hum Mol Genet* 1993, 2:2037-2042.
13. Schaap M, Lemmers R J, Maassen R, van der Vliet P J, Hoogerheide L F, van Dijk H K, Basturk N, de Knijff P, van der Maarel S M: Genome-wide analysis of macrosatellite repeat copy number variation in worldwide populations: evidence for differences and commonalities in size distributions and size restrictions. *BMC Genomics* 2013, 14:143.
14. Rossi M, Ricci E, Colantoni L, Galluzzi G, Frusciante R, Tonali P A, Felicetti L: The Facioscapulohumeral muscular dystrophy region on 4qter and the homologous locus on 10qter evolved independently under different evolutionary pressure. *BMC medical genetics* 2007, 8:8.
15. Lemmers R J, de Kievit P, Sandkuijl L, Padberg G W, van Ommen G J, Frants R R, van der Maarel S M: Facioscapulohumeral muscular dystrophy is uniquely associated with one of the two variants of the 4q subtelomere. *Nat Genet* 2002, 32:235-236.
16. Lemmers R J, Wohlgemuth M, van der Gaag K J, van der Vliet P J, van Teijlingen C M, de Knijff P, Padberg G W, Frants R R, van der Maarel S M: Specific sequence variations within the 4q35 region are associated with facioscapulohumeral muscular dystrophy. *Am J Hum Genet* 2007, 81:884-894.
17. Lemmers R J, van der Vliet P J, Klooster R, Sacconi S, Camano P, Dauwerse J G, Snider L, Straasheijm K R, van Ommen G J, Padberg G W, et al: A unifying genetic model for facioscapulohumeral muscular dystrophy. *Science* 2010, 329:1650-1653.
18. de Greef J C, Lemmers R J, Camano P, Day J W, Sacconi S, Dunand M, van Engelen B G, Kiuru-Enari S, Padberg G W, Rosa A L, et al: Clinical features of facioscapulohumeral muscular dystrophy 2. *Neurology* 2010, 75:1548-1554.
19. Hewitt J E, Lyle R, Clark L N, Valleley E M, Wright T J, Wijmenga C, van Deutekom J C, Francis F, Sharpe P T, Hofker M, et al: Analysis of the tandem repeat locus D4Z4 associated with facioscapulohumeral muscular dystrophy. *Hum Mol Genet* 1994, 3:1287-1295.
20. van Overveld P G, Enthoven L, Ricci E, Rossi M, Felicetti L, Jeanpierre M, Winokur S T, Frants R R, Padberg G W, van der Maarel S M: Variable hypomethylation of D4Z4 in facioscapulohumeral muscular dystrophy. *Ann Neurol* 2005, 58:569-576.

21. Zeng W, de Greef J C, Chen Y Y, Chien R, Kong X, Gregson H C, Winokur S T, Pyle A, Robertson K D, Schmiesing J A, et al: Specific loss of histone H3 lysine 9 trimethylation and HP1gamma/cohesin binding at D4Z4 repeats is associated with facioscapulohumeral dystrophy (FSHD). *PLoS Genet* 2009, 5:e1000559.
22. Balog J, Thijssen P E, de Greef J C, Shah B, van Engelen B G, Yokomori K, Tapscott S J, Tawil R, van der Maarel S M: Correlation analysis of clinical parameters with epigenetic modifications in the DUX4 promoter in FSHD. *Epigenetics* 2012, 7:1-6.
23. Mitsuhashi S, Boyden S E, Estrella E A, Jones T I, Rahimov F, Yu T W, Darras B T, Amato A A, Folkerth R D, Jones P L, et al: Exome sequencing identifies a novel SMCHD1 mutation in facioscapulohumeral muscular dystrophy 2. *Neuromuscul Disord* 2013, 23:975-980.
24. Winston J, Duerden L, Mort M, Frayling I M, Rogers M T, Upadhyaya M: Identification of two novel SMCHD1 sequence variants in families with FSHD-like muscular dystrophy. *Eur J Hum Genet* 2014.
25. Lemmers R J, Goeman J J, Van Der Vliet P J, Van Nieuwenhuizen M P, Balog J, Vos-Versteeg M, Camano P, Ramos Arroyo M A, Jerico I, Rogers M T, et al: Inter-individual differences in CpG methylation at D4Z4 correlate with clinical variability in FSHD1 and FSHD2. *Hum Mol Genet* 2015, 24:659-669.
26. Blewitt M E, Gendrel A V, Pang Z, Sparrow D B, Whitelaw N, Craig J M, Apedaile A, Hilton D J, Dunwoodie S L, Brockdorff N, et al: SmcHD1, containing a structural-maintenance-of-chromosomes hinge domain, has a critical role in X inactivation. *Nat Genet* 2008, 40:663-669.
27. Gendrel A V, Apedaile A, Coker H, Termanis A, Zvetkova I, Godwin J, Tang Y A, Huntley D, Montana G, Taylor S, et al: Smchd1-dependent and -independent pathways determine developmental dynamics of CpG island methylation on the inactive X chromosome. *Dev Cell* 2012, 23:265-279.
28. Mould A W, Pang Z, Pakusch M, Tonks I D, Stark M, Carrie D, Mukhopadhyay P, Seidel A, Ellis J J, Deakin J, et al: Smchd1 regulates a subset of autosomal genes subject to monoallelic expression in addition to being critical for X inactivation. *Epigenetics & chromatin* 2013, 6:19.
29. Larsen M, Rost S, El Hajj N, Ferbert A, Deschauer M, Walter M C, Schoser B, Tacik P, Kress W, Muller C R: Diagnostic approach for FSHD revisited: SMCHD1 mutations cause FSHD2 and act as modifiers of disease severity in FSHD1. *Eur J Hum Genet* 2014.
30. Snider L, Geng L N, Lemmers R J, Kyba M, Ware C B, Nelson A M, Tawil R, Filippova G N, van der Maarel S M, Tapscott S J, Miller D G: Facioscapulohumeral dystrophy: incomplete suppression of a retrotransposed gene. *PLoS Genet* 2010, 6:e1001181.
31. Wuebbles R D, Long S W, Hanel M L, Jones P L: Testing the effects of FSHD candidate gene expression in vertebrate muscle development. *Int J Clin Exp Pathol* 2010, 3:386-400.
32. Wallace L M, Garwick S E, Mei W, Belayew A, Coppee F, Ladner K J, Guttridge D, Yang J, Harper S Q: DUX4, a candidate gene for facioscapulohumeral muscular dystrophy, causes p53-dependent myopathy in vivo. *Ann Neurol* 2011, 69:540-552.
33. Jones T I, Chen J C, Rahimov F, Homma S, Arashiro P, Beermann M L, King O D, Miller J B, Kunkel L M, Emerson C P, Jr., et al: Facioscapulohumeral muscular dystrophy family studies of DUX4 expression: evidence for disease modifiers and a quantitative model of pathogenesis. *Hum Mol Genet* 2012, 21:4419-4430.
34. Geng L N, Yao Z, Snider L, Fong A P, Cech J N, Young J M, van der Maarel S M, Ruzzo W L, Gentleman R C, Tawil R, Tapscott S J: DUX4 Activates Germline Genes, Retroelements, and Immune Mediators: Implications for Facioscapulohumeral Dystrophy. *Dev Cell* 2012, 22:38-51.
35. Krom Y D, Thijssen P E, Young J M, den Hamer B, Balog J, Yao Z, Maves L, Snider L, Knopp P, Zammit P S, et al: Intrinsic Epigenetic Regulation of the D4Z4 Macrosatellite Repeat in a Transgenic Mouse Model for FSHD. *PLoS Genet* 2013, 9:e1003415.
36. Caruso N, Herberth B, Bartoli M, Puppo F, Dumonceaux J, Zimmermann A, Denadai S, Lebosse M, Roche S, Geng L, et al: Deregulation of the Protocadherin Gene FAT1 Alters Muscle Shapes: Implications for the Pathogenesis of Facioscapulohumeral Dystrophy. *PLoS Genet* 2013, 9:e1003550.
37. Gabriels J, Beckers M C, Ding H, De Vriese A, Plaisance S, van der Maarel S M, Padberg G W, Frants R R, Hewitt J E, Collen D, Belayew A: Nucleotide sequence of the partially deleted D4Z4 locus in a patient with FSHD identifies a putative gene within each 3.3 kb element. *Gene* 1999, 236:25-32.
38. Kowaljow V, Marcowycz A, Ansseau E, Conde C B, Sauvage S, Matteotti C, Arias C, Corona E D, Nunez N G, Leo 0, et al: The DUX4 gene at the FSHD1A locus encodes a pro-apoptotic protein. *Neuromuscul Disord* 2007, 17:611-623.
39. Bosnakovski D, Xu Z, Gang E J, Galindo C L, Liu M, Simsek T, Garner H R, Agha-Mohammadi S, Tassin A, Coppee F, et al: An isogenetic myoblast expression screen identifies DUX4-mediated FSHD-associated molecular pathologies. *EMBO J* 2008, 27:2766-2779.
40. Young J M, Whiddon J L, Yao Z, Kasinathan B, Snider L, Geng L N, Balog J, Tawil R, van der Maarel S M, Tapscott S J: DUX4 binding to retroelements creates promoters that are active in FSHD muscle and testis. *PLoS Genet* 2013, 9:e1003947.
41. Tassin A, Laoudj-Chenivesse D, Vanderplanck C, Barro M, Charron S, Ansseau E, Chen Y W, Mercier J, Coppee F, Belayew A: DUX4 expression in FSHD muscle cells: how could such a rare protein cause a myopathy? *J Cell Mol Med* 2013, 17:76-89.
42. Broucqsault N, Morere J, Gaillard M C, Dumonceaux J, Torrents J, Salort-Campana E, Maues de Paula A, Bartoli M, Fernandez C, Chesnais A L, et al: Dysregulation of 4q35- and muscle-specific genes in fetuses with a short D4Z4 array linked to Facio-Scapulo-Humeral Dystrophy. *Hum Mol Genet* 2013.
43. Rakyan V K, Blewitt M E, Druker R, Preis J I, Whitelaw E: Metastable epialleles in mammals. *Trends Genet* 2002, 18:348-351.
44. Dolinoy D C, Das R, Weidman J R, Jirtle R L: Metastable epialleles, imprinting, and the fetal origins of adult diseases. *Pediatric research* 2007, 61:30R-37R.
45. Homma S, Chen J C, Rahimov F, Beermann M L, Hanger K, Bibat G M, Wagner K R, Kunkel L M, Emerson C P, Jr., Miller J B: A unique library of myogenic cells from facioscapulohumeral muscular dystrophy subjects and unaffected relatives: family, disease and cell function. *Eur J Hum Genet* 2012, 20:404-410.
46. Rahimov F, King O D, Leung D G, Bibat G M, Emerson C P, Jr., Kunkel L M, Wagner K R: Transcriptional profiling in facioscapulohumeral muscular dystrophy to identify candidate biomarkers. *Proc Natl Acad Sci USA* 2012, 109:16234-16239.
47. Himeda C L, Debarnot C, Homma S, Beermann M L, Miller J B, Jones P L, Jones T I: Myogenic enhancers regulate expression of the facioscapulohumeral muscular dystrophy associated DUX4 gene. *Mol Cell Biol* 2014, 34:1942-1955.
48. Jones T I, Yan C, Sapp P C, McKenna-Yasek D, Kang P B, Quinn C, Salameh J S, King O D, Jones P L: Identifying diagnostic DNA methylation profiles for facioscapulohumeral muscular dystrophy in blood and saliva using bisulfite sequencing. *Clinical epigenetics* 2014, 6:23.
49. Zeng W, Chen Y Y, Newkirk D A, Wu B, Balog J, Kong X, Ball A R, Jr., Zanotti S, Tawil R, Hashimoto N, et al: Genetic and Epigenetic Characteristics of FSHD-Associated 4q and 10q D4Z4 that are Distinct from Non-4q/10q D4Z4 Homologs. *Hum Mutat* 2014, 35:998-1010.
50. van Overveld P G, Lemmers R J, Sandkuijl L A, Enthoven L, Winokur S T,
Bakels F, Padberg G W, van Ommen G J, Frants R R, van der Maarel S M: Hypomethylation of D4Z4 in 4q-linked and non-4q-linked facioscapulohumeral muscular dystrophy. *Nat Genet* 2003, 35:315-317.
51. Gaillard M C, Roche S, Dion C, Tasmadjian A, Bouget G, Salort-Campana E, Vovan C, Chaix C, Broucqsault N, Morere J, et al: Differential DNA methylation of the D4Z4 repeat in patients with FSHD and asymptomatic carriers. *Neurology* 2014, 83:733-742.
52. Hartweck L M, Anderson L J, Lemmers R J, Dandapat A, Toso E A, Dalton J C, Tawil R, Day J W, van der Maarel S M, Kyba M: A focal domain of extreme demethylation within D4Z4 in FSHD2. *Neurology* 2013, 80:392-399.
53. Ottaviani A, Schluth-Bolard C, Gilson E, Magdinier F: D4Z4 as a prototype of CTCF and lamins-dependent insulator in human cells. *Nucleus* 2010, 1:30-36.
54. Ricci E, Galluzzi G, Deidda G, Cacurri S, Colantoni L, Merico B, Piazzo N, Servidei S, Vigneti E, Pasceri V, et al: Progress in the molecular diagnosis of facioscapulohumeral muscular dystrophy and correlation between the number of KpnI repeats at the 4q35 locus and clinical phenotype. *Ann Neurol* 1999, 45:751-757.
55. Wohlgemuth M, Lemmers R J, van der Kooi E L, van der Wielen M J, van Overveld P G, Dauwerse H, Bakker E, Frants R R, Padberg G W, van der Maarel S M: Possible phenotypic dosage effect in patients compound heterozygous for FSHD-sized 4q35 alleles. *Neurology* 2003, 61:909-913.
56. Tonini M M, Passos-Bueno M R, Cerqueira A, Matioli S R, Pavanello R, Zatz M: Asymptomatic carriers and gender differences in facioscapulohumeral muscular dystrophy (FSHD). *Neuromuscul Disord* 2004, 14:33-38.
57. Goto K, Nishino I, Hayashi Y K: Very low penetrance in 85 Japanese families with facioscapulohumeral muscular dystrophy 1A. *J Med Genet* 2004, 41:e12.
58. Sakellariou P, Kekou K, Fryssira H, Sofocleous C, Manta P, Panousopoulou A, Gounaris K, Kanavakis E: Mutation spectrum and phenotypic manifestation in FSHD Greek patients. *Neuromuscul Disord* 2012, 22:339-349.
59. Scionti I, Fabbri G, Fiorillo C, Ricci G, Greco F, D'Amico R, Termanini A, Vercelli L, Tomelleri G, Cao M, et al: Facioscapulohumeral muscular dystrophy: new insights from compound heterozygotes and implication for prenatal genetic counselling. *J Med Genet* 2012, 49:171-178.
60. Scionti I, Greco F, Ricci G, Govi M, Arashiro P, Vercelli L, Berardinelli A, Angelini C, Antonini G, Cao M, et al: Large-scale population analysis challenges the current criteria for the molecular diagnosis of fascioscapulohumeral muscular dystrophy. *Am J Hum Genet* 2012, 90:628-635.
61. Jones P A, Taylor S M: Cellular differentiation, cytidine analogs and DNA methylation. *Cell* 1980, 20:85-93.
62. Yoshida M, Kijima M, Akita M, Beppu T: Potent and specific inhibition of mammalian histone deacetylase both in vivo and in vitro by trichostatin A. *J Biol Chem* 1990, 265:17174-17179.
63. Stresemann C, Lyko F: Modes of action of the DNA methyltransferase inhibitors azacytidine and decitabine. *Int J Cancer* 2008, 123:8-13.
64. Komashko V M, Farnham P J: 5-azacytidine treatment reorganizes genomic histone modification patterns. *Epigenetics* 2010, 5:229-240.
65. Lin J C, Jeong S, Liang G, Takai D, Fatemi M, Tsai Y C, Egger G, Gal-Yam E N, Jones P A: Role of nucleosomal occupancy in the epigenetic silencing of the MLH1 CpG island. *Cancer cell* 2007, 12:432-444.
66. Si J, Boumber Y A, Shu J, Qin T, Ahmed S, He R, Jelinek J, Issa J P: Chromatin remodeling is required for gene reactivation after decitabine-mediated DNA hypomethylation. *Cancer Res* 2010, 70:6968-6977.
67. Taddei A, Maison C, Roche D, Almouzni G: Reversible disruption of pericentric heterochromatin and centromere function by inhibiting deacetylases. *Nature cell biology* 2001, 3:114-120.
68. Yang X J, Seto E: HATs and HDACs: from structure, function and regulation to novel strategies for therapy and prevention. *Oncogene* 2007, 26:5310-5318.
69. Chambers A E, Banerjee S, Chaplin T, Dunne J, Debernardi S, Joel S P, Young B D: Histone acetylation-mediated regulation of genes in leukaemic cells. *European journal of cancer* 2003, 39:1165-1175.
70. Glaser K B, Stayer M J, Waring J F, Stender J, Ulrich R G, Davidsen S K: Gene expression profiling of multiple histone deacetylase (HDAC) inhibitors: defining a common gene set produced by HDAC inhibition in T24 and MDA carcinoma cell lines. *Mol Cancer Ther* 2003, 2:151-163.
71. Cameron E E, Bachman K E, Myohanen S, Herman J G, Baylin S B: Synergy of demethylation and histone deacetylase inhibition in the re-expression of genes silenced in cancer. *Nat Genet* 1999, 21:103-107.
72. Juan A H, Derfoul A, Feng X, Ryall J G, Dell'Orso S, Pasut A, Zare H, Simone J M, Rudnicki M A, Sartorelli V: Polycomb EZH2 controls self-renewal and safeguards the transcriptional identity of skeletal muscle stem cells. *Genes Dev* 2011, 25:789-794.
73. Greiner D, Bonaldi T, Eskeland R, Roemer E, Imhof A: Identification of a specific inhibitor of the histone methyltransferase SU(VAR)3-9. *Nat Chem Biol* 2005, 1:143-145.
74. Rea S, Eisenhaber F, O'Carroll D, Strahl B D, Sun Z W, Schmid M, Opravil S, Mechtler K, Ponting C P, Allis C D, Jenuwein T: Regulation of chromatin structure by site-specific histone H3 methyltransferases. *Nature* 2000, 406:593-599.
75. Ricci G, Scionti I, Sera F, Govi M, D'Amico R, Frambolli I, Mele F, Filosto M, Vercelli L, Ruggiero L, et al: Large scale genotype-phenotype analyses indicate that novel prognostic tools are required for families with facioscapulohumeral muscular dystrophy. *Brain* 2013, 136:3408-3417.
76. de Greef J C, Wohlgemuth M, Chan O A, Hansson K B, Smeets D, Frants R R, Weemaes C M, Padberg G W, van der Maarel S M: Hypomethylation is restricted to the D4Z4 repeat array in phenotypic FSHD. *Neurology* 2007, 69:1018-1026.
77. Wijmenga c, Frants R R, Hewitt J E, van Deutekom J C, van Geel M, Wright T J, Padberg G W, Hofker M H, van Ommen G J: Molecular genetics of facioscapulohumeral muscular dystrophy. *Neuromuscul Disord* 1993, 3:487-491.
78. Ehrlich M, Jackson K, Tsumagari K, Camano P, Lemmers R J: Hybridization analysis of D4Z4 repeat arrays linked to FSHD. *Chromosoma* 2007, 116:107-116.
79. Nguyen K, Walrafen P, Bernard R, Attarian S, Chaix C, Vovan C, Renard E,
Dufrane N, Pouget J, Vannier A, et al: Molecular combing reveals allelic combinations in facioscapulohumeral dystrophy. *Ann Neurol* 2011, 70:627-633.
80. Tawil R, Forrester J, Griggs R C, Mendell J, Kissel J, McDermott M, King W, Weiffenbach B, Figlewicz D: Evidence for anticipation and association of deletion size with severity in facioscapulohumeral muscular dystrophy. The FSH-D Y Group. *Ann Neurol* 1996, 39:744-748.
81. Jung M, Pfeifer G P: Aging and DNA methylation. *BMC Biol* 2015, 13:7.
82. Day K, Waite L L, Thalacker-Mercer A, West A, Bamman M M, Brooks J D, Myers R M, Absher D: Differential DNA methylation with age displays both common and dynamic features across human tissues that are influenced by CpG landscape. *Genome Biol* 2013, 14:R102.
83. Horvath S, Zhang Y, Langfelder P, Kahn R S, Boks M P, van Eijk K, van den Berg L H, Ophoff R A: Aging effects on DNA methylation modules in human brain and blood tissue. *Genome Biol* 2012, 13:R97.
84. Bernstein B E, Meissner A, Lander E S: The mammalian epigenome. *Cell* 2007, 128:669-681.
85. Bonasio R, Tu S, Reinberg D: Molecular signals of epigenetic states. *Science* 2010, 330:612-616.
86. Rivera C M, Ren B: Mapping human epigenomes. *Cell* 2013, 155:39-55.
87. Tawil R, Van Der Maarel S M: Facioscapulohumeral muscular dystrophy. *Muscle Nerve* 2006, 34:1-15.
88. Pandya S, King W M, Tawil R: Facioscapulohumeral dystrophy. *Phys Ther* 2008, 88:105-113.
89. Tawil R, Storvick D, Feasby T E, Weiffenbach B, Griggs R C: Extreme variability of expression in monozygotic twins with FSH muscular dystrophy. *Neurology* 1993, 43:345-348.
90. Griggs R C, Tawil R, McDermott M, Forrester J, Figlewicz D, Weiffenbach B: Monozygotic twins with facioscapulohumeral dystrophy (FSHD): implications for genotype/phenotype correlation. FSH-D Y Group. *Muscle Nerve* 1995, 2:S50-55.
91. Tupler R, Barbierato L, Memmi M, Sewry C A, De Grandis D, Maraschio P, Tiepolo L, Ferlini A: Identical de novo mutation at the D4F104S1 locus in monozygotic male twins affected by facioscapulohumeral muscular dystrophy (FSHD) with different clinical expression. *J Med Genet* 1998, 35:778-783.
92. Yoon S, Stadler G, Beermann M L, Schmidt E V, Windelborn J A, Schneiderat P, Wright W E, Miller J B: Immortalized myogenic cells from congenital muscular dystrophy type 1A patients recapitulate aberrant caspase activation in pathogenesis: a new tool for MDC1A research. *Skelet Muscle* 2013, 3:28.
93. Miller J B, Crow M T, Stockdale F E: Slow and fast myosin heavy chain content defines three types of myotubes in early muscle cell cultures. *J Cell Biol* 1985, 101:1643-1650.
94. Rohde C, Zhang Y, Reinhardt R, Jeltsch A: BISMA—fast and accurate bisulfite sequencing data analysis of individual clones from unique and repetitive sequences. *BMC Bioinformatics* 2010, 11:230.
95. Fang F, Hodges E, Molaro A, Dean M, Hannon G J, Smith A D: Genomic landscape of human allele-specific DNA methylation. *Proc Natl Acad Sci USA* 2012, 109: 7332-7337.
96. Dolzhenko E, Smith A D: Using beta-binomial regression for high-precision differential methylation analysis in multifactor whole-genome bisulfite sequencing experiments. *BMC bioinformatics* 2014, 15:215.
97. Gelman A, Rubin D B: Inference from iterative simulation using multiple sequences. *Statistical science* 1992: 457-472.
98. Bodega B, Ramirez G D, Grasser F, Cheli S, Brunelli S, Mora M, Meneveri R, Marozzi A, Mueller S, Battaglioli E, Ginelli E: Remodeling of the chromatin structure of the facioscapulohumeral muscular dystrophy (FSHD) locus and upregulation of FSHD-related gene 1 (FRG1) expression during human myogenic differentiation. *BMC Biol* 2009, 7:41.

TABLE 3

Characteristics of cell donors [1, 2]

| Family | Donor* | Cells | Clinical | Familial Relations | Gender | Age# (yrs) | 4qA RUs§ | EcoRI/BlnI sizes and chr 4 haplotypes |
|---|---|---|---|---|---|---|---|---|
| 03 | 03A | Myocyte | FSHD1 | Proband** | F | 40 | 5.5 | 20 kb (4A161); 57 kb (4B163)^^ |
|  | 03U | Myocyte | Healthy | Sister of 03A | F | 42 | 47 | 80 kb (4B163)^^; 157 kb (4A161) |
| 07 | 07A | Myocyte | FSHD1 | Proband** | F | 18 | 8 | 29 kb (4A161); 53 kb (4A161) |
|  | 07U | Myocyte | Healthy | Mother of 07A | F | 49 | 15.5 | 34 kb (4B163)^^; 53 kb (4A161) |
| 09 | 09A | Myocyte | FSHD1 | Proband** | F | 31 | 7 | 25 kb (4A161); >112 kb (4B168)^^ |
|  | 09U | Myocyte | Healthy | Mother of 09A | F | 57 | >34 | >112 kb (4A161); >112 kb (4A166H) |
| 12 | 12A | Myocyte | FSHD1 | Proband** | F | 22 | 5 | 18 kb (4A161); 63 kb (4A161) |

TABLE 3-continued

Characteristics of cell donors [1, 2]

| Family | Donor* | Cells | Clinical | Familial Relations | Gender | Age# (yrs) | 4qA RUs§ | EcoRI/BlnI sizes and chr 4 haplotypes |
|---|---|---|---|---|---|---|---|---|
|  | 12U | Myocyte | Healthy | Sister of 12A | F | 24 | >34 | >112 kb (4A-L161)^; >112 kb (4B168)^^ |
| 15 | 15A | Myocyte | FSHD1 | Proband** | M | 66 | 8 | 28 kb (4A161); >112 kb (4B163)^^ |
|  | 15B | Myocyte | Nonmanifesting | Brother of 15A | M | 69 | 8 | 28 kb (4A161); >112 kb (4B163)^^ |
| 16 | 16A | Myocyte | FSHD1 | Proband** | F | 56 | 5.5 | 20 kb (4A161); 97 kb (4A161) |
|  | 16U | Myocyte | Healthy | Sister of 16A | F | 60 | 29 | 56 kb (4B168)^^; 97 kb (4A161) |
| 17 | 17A | Myocyte | FSHD1 | Proband** | M | 23 | 5 | 19 kb (4A161); 87 kb (4A-L161)^ |
|  | 17U | Myocyte | Healthy | Brother of 17A | M | 21 | >34 | 97 kb (4B163)^^; >112 kb (4A161) |
|  | 17V | Myocyte | Healthy | Father of 17A | M | 50 | 26 | 87 kb (4A-L161)^; >112 kb (4B163)^^ |
| 19 | 19A | Myocyte | FSHD1 | Proband** | M | 65 | 6 | 22 kb (4A161); 157 kb (4A161) |
|  | 19U | Myocyte | Healthy | Daughter of 19A | F | 41 | 23 | 79 kb (4A161); 157 kb (4A161) |
| 21 | 21A | Myocyte | FSHD1 | Proband** | F | 82 | 7 | 26 kb (4A161); >145 kb (4A-L161)^ |
|  | 21U | Myocyte | Healthy | Daughter of 21A | F | 48 | 42 | 63 kb (4B163)^^; 142 kb (4A-L161)^ |
| 28 | 28A | Myocyte | FSHD1 | Proband** | M | 44 | 8 | 29 kb (4A161); 75 kb (4A161) |
|  | 28B | Myocyte | Nonmanifesting | Father of 28A | M | 68 | 8 | 29 kb (4A161); 117 kb (4A166H) |
| 29 | 29A | Myocyte | FSHD1 | Proband** | M | 39 | 8.5 | 30 kb (4A161); 160 kb (4A166)^^ |
|  | 29B | Myocyte | Nonmanifesting | Mother of 29A | F | 70 | 8.5 | 30 kb (4A161); >160 kb (4A161H) |
| 30 | 30A | Myocyte | FSHD1 | Proband** | M | 57 | 8.5 | 30 kb (4A161); 137 kb (4B168)^^ |
|  | 30B | Myocyte | Nonmanifesting | Sister of 30A | F | 59 | 8.5 | 30 kb (4A161); 81 kb (4B163)^^ |
| 39 | 39A | PBMC | FSHD1 | Proband** | M | 45 | 8.5 | 30 kb (4A161); 107 kb (4A161) |
|  | 39U | PBMC | Healthy | Mother of 39A | F | 75 | 32 | 107 kb (4A161); 47 kb (4B163)^^ |
| 41 | 41A | PBMC | FSHD1 | Proband** | F | 34 | 4 | 14 kb (4A161); 102 kb (4A166)^^ |
|  | 41U | PBMC | Healthy | Father of 41A | M | 54 | 30 | 102 kb (4A166)^^; 87 kb (4B162)^^ |
| 43 | 43A | PBMC | FSHD1 | Proband** | F | 33 | 5 | 19 kb (4A161); 48 kb (4B163)^ |
|  | 43B | PBMC | Nonmanifesting | Mother of 43A | F | 62 | 5 | 19 kb (4A161); 47 kb (4B163)^^ |
| 46 | 46A | PBMC | FSHD1 | Proband** | F | 54 | 6 | 22 kb (4A161); 122 kb (4A161) |
|  | 46B | PBMC | Nonmanifesting | Sister of 46A | F | 53 | 6 | 22 kb (4A161); 132 kb (4A161) |
| 47 | 47A | PBMC | FSHD1 | Proband** | M | 30 | 8.5 | 30 kb (4A161); 77 kb (4A166)^^ |
|  | 47B | PBMC | Nonmanifesting | Mother of 47A | F | 51 | 8.5 | 30 kb (4A161); 102 kb (4A166)^^ |
|  | 47C | PBMC | Asymptomatic | Sister of 47A | F | 25 | 8.5 | 30 kb (4A161); 112 kb (4B163)^^ |
| 48 | 48A | PBMC | Nonmanifesting | Proband** | F | 52 | 6 | 21 kb (4A161); 67 kb (4B163)^^ |
|  | 48B | PBMC | FSHD1 | Son of 48A | M | 20 | 6 | 21 kb (4A161); 77 kb (4B168)^^ |
|  | 48C | PBMC | FSHD1 | Son of 48A | M | 19 | 6 | 21 kb (4A161); 92 kb (4B163)^^ |
| 49 | 49A | PBMC | Nonmanifesting | Proband** | M | 46 | 6 | 22 kb (4A161); 147 kb (4B163)^^ |
|  | 49C | PBMC | FSHD1 | Brother of 49A | M | 56 | 6 | 22 kb (4A161); >145 kb (4B168)^^ |
| 51 | 51U | PBMC | Healthy | Mother of 51A | F | 39 | >44 | >145 kb (4A161); 72 kb (4B163)^^ |
|  | 51C | PBMC | FSHD1 | Father of 51A | M | 43 | 8 | 29 kb (4A161); 52 kb (4B168)^^ |

TABLE 3-continued

Characteristics of cell donors [1, 2]

| Family | Donor* | Cells | Clinical | Familial Relations | Gender | Age# (yrs) | 4qA RUs§ | EcoRI/BlnI sizes and chr 4 haplotypes |
|---|---|---|---|---|---|---|---|---|
|  | 51D | PBMC | FSHD1 | Sister of 51C | F | 48 | 8 | 29 kb (4A161); 52 kb (4B168)^^ |

*Donors were designated by cohort (family) number (e.g., 07, 09, or 17) followed by a letter A-D for the genetically FSHD1 subjects or a letter U-Z for the unaffected first-degree relative(s).
**FSHD1 was confirmed by a shortened 4q D4Z4 repeat array identified by an EcoRI/BlnI restriction fragment of <35 kb coupled with a 4qA subtelomere allele [1, 2].
§Estimated number of D4Z4 repeat units (RU) calculated based on (EcoRI/BlnI fragment kb − 2)/3.3 = RUs rounded to 0.5 for the shortest FSHD-permissive allele.
Age at time of enrollment in the study
~These alleles designated as 4A haplotypes by southern blotting are 4A-L and are not amplified or analyzed by the 4qA BSS assay; the 4qA-L BSS assay is used for the analysis of these alleles.
^^These alleles are the nonpermissive chromosome 4 haplotypes (4A166, 4B162, 4B163, 4B168) and not amplified by the 4qA or 4qA-L BSS assays.
Nonmanifesting is defined in this study as the subject having no discernible weakness on clinical examination.

1. Homma S, Chen J C, Rahimov F, Beermann M L, Hanger K, Bibat G M, Wagner K R, Kunkel L M, Emerson C P, Jr., Miller J B: A unique library of myogenic cells from facioscapulohumeral muscular dystrophy subjects and unaffected relatives: family, disease and cell function. *Eur J Hum Genet* 2012, 20:404-410.
2. Jones T I, Chen J C, Rahimov F, Homma S, Arashiro P, Beermann M L, King O D, Miller J B, Kunkel L M, Emerson C P, Jr., et al: Facioscapulohumeral muscular dystrophy family studies of DUX4 expression: evidence for disease modifiers and a quantitative model of pathogenesis. *Hum Mol Genet* 2012, 21:4419-4430.

TABLE 4

DUX4-FL expression in differentiated myogenic cell cultures by individual donor and muscle of origin

| | | | #DUX4-FL + ve nuclei per 1,000 nuclei in MyHC + ve cells, ave ± SE (n) | |
|---|---|---|---|---|
| Family | Donor | Disease Status | Biceps-derived (bic) | Deltoid-derived (del) |
| 07 | 07A | FSHD | 0.095 ± 0.028 (14)** | 0.17 ± 0.09 (4) |
|  | 07U | Unaffected | 0.00 ± 0.00 (14)** | 0.015 ± 0.015 (4) |
| 09 | 09A | FSHD | 0.79 ± 0.21 (14)** | 2.14 ± 0.84 (4)* |
|  | 09U | Unaffected | 0.12 ± 0.08 (14)** | 0.00 ± 0.00 (4)* |
| 17 | 17A | FSHD | 3.71 ± 0.63 (14)** | 4.76 ± 0.97 (4)** |
|  | 17U | Unaffected | 0.021 ± 0.015 (12)** | 0.012 ± 0.012 (4)** |
|  | 17V | Unaffected | 0.00 ± 0.00 (7)** | n.d. |

*$P < 0.05$,
**$P < 0.01$ by t-test for FSHD vs. Unaffected within the indicated family.

TABLE 5

Comparison of percent DNA methylation between cells derived from FSHD1-affected and nonmanifesting familial cohorts using the 4qA BSS assay

| Cohort | Manifesting | Nonmanifesting | EcoRI/BlnI | D4Z4 RU* |
|---|---|---|---|---|
| 15 | 15.2% | 25.4% | 28 kb | 8 |
| 28 | 14.6% | 25.2% | 29 kb | 8 |
| 29 | 6.5% | 12.5% | 30 kb | 8.5 |
| 30 | 10.6% | 32.6% | 30 kb | 8.5 |
| 43 | 14.2% | 15.5% | 19 kb | 5 |
| 46 | 13.7% | 27.6% | 22 kb | 6 |
| 47 | 9.3% | 14.9% & 16.9% | 30 kb | 8.5 |
| 48 | 7.3% & 4.9% | 11.7% | 21 kb | 6 |
| 49 | 8.0% | 18.8% | 22 kb | 6 |

*Calculated as D4Z4 RU = (EcoRI/BlnI fragment kb − 2 kb)/3.3

TABLE 6

Summary of percent methylation

| Subject | Cells | BSS_assay | Clinical | num_seqs | mean | min | Q1 | median | Q3 | max | est_low | est_high | est_both |
|---|---|---|---|---|---|---|---|---|---|---|---|---|---|
| 03A | Myocyte | 4qA | FSHD1 | 10 | 5.7 | 1.8 | 1.8 | 4.5 | 7.1 | 14.3 | 5.8 | 7.0 | 6.3 |
| 03U | Myocyte | 4qA | Healthy | 10 | 72.7 | 58.9 | 67.9 | 70.5 | 80.4 | 83.9 | 71.6 | 73.2 | 72.4 |
| 07A | Myocyte | 4qA | FSHD1 | 18 | 24.5 | 5.4 | 7.1 | 25.9 | 28.6 | 58.9 | 17.8 | 30.1 | 24.7 |
| 07U | Myocyte | 4qA | Healthy | 16 | 50.2 | 10.7 | 38.7 | 58.0 | 62.5 | 69.6 | 35.2 | 59.0 | 49.4 |
| 09A | Myocyte | 4qA | FSHD1 | 10 | 6.4 | 0.0 | 3.6 | 6.2 | 8.9 | 12.5 | 6.7 | 7.7 | 7.0 |
| 09U | Myocyte | 4qA | Healthy | 9 | 72.0 | 64.3 | 65.6 | 75.0 | 75.0 | 78.6 | 71.0 | 72.2 | 71.7 |
| 12A | Myocyte | 4qA | FSHD1 | 10 | 28.4 | 10.7 | 17.3 | 26.8 | 35.7 | 50.0 | 25.6 | 31.4 | 28.6 |
| 12U | Myocyte | 4qA-L | Healthy | 12 | 84.2 | 70.0 | 76.7 | 85.0 | 93.3 | 96.7 | 82.1 | 85.7 | 83.9 |
| 15A | Myocyte | 4qA | FSHD1 | 10 | 16.1 | 7.1 | 8.9 | 14.3 | 19.6 | 37.5 | 15.2 | 17.6 | 16.5 |
| 15B | Myocyte | 4qA | Nonmanif | 10 | 29.1 | 7.1 | 17.9 | 25.9 | 37.5 | 67.9 | 25.4 | 32.7 | 29.7 |
| 16A | Myocyte | 4qA | FSHD1 | 15 | 39.2 | 1.8 | 8.9 | 42.9 | 62.9 | 87.5 | 9.6 | 59.4 | 38.5 |
| 16U | Myocyte | 4qA | Healthy | 36 | 40.7 | 5.4 | 30.6 | 42.9 | 53.6 | 73.2 | 34.3 | 47.1 | 40.4 |
| 17A | Myocyte | 4qA | FSHD1 | 20 | 12.8 | 1.8 | 4.5 | 13.4 | 19.6 | 26.8 | 9.2 | 16.2 | 12.9 |
| 17A | Myocyte | 4qA-L | FSHD1 | 12 | 76.1 | 60.0 | 68.3 | 78.3 | 83.3 | 93.3 | 74.6 | 77.0 | 75.9 |
| 17U | Myocyte | 4qA | Healthy | 20 | 71.4 | 58.9 | 64.3 | 69.6 | 76.8 | 92.9 | 70.0 | 72.2 | 71.4 |
| 19A | Myocyte | 4qA | FSHD1 | 20 | 38.9 | 0.0 | 6.2 | 44.6 | 64.3 | 91.1 | 9.5 | 58.3 | 37.0 |
| 19U | Myocyte | 4qA | Healthy | 22 | 54.8 | 32.1 | 41.1 | 58.0 | 66.1 | 78.2 | 48.4 | 60.2 | 54.7 |
| 21A | Myocyte | 4qA | FSHD1 | 13 | 19.0 | 10.7 | 12.5 | 18.2 | 23.2 | 32.1 | 18.8 | 19.9 | 19.3 |
| 21A | Myocyte | 4qA-L | FSHD1 | 15 | 80.7 | 60.0 | 80.0 | 83.3 | 83.3 | 90.0 | 79.8 | 80.7 | 80.3 |
| 21U | Myocyte | 4qA-L | Healthy | 12 | 82.5 | 63.3 | 78.3 | 83.3 | 86.7 | 93.3 | 81.3 | 82.7 | 82.1 |
| 28A | Myocyte | 4qA | FSHD1 | 10 | 22.3 | 3.6 | 7.1 | 26.8 | 32.1 | 39.3 | 14.7 | 28.2 | 22.4 |
| 28B | Myocyte | 4qA | Nonmanif | 10 | 33.6 | 16.1 | 21.4 | 25.9 | 51.8 | 51.8 | 25.2 | 44.3 | 33.8 |
| 29A | Myocyte | 4qA | FSHD1 | 11 | 6.7 | 0.0 | 3.6 | 5.4 | 10.7 | 14.3 | 6.5 | 8.0 | 7.2 |
| 29B | Myocyte | 4qA | Nonmanif | 20 | 40.4 | 1.8 | 8.9 | 41.1 | 70.5 | 78.6 | 12.5 | 68.7 | 38.7 |
| 30A | Myocyte | 4qA | FSHD1 | 11 | 14.1 | 1.8 | 5.4 | 7.1 | 21.0 | 46.4 | 10.5 | 17.7 | 14.7 |
| 30B | Myocyte | 4qA | Nonmanif | 11 | 34.9 | 5.4 | 27.2 | 35.7 | 44.6 | 53.6 | 32.5 | 37.3 | 34.8 |
| 39A | PBMC | 4qA | FSHD1 | 15 | 38.7 | 1.8 | 16.1 | 42.9 | 65.2 | 73.2 | 16.3 | 58.5 | 37.7 |
| 39U | PBMC | 4qA | Healthy | 10 | 71.8 | 58.9 | 62.5 | 72.3 | 76.8 | 91.1 | 70.3 | 72.6 | 71.6 |
| 41A | PBMC | 4qA | FSHD1 | 13 | 7.7 | 0.0 | 1.8 | 3.6 | 8.9 | 42.9 | 5.9 | 9.8 | 8.5 |
| 43A | PBMC | 4qA | FSHD1 | 10 | 18.8 | 1.8 | 5.4 | 21.4 | 23.2 | 42.9 | 14.1 | 23.1 | 19.0 |
| 43B | PBMC | 4qA | Nonmanif | 12 | 30.5 | 0.0 | 11.6 | 38.4 | 44.6 | 53.6 | 14.7 | 42.5 | 29.4 |
| 46A | PBMC | 4qA | FSHD1 | 14 | 35.7 | 0.0 | 14.3 | 38.4 | 64.3 | 67.9 | 13.7 | 56.5 | 33.6 |
| 46B | PBMC | 4qA | Nonmanif | 14 | 42.4 | 1.8 | 16.1 | 42.0 | 66.1 | 80.4 | 27.5 | 58.2 | 41.6 |
| 47A | PBMC | 4qA | FSHD1 | 13 | 17.6 | 0.0 | 5.4 | 17.9 | 30.4 | 39.3 | 9.3 | 25.7 | 17.7 |
| 47B | PBMC | 4qA | Nonmanif | 11 | 16.5 | 5.4 | 8.5 | 14.3 | 24.6 | 33.9 | 15.0 | 18.5 | 16.8 |
| 47C | PBMC | 4qA | Asymptom | 12 | 24.7 | 1.8 | 10.7 | 22.7 | 38.8 | 55.4 | 16.8 | 31.9 | 24.7 |
| 48A | PBMC | 4qA | Nonmanif | 12 | 31.1 | 3.6 | 8.9 | 31.2 | 55.4 | 58.9 | 11.7 | 50.8 | 30.7 |
| 48B | PBMC | 4qA | FSHD1 | 13 | 14.1 | 0.0 | 3.1 | 12.5 | 21.9 | 42.9 | 7.3 | 21.0 | 14.5 |
| 48C | PBMC | 4qA | FSHD1 | 10 | 10.5 | 1.8 | 1.8 | 3.6 | 26.8 | 26.8 | 5.0 | 19.8 | 11.2 |
| 49A | PBMC | 4qA | Nonmanif | 11 | 27.3 | 1.8 | 12.5 | 25.5 | 42.4 | 57.1 | 18.8 | 35.4 | 27.2 |
| 49C | PBMC | 4qA | FSHD1 | 12 | 19.5 | 3.6 | 4.5 | 10.7 | 39.3 | 50.0 | 8.0 | 41.5 | 20.1 |
| 51C | PBMC | 4qA | FSHD1 | 11 | 24.2 | 1.8 | 17.9 | 21.4 | 36.2 | 42.9 | 21.5 | 26.9 | 24.2 |
| 51D | PBMC | 4qA | FSHD1 | 14 | 25.0 | 3.6 | 14.3 | 22.3 | 33.9 | 67.9 | 22.4 | 27.5 | 25.4 |
| 51U | PBMC | 4qA | Healthy | 16 | 72.5 | 41.1 | 67.9 | 72.3 | 86.6 | 87.5 | 68.8 | 76.6 | 72.3 |
| 03A | Myocyte | DUX4 5' | FSHD1 | 20 | 26.7 | 0.0 | 8.5 | 21.2 | 45.8 | 67.2 | 14.4 | 39.3 | 26.1 |
| 03U | Myocyte | DUX4 5' | Healthy | 15 | 77.2 | 64.4 | 69.9 | 72.9 | 86.0 | 93.2 | 74.9 | 79.2 | 77.1 |
| 07A | Myocyte | DUX4 5' | FSHD1 | 18 | 50.5 | 1.7 | 44.1 | 54.2 | 66.1 | 76.3 | 41.5 | 55.8 | 48.1 |
| 07U | Myocyte | DUX4 5' | Healthy | 18 | 44.7 | 5.1 | 16.9 | 48.7 | 67.8 | 79.7 | 22.9 | 63.7 | 43.4 |
| 09A | Myocyte | DUX4 5' | FSHD1 | 19 | 34.5 | 0.0 | 7.2 | 25.4 | 60.6 | 91.5 | 15.1 | 50.5 | 34.5 |
| 09U | Myocyte | DUX4 5' | Healthy | 19 | 56.8 | 31.0 | 37.3 | 55.9 | 74.6 | 86.4 | 41.0 | 72.4 | 56.9 |
| 12A | Myocyte | DUX4 5' | FSHD1 | 19 | 43.7 | 6.8 | 27.5 | 44.1 | 61.0 | 78.0 | 30.8 | 54.6 | 42.9 |
| 12U | Myocyte | DUX4 5' | Healthy | 17 | 66.5 | 37.3 | 55.9 | 67.2 | 79.2 | 86.4 | 62.1 | 71.1 | 66.4 |
| 15A | Myocyte | DUX4 5' | FSHD1 | 20 | 40.1 | 0.0 | 20.3 | 44.9 | 57.6 | 81.4 | 24.3 | 52.4 | 37.5 |
| 15B | Myocyte | DUX4 5' | Nonmanif | 20 | 64.2 | 6.8 | 43.2 | 75.4 | 85.6 | 91.5 | 40.4 | 82.0 | 61.9 |
| 17A | Myocyte | DUX4 5' | FSHD1 | 19 | 56.3 | 3.4 | 36.9 | 66.1 | 74.2 | 86.4 | 38.9 | 69.6 | 54.6 |
| 17U | Myocyte | DUX4 5' | Healthy | 18 | 72.0 | 22.0 | 62.7 | 78.0 | 84.7 | 89.8 | 66.9 | 77.3 | 71.2 |
| 28A | Myocyte | DUX4 5' | FSHD1 | 20 | 16.6 | 0.0 | 5.1 | 14.4 | 24.6 | 50.8 | 10.6 | 22.2 | 16.9 |
| 28B | Myocyte | DUX4 5' | Nonmanif | 20 | 31.4 | 3.4 | 19.5 | 29.7 | 43.2 | 83.1 | 30.4 | 33.4 | 31.7 |
| 29A | Myocyte | DUX4 5' | FSHD1 | 20 | 39.3 | 1.7 | 5.9 | 40.7 | 66.9 | 91.5 | 9.0 | 62.9 | 37.7 |
| 29B | Myocyte | DUX4 5' | Nonmanif | 20 | 54.4 | 0.0 | 36.4 | 59.3 | 72.9 | 88.1 | 45.9 | 61.7 | 52.6 |
| 30A | Myocyte | DUX4 5' | FSHD1 | 20 | 38.9 | 0.0 | 21.2 | 36.4 | 55.9 | 86.4 | 35.0 | 42.2 | 36.6 |
| 30B | Myocyte | DUX4 5' | Nonmanif | 20 | 30.8 | 3.4 | 16.9 | 29.0 | 45.8 | 59.3 | 23.9 | 37.8 | 30.7 |

Example 3

Epigenetic testing for diagnosis of FSHD using the method described herein has correctly identified all 75 genetically-confirmed FSHD cases tested as being FSHD and all 18 healthy cases as not being FSHD (Table 7). Therefore, this method is accurate in determining FSHD.

Epigenetic testing was also performed on 86 subjects with a known neuromuscular disease (NMD) diagnosis other than FSHD. These include LGMD (limb-girdle muscular dystrophy), OPMD (oculopharyngeal MD), EDMD (Emery-Dreifuss MD), DMD (Duchenne MD, BMD (Becker MD), DM1 (myotonic dystrophy, type 1), MDC1A (merosin-deficient congenital MD), HIBM (hereditary inclusion body myopathy), CMS (congenital myasthenic syndromes), CMTX (Charcot-Marie-Tooth disease), ALS (amyotrophic lateral sclerosis). Results indicate that the method described herein can distinguish FSHD from other NMDs (Table 7).

TABLE 7

| Genetically Confirmed | Sample No. | FSHD | Not FSHD |
| --- | --- | --- | --- |
| FSHD1 (affected) | 58 | 58 | 0 |
| FSHD1 (asymptomatic) | 12 | 12 | 0 |
| FSHD2 | 5 | 5 | 0 |
| Healthy | 18 | 0 | 18 |
| Total | 93 | 75 | 18 |
| Neuromuscular disease* | 86 | 4** | 82 |

*NMD diagnosis, but no genetic test for FSHD was performed.

**These 4 samples may in fact have FSHD (3 are LGMDs which are often clinically confused with FSHD) and need to be confirmed by genetic testing (e.g., using PFGE and Southern blotting).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining whether a human subject has, or is at risk of developing, facioscapulohumeral muscular dystrophy 2 (FSHD2) comprising performing a DNA methylation analysis of deoxycytosine-phosphate-deoxyguanine dinucleotides (CpGs) in a distal D4Z4 repeat unit of a D4Z4 repeat array and a proximal region of an A-type subtelomere of each of a chromosome 4qA allele and a chromosome 4qA-L allele of chromosome 4q, if present, wherein the DNA methylation analysis comprises:

i) performing polymerase chain reaction (PCR) using genomic DNA from at least one sample from the subject and a forward primer comprising the sequence of SEQ ID NO: 8 and a first reverse primer comprising the sequence of SEQ ID NO: 9 to obtain at least one first 4qA PCR product if the genomic DNA comprises a 4qA allele;
   ii) performing PCR using the at least one first 4qA PCR product, the forward primer comprising the sequence of SEQ ID NO: 8 and a second reverse primer comprising the sequence of SEQ ID NO: 10 to obtain at least one second 4qA PCR product if the genomic DNA comprises a 4qA allele;
   iii) performing PCR using genomic DNA from at least one sample from the subject and a forward primer comprising the sequence of SEQ ID NO: 11 and the first reverse primer comprising the sequence of SEQ ID NO: 9 to obtain at least one first 4qA-L PCR product if the genomic DNA comprises a 4qA-L allele;
   iv) performing PCR using the at least one first 4qA-L PCR product, the forward primer comprising the sequence of SEQ ID NO: 11 and the second reverse primer comprising the sequence of SEQ ID NO: 10 to obtain at least one second 4qA-L PCR product if the genomic DNA comprises a 4qA-L allele;
   v) performing bisulfite sequencing for each of the at least one second 4qA PCR product and the at least one second 4qA-L PCR product, if the genomic DNA comprises a 4qA allele and/or 4qA-L allele, respectively;
   vi) quantifying methylation of the CpGs in the distal D4Z4 repeat unit and the proximal region of the A-type subtelomere in each of the at least one second 4qA PCR product and the at least one second 4qA-L PCR product to obtain the first quartile of the methylation percent of the distal D4Z4 repeat unit and the proximal region of the A-type subtelomere of each of the second 4qA PCR product and the second 4qA-L PCR product, wherein if 25% or less of the CpGs in the distal D4Z4 repeat unit and the proximal region of the A-type subtelomere in the first quartile of the second 4qA PCR product are methylated or if 25% or less of the CpGs in the first quartile of the second 4qA-L PCR product are methylated, then the subject has, or is at risk of developing, FSHD2.

2. The method of claim 1 wherein if between about 35% of the CpGs in the first quartile of the analysis of the distal D4Z4 repeat unit and the proximal region of the A-type subtelomere are methylated, and the individual exhibits no detectable muscle weakness, then the individual is diagnosed as an FSHD2 carrier.

3. The method of claim 1 wherein if greater than about 35% of the CpGs in the first quartile of the analysis of the distal D4Z4 repeat unit and the proximal region of the A-type subtelomere are methylated, then the individual does not have, or is not at risk of developing, FSHD2.

4. The method of claim 1 wherein if no at least one first 4qA PCR product and no at least one first 4qA-L PCR product are produced by the PCR, then the subject does not have, or is not at risk of developing, FSHD2.

5. The method of claim 1, further comprising determining whether the distal D4Z4 repeat of the D4Z4 repeat array on chromosome 4q unit includes CpG #55, wherein if analysis of the distal D4Z4 repeat unit results in CpG #55 being absent, relative to a reference sequence, from all sequences of the at least one second 4qA PCR product and the at least one second 4qA-L PCR product being analyzed, then the subject does not have, or is not at risk of developing, FSHD2.

6. The method of claim 1, further comprising determining whether the distal D4Z4 repeat of the D4Z4 repeat array on chromosome 4q unit includes CpG #16 and CpG #55, wherein if analysis of the distal D4Z4 repeat unit results in both CpG #16 and CpG #55 being absent, relative to a reference sequence, from all sequences of the at least one second 4qA PCR product and the at least one second 4qA-L PCR product being analyzed, then the subject does not have, or is not at risk of developing, FSHD2.

7. The method of claim 1 wherein the individual is symptomatic for FSHD but produces a negative genetic test for FSHD1.

8. The method of claim 2 wherein the individual is an asymptomatic carrier of FSHD2.

9. The method of claim 1 wherein the methylation analysis is performed using bisulfate converted genomic DNA.

10. The method of claim 1 further comprising determining the sequence of a subtelomere of chromosome 4q, a subtelomere of 10q, one or more D4Z4 repeat units or a combination thereof.

11. The method of claim 1 wherein the sequence is determined by performing Sanger sequencing or next generation sequencing.

12. The method of claim 1 wherein the sample comprises one or more samples from one or more subjects that do not have FSHD.

13. The method of claim 1 wherein the sample is one or more fluids, one or more tissues, one or more cells or a combination thereof obtained from the subject.

14. The method of claim 13 wherein the sample is saliva, blood, myocytes, fibroblasts, tissue, hair or cultured cells.

* * * * *

UNITED STATES PATENT AND TRADEMARK OFFICE
CERTIFICATE OF CORRECTION

| | |
|---|---|
| PATENT NO. | : 10,870,886 B2 |
| APPLICATION NO. | : 15/516291 |
| DATED | : December 22, 2020 |
| INVENTOR(S) | : Peter L. Jones et al. |

Page 1 of 1

It is certified that error appears in the above-identified patent and that said Letters Patent is hereby corrected as shown below:

In the Claims

In Column 63, Claim 9, Line 16, please delete:
"sis is performed using bisulfate converted genomic DNA."
And insert:
--sis is performed using bisulfite converted genomic DNA.--

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*